US008298491B2

(12) United States Patent
Tonkovich et al.

(10) Patent No.: US 8,298,491 B2
(45) Date of Patent: *Oct. 30, 2012

(54) PROCESS FOR TREATING AND/OR FORMING A NON-NEWTONIAN FLUID USING MICROCHANNEL PROCESS TECHNOLOGY

(75) Inventors: Anna Lee Tonkovich, Dublin, OH (US); Ravi Arora, New Albany, OH (US); David Kilanowski, Dublin, OH (US); Eric Daymo, Dublin, OH (US)

(73) Assignee: Velocys, Inc., Plain City, OH (US)

( * ) Notice: Subject to any disclaimer, the term of this patent is extended or adjusted under 35 U.S.C. 154(b) by 26 days.

This patent is subject to a terminal disclaimer.

(21) Appl. No.: 13/281,889

(22) Filed: Oct. 26, 2011

(65) Prior Publication Data
US 2012/0058063 A1    Mar. 8, 2012

Related U.S. Application Data

(63) Continuation of application No. 11/737,955, filed on Apr. 20, 2007, now Pat. No. 8,048,383.

(60) Provisional application No. 60/793,519, filed on Apr. 20, 2006.

(51) Int. Cl.
*G05D 24/00* (2006.01)
(52) U.S. Cl. ........ 422/140; 422/146; 422/198; 422/224; 422/243; 137/4; 137/92
(58) Field of Classification Search .................. 422/140, 422/146, 198, 224, 243; 137/4, 137
See application file for complete search history.

(56) References Cited

U.S. PATENT DOCUMENTS

| | | | | | |
|---|---|---|---|---|---|
| 3,063,960 A | * | 11/1962 | Smith | ............................ | 525/406 |
| 3,143,124 A | * | 8/1964 | Todd | ............................... | 137/13 |
| 3,206,445 A | * | 9/1965 | Volk | ................................ | 526/75 |
| 3,356,646 A | * | 12/1967 | Wynstra et al. | ................. | 528/88 |
| 3,377,283 A | * | 4/1968 | McMillen | ...................... | 508/393 |
| 3,414,522 A | * | 12/1968 | Hoekstra | ........................... | 516/98 |
| 3,515,522 A | * | 6/1970 | Pecak et al. | .................... | 423/287 |
| 3,649,358 A | * | 3/1972 | Johnston, II | ................... | 427/565 |

(Continued)

FOREIGN PATENT DOCUMENTS
DE        246257        6/1987
(Continued)

OTHER PUBLICATIONS

Cybulski et al.; "Monoliths in Heterogeneous Catalysis"; Catal. Rev.—Sci. Eng., 36(2), 179-270 (1994).

(Continued)

*Primary Examiner* — In Suk Bullock
*Assistant Examiner* — Timothy G Kingan
(74) *Attorney, Agent, or Firm* — Renner, Otto, Boisselle & Sklar, LLP

(57) ABSTRACT

The disclosed invention relates to a process, comprising: conducting unit operations in at least two process zones in a process microchannel to treat and/or form a non-Newtonian fluid, a different unit operation being conducted in each process zone; and applying an effective amount of shear stress to the non-Newtonian fluid to reduce the viscosity of the non-Newtonian fluid in each process zone, the average shear rate in one process zone differing from the average shear rate in another process zone by a factor of at least about 1.2.

49 Claims, 35 Drawing Sheets

U.S. PATENT DOCUMENTS

| | | | |
|---|---|---|---|
| 3,784,596 A * | 1/1974 | Nagler | 524/238 |
| 3,796,560 A * | 3/1974 | Schrader et al. | 504/199 |
| 3,839,590 A * | 10/1974 | Battista | 514/773 |
| 3,882,049 A | 5/1975 | Bertolacini et al. | |
| 3,972,837 A | 8/1976 | Acres et al. | |
| 4,089,810 A | 5/1978 | Diwell et al. | |
| 4,096,095 A | 6/1978 | Cairns | |
| 4,289,652 A | 9/1981 | Hunter et al. | |
| 5,248,251 A | 9/1993 | Dalla Betta et al. | |
| 5,663,217 A * | 9/1997 | Kruse | 523/161 |
| 5,811,062 A | 9/1998 | Wegeng et al. | 422/129 |
| 6,040,266 A | 3/2000 | Fay, III et al. | |
| 6,126,723 A | 10/2000 | Drost et al. | 96/4 |
| 6,192,596 B1 | 2/2001 | Bennett et al. | 34/76 |
| 6,200,536 B1 | 3/2001 | Tonkovich et al. | 422/177 |
| 6,284,217 B1 | 9/2001 | Wang et al. | 423/651 |
| 6,305,834 B1 | 10/2001 | Schubert et al. | 366/144 |
| 6,440,895 B1 | 8/2002 | Tonkovich et al. | 502/439 |
| 6,451,864 B1 | 9/2002 | Wang et al. | 518/715 |
| 6,479,428 B1 | 11/2002 | Tonkovich et al. | 502/302 |
| 6,488,838 B1 | 12/2002 | Tonkovich et al. | 208/108 |
| 6,490,812 B1 | 12/2002 | Bennett et al. | 34/433 |
| 6,491,880 B1 | 12/2002 | Wang et al. | 422/211 |
| 6,503,298 B1 | 1/2003 | Monzyk et al. | 95/96 |
| 6,508,862 B1 | 1/2003 | Tonkovich et al. | 95/106 |
| 6,511,711 B2 * | 1/2003 | Quiel et al. | 427/458 |
| 6,533,840 B2 | 3/2003 | Martin et al. | 95/45 |
| 6,540,975 B2 | 4/2003 | Tonkovich et al. | 423/659 |
| 6,547,928 B2 * | 4/2003 | Barnholtz et al. | 162/127 |
| 6,558,634 B1 | 5/2003 | Wang et al. | 422/173 |
| 6,607,678 B2 | 8/2003 | Wang et al. | 252/373 |
| 6,616,909 B1 | 9/2003 | Tonkovich et al. | 423/848.1 |
| 6,622,519 B1 | 9/2003 | Mathias et al. | 62/611 |
| 6,637,463 B1 | 10/2003 | Lei et al. | 137/803 |
| 6,652,627 B1 | 11/2003 | Tonkovich et al. | 95/104 |
| 6,660,237 B2 | 12/2003 | Wang et al. | 422/222 |
| 6,666,909 B1 | 12/2003 | TeGrotenhuis et al. | 95/273 |
| 6,680,044 B1 | 1/2004 | Tonkovich et al. | 423/652 |
| 6,734,137 B2 | 5/2004 | Wang et al. | 502/328 |
| 6,762,149 B2 | 7/2004 | Tonkovich et al. | 502/439 |
| 6,814,781 B2 | 11/2004 | Tonkovich et al. | 95/90 |
| 6,851,171 B2 | 2/2005 | Schmitt | 29/469 |
| 6,855,229 B2 * | 2/2005 | McKay et al. | 162/179 |
| 6,875,247 B2 | 4/2005 | TeGrotenhuis et al. | 55/319 |
| 6,969,505 B2 | 11/2005 | Tonkovich et al. | 423/648.1 |
| 6,969,506 B2 | 11/2005 | Tonkovich et al. | 423/652 |
| 6,984,363 B2 | 1/2006 | Tonkovich et al. | 422/173 |
| 6,989,134 B2 | 1/2006 | Tonkovich et al. | 422/189 |
| 7,000,427 B2 | 2/2006 | Mathias et al. | 62/612 |
| 7,008,969 B2 | 3/2006 | Wang et al. | 518/715 |
| 7,014,835 B2 | 3/2006 | Mathias et al. | 423/652 |
| 7,029,647 B2 | 4/2006 | Tonkovich et al. | 423/584 |
| 7,045,114 B2 | 5/2006 | Tonkovich et al. | 423/659 |
| 7,077,643 B2 | 7/2006 | Holladay et al. | 431/215 |
| 7,084,180 B2 | 8/2006 | Wang et al. | 518/712 |
| 7,190,580 B2 | 3/2007 | Bezama et al. | 361/699 |
| 7,220,390 B2 | 5/2007 | Tonkovich et al. | 422/172 |
| 7,234,514 B2 | 6/2007 | Vogel | 165/170 |
| 7,250,074 B2 | 7/2007 | Tonkovich et al. | 95/130 |
| 7,255,845 B2 | 8/2007 | Tonkovich et al. | 423/437.2 |
| 7,641,890 B2 | 1/2010 | Nagasawa et al. | |
| 2003/0116503 A1 | 6/2003 | Wang et al. | 210/660 |
| 2003/0219903 A1 | 11/2003 | Wang et al. | 436/37 |
| 2004/0066703 A1 | 4/2004 | Sparey-Taylor et al. | 366/127 |
| 2004/0084795 A1 * | 5/2004 | Hornsby et al. | 264/41 |
| 2004/0220434 A1 | 11/2004 | Brophy et al. | 568/959 |
| 2004/0228882 A1 | 11/2004 | Qiu et al. | 424/400 |
| 2004/0229752 A1 | 11/2004 | Long et al. | 502/339 |
| 2004/0234566 A1 | 11/2004 | Qiu et al. | 424/401 |
| 2005/0032240 A1 | 2/2005 | Lee et al. | 436/180 |
| 2005/0087767 A1 | 4/2005 | Fitzgerald et al. | 257/200 |
| 2005/0176832 A1 | 8/2005 | Tonkovich et al. | 518/726 |
| 2006/0016215 A1 | 1/2006 | Tonkovich et al. | 62/617 |
| 2006/0016216 A1 | 1/2006 | Tonkovich et al. | 62/617 |
| 2006/0019333 A1 | 1/2006 | Rodgers et al. | 435/41 |
| 2006/0036106 A1 | 2/2006 | Mazanec et al. | 549/533 |
| 2006/0073080 A1 | 4/2006 | Tonkovich et al. | 422/100 |
| 2006/0102519 A1 | 5/2006 | Tonkovich et al. | 208/107 |
| 2006/0120213 A1 | 6/2006 | Tonkovich et al. | 366/144 |
| 2006/0129015 A1 | 6/2006 | Tonkovich et al. | 585/709 |
| 2006/0249020 A1 | 11/2006 | Tonkovich et al. | 95/115 |
| 2006/0275185 A1 | 12/2006 | Tonkovich et al. | 422/130 |
| 2006/0289662 A1 | 12/2006 | Dessiatoun | 237/1 |
| 2007/0004810 A1 | 1/2007 | Wang et al. | 518/718 |
| 2007/0085227 A1 | 4/2007 | Tonkovich et al. | 261/127 |

FOREIGN PATENT DOCUMENTS

| | | |
|---|---|---|
| DE | 3926466 | 2/1991 |
| DE | 199 20 794 A1 | 6/1999 |
| EP | 1102628 | 11/2006 |
| GB | 1531134 | 11/1978 |
| GB | 2077136 | 12/1981 |
| WO | 9421372 | 9/1994 |
| WO | 9700442 | 1/1997 |
| WO | 9828073 | 7/1998 |
| WO | 9838147 | 9/1998 |
| WO | 9916542 | 4/1999 |
| WO | 0006301 | 2/2000 |
| WO | 03006149 | 1/2003 |
| WO | 03/099429 A1 | 12/2003 |
| WO | 2004/103539 A2 | 2/2004 |
| WO | 2006/057895 A2 | 1/2006 |
| WO | 2006039568 | 4/2006 |
| WO | 2006/061524 A1 | 6/2006 |
| ZA | 855317 | 7/1985 |

OTHER PUBLICATIONS

Bennett et al ; "Microchannel cooled heatsinks for high average power laser diode arrays"; SPIE, vol. 1865; 1993; pp. 144-153.

Iglesia; "Design, synthesis, and use of cobalt-based Fischer-Tropsch synthesis catalysts"; Applied Catalysis A: General 161 (1997); pp. 59-78.

Chen et al.; "Performance analysis of a folding flow micromixer"; Microfluid Nanofluid (2009) 6:763-774.

MacInnes et al.; "Investigation of alternating-flow mixing in microchannels"; Chemical Engineering Science 60; 2005; pp. 3453-3467.

MacInnes et al.; "Numerial characterization of floding flow microchannel mixers"; Chemical Engineering Science 62; 2007; pp. 2718-2727.

MacInnes et al.; "Mixing Strategies for Flow in Microchannel Devices"; Chemical and Process Engineering, University of Sheffield, Nov. 24, 2004.

Iwasaki et al.; "Radical Polymerization Using Microflow System: Numbering-up of Microreactors and Continuous Operation"; *Organic Process Research & Development;* 2006, 10, 1126-1131.

Hessel et al.; Polymerisationen in mikro-strukturierten Reaktoren: Ein Uberblick; *Chemie Ingenieur Technik,* 2005, 77, No. 11.

Roberts et al.; "New measurements of the flow-curves for Carbopol dispersions without slip artefacts"; *Rheol Acta,* 2001, 40: 449-503.

Balaji et al.; "Improved Design of Microchannel Plate Geometry for Uniform Flow Distribution"; *The Canadian Journal of Chemical Engineering;* vol. 84, Dec. 2006, pp. 715-721.

Bergles et al.; "On the Nature of Critical Heat Flux in Microchannels"; *Journal of Heat Transfer,* Jan. 2005, vol. 127; pp. 101-107.

Cho et al.; "Two-Phase Flow Distribution and Pressure Drop in Microchannel Tubes Under Non-Heating and Heating Conditions"; *Nanoscale and Microscale Thermophysical Engineering,* 10: 233-247, 2006.

Commenge et al.; "Optimal Design for Flow Uniformity in Microchannel Reactors"; *AIChE Journal,* Feb. 2002, vol. 48, No. 2, pp. 345-358.

Griffini et al.; "Effect of Microchannel Plate Design on Fluid Flow Uniformity at Low Flow Rates"; *Chem. Eng. Technol.;* 2007, 30, No. 3, pp. 395-406.

Jousse et al.; "Compact model for multi-phase liquid-liquid flows in micro-fluidic devices"; *Lab Chip,* 2005, 5, pp. 646-656.

Delsman et al.; "Microchannel Plate Geometry Optimization for Even Flow Distribution at High Flow Rates"; *Trans IchemE,* Part A, *Chemical Engineering Research and Design,* 2004, 82(A2): 267-273.

Mas et al.; "Scalable Microfabricated Multiphase Reactors for Direct Fluorination Reactions"; Transducers '03, The 12th International Conference on Solid State Sensors, Actuators and Microsystems, Jun. 8-12, 2003, 2E64.P, pp. 655-658.

Lee et al.; "Gas flow in a microdevice with a mixing layer configuration"; *J. Micromech. Microeng.;* 12 (2002) 96-102.

Rebrov et al.; "Header Design for Flow Equalization in Microstructured Reactors"; *AIChE Journal;* Jan. 2007, vol. 53, No. 1, pp. 28-38.

Takagi et al.; "Continuous particle separation in a microchannel having asymemetrically arranged multiple branches"; *Lab Chip;* 2005, 5, 778-784.

Pochlauer et al.; "Large-Scale Application of Microreaction Technology Within Chemical Production of DSM"; DSM Fine Chemicals, http://isic2.epfl.ch/webdav/site/lcbp/shared/Renken/workshop/presentations/7-Poechlauer.pdf; 12 pages.

International Search Report and Written Opinion of the International Searching Authority, Application No. PCT/US2007/067060, mailed Oct. 19, 2007.

International Preliminary Report on Patentability, Application No. PCT/US2007/067060, mailed Aug. 5, 2008.

Kandlikar; "Exploring Roughness Effect on Laminar Internal Flow—Are We Ready for Change?"; Nanoscale and Microscale Thermophysical Engineering; 2008; pp. 61-82; vol. 12; Taylor & Francis Group, LLC.

Notification of Reasons for Refusal, Japanese Patent Application No. 2009-506787, mailed Aug. 30, 2011.

Office Action dated Dec. 12, 2011, EP Application 07 760 995.6-2104.

Chinese Office Action, Application No. 200780023303.3, issued Aug. 25, 2011.

* cited by examiner

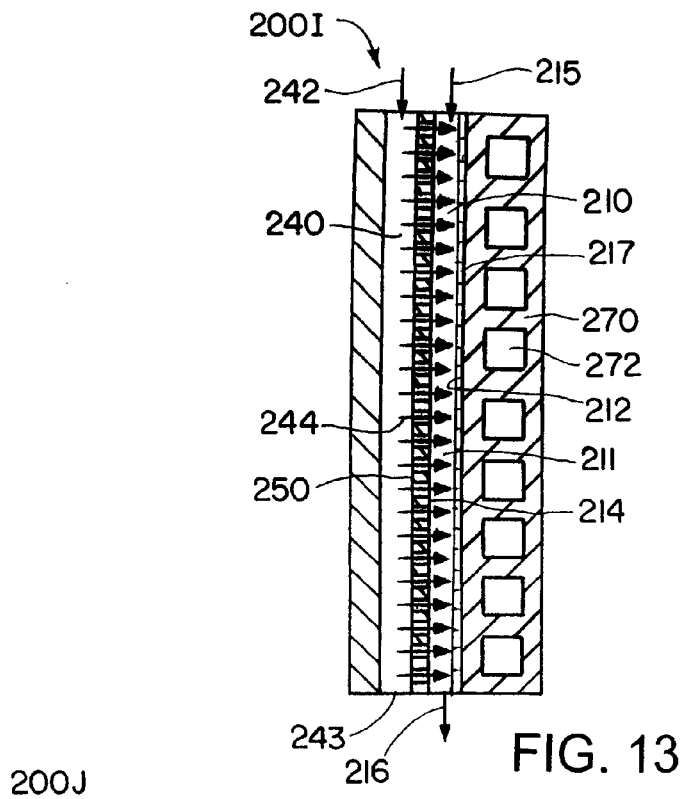
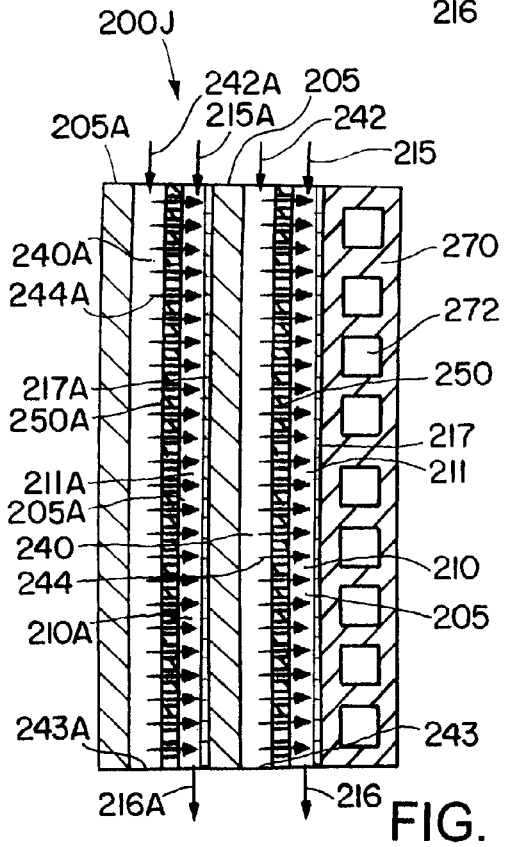
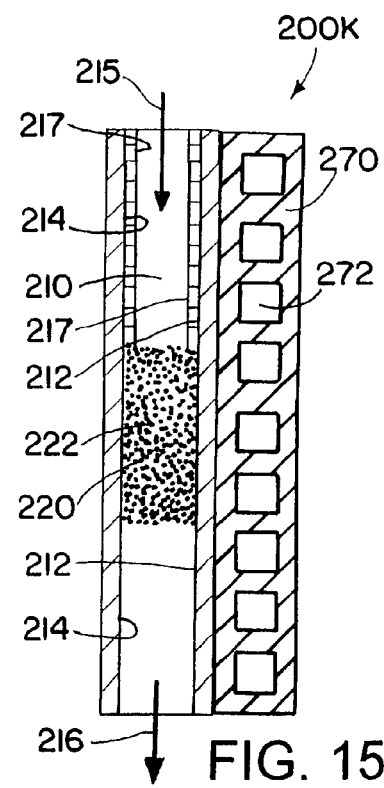
FIG. 13
FIG. 14
FIG. 15

Formed layer by tailoring

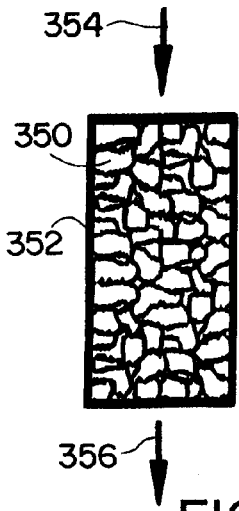 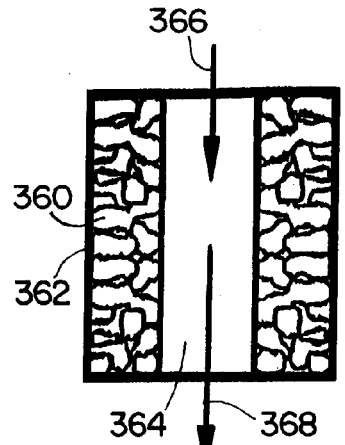 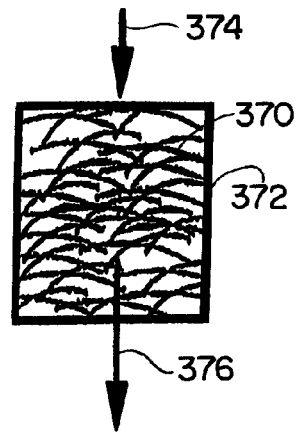
FIG. 35   FIG. 36   FIG. 37
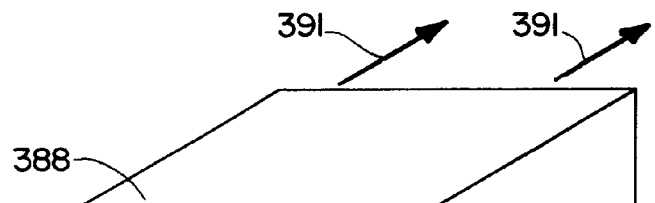
FIG. 38
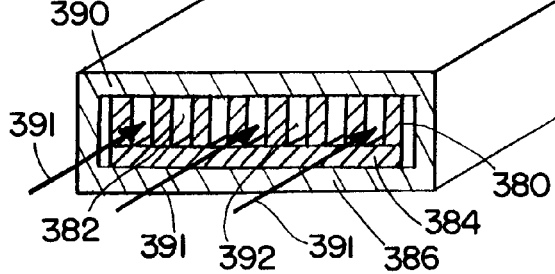 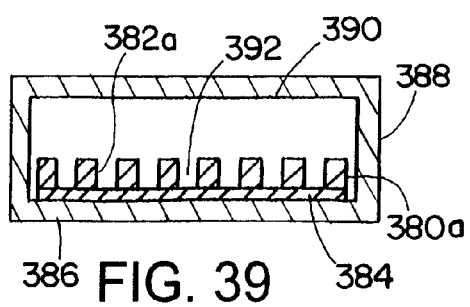
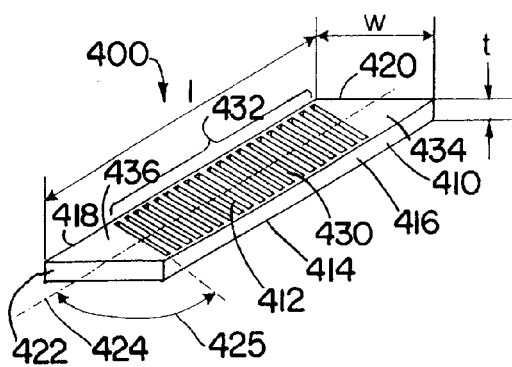 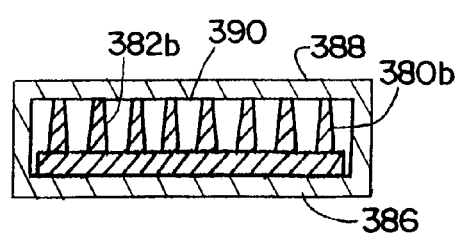
FIG. 41   FIG. 40   FIG. 39

PROCESS FOR TREATING AND/OR FORMING A NON-NEWTONIAN FLUID USING MICROCHANNEL PROCESS TECHNOLOGY

This application is a continuation of U.S. application Ser. No. 11/737,955 filed Apr. 20, 2007 now U.S. Pat. No. 8,048,383. This application claims priority under 35 U.S.C. §119(e) to U.S. Provisional Application Ser. No. 60/793,519 filed Apr. 20, 2006. The disclosures in these prior applications are incorporated herein by reference.

TECHNICAL FIELD

This invention relates to a process for treating and/or forming a non-Newtonian fluid using microchannel process technology.

BACKGROUND

Non-Newtonian fluids are liquids that exhibit viscosities that vary with changing shear stress or shear rate. Non-Newtonian fluids may comprise polymers, polymer solutions, emulsions, multiphase fluid mixtures, and the like. These non-Newtonian fluids may be useful as pharmaceuticals, adhesives, food products, personal care products, coating compositions, and the like. A problem with treating non-Newtonian fluids in microchannels relates to the fact that when the non-Newtonian fluids flow at high flow rates, high velocity gradients at the walls of the microchannels are created. This leads to high apparent viscosities and high pressure drops within the microchannels. This invention, in at least one embodiment, provides a solution to this problem.

SUMMARY

This invention relates to a process, comprising: conducting unit operations in at least two process zones in a process microchannel to treat and/or form a non-Newtonian fluid, a different unit operation being conducted in each process zone; and applying an effective amount of shear stress to the non-Newtonian fluid to reduce the viscosity of the non-Newtonian fluid in each process zone, the average shear rate in one process zone differing from the average shear rate in another process zone by a factor of at least about 1.2. The shear rate in at least one process zone may be is in excess of about 100 sec$^{-1}$, and in one embodiment in excess of about 1000 sec$^{-1}$.

The process microchannel may have a converging cross-sectional area in at least one process zone, and the shear stress may be applied to the non-Newtonian fluid by flowing the non-Newtonian fluid through the converging cross-sectional area.

The process microchannel may comprise surface features on and/or in one or more interior surfaces in at least one process zone, and the shear stress may be applied to the non-Newtonian fluid by flowing the non-Newtonian fluid in contact with the surface features.

The process microchannel may comprise one or more interior structured walls in at least one process zone, and the shear stress may be applied to the non-Newtonian fluid by flowing the non-Newtonian fluid in contact with one or more structured walls.

The process microchannel may comprise one or more internal obstructions in at least one process zone, and the shear stress may be applied to the non-Newtonian fluid by flowing the non-Newtonian fluid in contact with one or more internal obstructions.

The process microchannel may comprise a coating layer comprising voids and/or protrusions on one or more of its interior surfaces in at least one process zone, and the shear stress may be applied to the non-Newtonian fluid by flowing the non-Newtonian fluid in contact with the coating layer.

The unit operation in each process zone may comprise a chemical reaction, chemical separation, condensation, vaporization, heating, cooling, compression, expansion, phase separation, mixing, or a combination of two or more thereof.

The same unit operation may occur in the two or more process zones. However, the channel geometry may be different to allow for a more optimized shear stress environment for the process fluid.

The unit operation in each process zone may comprise heating the non-Newtonian fluid, cooling the non-Newtonian fluid, forming the non-Newtonian fluid by mixing two or more fluids, contacting and/or mixing the non-Newtonian fluid with one or more other fluids and/or particulate solids, conducting a reaction using two or more fluids to form a non-Newtonian fluid, conducting a reaction using as the reactant one or more non-Newtonian fluids, compressing the non-Newtonian fluid, expanding the non-Newtonian fluid, condensing the non-Newtonian fluid, vaporizing the non-Newtonian fluid, separating one or more components from the non-Newtonian fluid, or a combination of two or more thereof.

The viscosity of the non-Newtonian in at least one process zone fluid may be reduced to a viscosity up to about 10$^5$ centipoise during the inventive process.

BRIEF DESCRIPTION OF THE DRAWINGS

In the annexed drawings, like parts and features have like references. A number of the drawings are schematic illustrations which may not be accurately proportional.

(FIG. 7 shows two adjacent process microchannels, and the heat exchange channels are adjacent to and in thermal contact with one of the process microchannels and in thermal contact with the other process microchannel.) The process microchannels comprise internal surface features and/or converging cross-sectional areas for applying shear stress to the non-Newtonian fluid. These repeating units may be used to exchange heat with the non-Newtonian fluid. They may be used to conduct a chemical reaction using a homogeneous catalyst, the non-Newtonian fluid being a reactant and/or product.

FIG. 13 is a schematic illustration of a microchannel repeating unit that may be used in the microchannel processing unit illustrated in FIG. 3. The repeating unit comprises a process microchannel, a staged addition channel, an apertured section positioned between the process microchannel and the staged addition channel, and heat exchange channels. This repeating unit may be used for mixing an emulsion or multiphase fluid mixture, or for conducting a chemical reaction using a homogeneous catalyst.

FIG. 14 is a schematic illustration of an alternate embodiment of the microchannel repeating unit illustrated in FIG. 13 wherein a first repeating section and a second repeating section are positioned adjacent to one another, the first repeating section comprising a first process microchannel, a first staged addition channel and a first apertured section, the second repeating section comprising a second process microchannel, second staged addition channel and second apertured section. Heat exchange channels are adjacent to and in thermal contact with the first repeating section and in thermal contact with the second repeating section.

FIG. 15 is a schematic illustration of a repeating unit comprising a process microchannel and adjacent heat exchange channels. This repeating unit may be used in the microchannel processing unit illustrated in FIG. 3. The process microchannel contains a reaction zone comprising a catalyst. The interior walls of the process microchannel upstream of the catalyst comprise surface features for applying shear stress to the non-Newtonian fluid. The catalyst illustrated in FIG. 15 is in the form of a bed of particulate solids. However, any of the catalyst forms discussed in the specification may be used in the process microchannel illustrated in FIG. 15.

FIG. 35 is a schematic illustration of the reaction zone of a process microchannel that may be used with the inventive process, the reaction zone comprising a catalyst having a packed bed configuration.

FIG. 36 is a schematic illustration of the reaction zone of a process microchannel that may be used with the inventive process, the reaction zone comprising a catalyst having a flow-by configuration.

FIG. 37 is a schematic illustration of the reaction zone of a process microchannel that may be used with the inventive process, the reaction zone comprising a catalyst having a flow-through configuration.

FIG. 38 is a schematic illustration of a process microchannel that may be used in the inventive process, the process microchannel containing a fin assembly comprising a plurality of fins, a catalyst being supported by the fins.

FIG. 39 is a schematic illustration of an alternate embodiment of the process microchannel and fin assembly illustrated in FIG. 38.

FIG. 40 is a schematic illustration of an another alternate embodiment of the process microchannel and fin assembly illustrated in FIG. 38.

FIG. 41 is a schematic illustration of a microgrooved support strip that may be used to support a catalyst for use with the inventive process, the support strip comprising a top surface, a bottom surface, a front edge, back edge and side edges. The microgrooves are formed in the top surface. The microgrooves may penetrate part way or all the way through the support strip. Penetration of the microgrooves all the way through the support strip may permit fluid to flow through the microgrooves in the direction from the top surface to the bottom surface, or vice versa.

FIG. 43(b) is a cross-sectional view of the process microchannel illustrated in FIG. 43(a) taken along line (b)-(b) of FIG. 43(a).

DETAILED DESCRIPTION

All ranges and ratio limits disclosed in the specification may be combined. It is to be understood that unless specifically stated otherwise, references to "a," "an," and/or "the" may include one or more than one and that reference to an item in the singular may also include the item in the plural.

Figure 1:
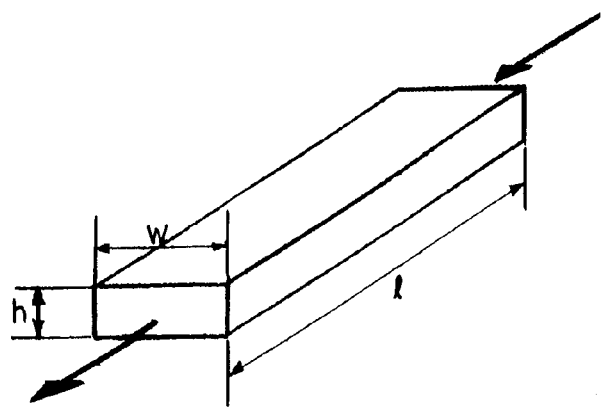
FIG. 1 is a schematic illustration of a microchannel that may be useful in the inventive process.

The term "microchannel" may refer to a channel having at least one internal dimension of height or width of up to about 10 millimeters (mm), and in one embodiment up to about 5 mm, and in one embodiment up to about 2 mm, and in one embodiment up to about 1 mm. The microchannel may comprise at least one inlet and at least one outlet wherein the at least one inlet is distinct from the at least one outlet. The microchannel may not be merely an orifice. The microchannel may not be merely a channel through a zeolite or a mesoporous material. An example of a microchannel that may be used with the inventive process is illustrated in FIG. 1. Referring to FIG. 1, the illustrated microchannel has a height (h), width (w) and length (l), or in the opposite direction. Fluid may flow through the microchannel in the direction indicated by the arrows. Both the height (h) and width (w) are perpendicular to the bulk flow direction of fluid in the microchannel. The height may be referred to as a gap. The height (h) or width (w) of the microchannel may be in the range of about 0.05 to about 10 mm, and in one embodiment from about 0.05 to about 5 mm, and in one embodiment from about 0.05 to about 2 mm, and in one embodiment from about 0.05 to about 1.5 mm, and in one embodiment from about 0.05 to about 1 mm, and in one embodiment from about 0.05 to about 0.75 mm, and in one embodiment from about 0.05 to about 0.5 mm. The other dimension of height (h) or width (w) may be of any dimension, for example, up to about 3 meters, and in one embodiment about 0.01 to about 3 meters, and in one embodiment about 0.1 to about 3 meters. The length (l) of the microchannel may be of any dimension, for example, up to about 10 meters, and in one embodiment from about 0.1 to about 10 meters, and in one embodiment from about 0.2 to about 10 meters, and in one embodiment from about 0.2 to about 6 meters, and in one embodiment from 0.2 to about 3 meters. Although the microchannel illustrated in FIG. 1 has a cross section that is rectangular, it is to be understood that the microchannel may have a cross section having any shape, for example, a square, circle, semi-circle, trapezoid, etc. The shape and/or size of the cross section of the microchannel may vary over its length. For example, the height or width may taper from a relatively large dimension to a relatively small dimension, or vice versa, over the length of the microchannel. This is illustrated in FIG. 2.

Figure 2:
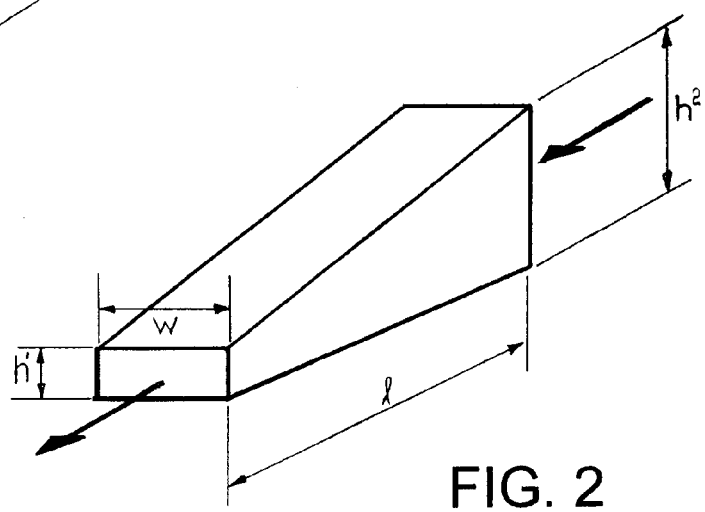
FIG. 2 is a schematic illustration of an alternate embodiment of a microchannel that may be useful in the inventive process. This microchannel may be referred to as having a converging cross-sectional area.

The microchannel illustrated in FIG. 2 may be an alternate embodiment of the microchannel illustrated in FIG. 1. The microchannel illustrated in FIG. 2 has a cross-sectional area that varies from a maximum to a minimum. The minimum cross-sectional area may be at the outlet to the microchannel and the maximum cross-sectional area may be at the inlet. This microchannel may be referred to as having a "narrowing cross-section." This microchannel may be referred to as a microchannel with a "converging cross-sectional area." The microchannel illustrated in FIG. 2 may be referred to as a trapezoid microchannel. The microchannel has two dimensions of height, one being a minimum dimension ($h^1$) and the other being a maximum dimension ($h^2$). The height increases gradually from $h^1$ to $h^2$. Alternatively, the microchannel may have a cross-section in the shape of a circle, oval, triangle, etc. The microchannel has at least one dimension of height ($h^1$) that may be in the range of about 0.05 to about 10 mm, and in one embodiment from about 0.05 to about 5 mm, and in one embodiment from about 0.05 to about 2 mm, and in one embodiment from about 0.05 to about 1.5 mm, and in one embodiment from about 0.05 to about 1 mm, and in one embodiment from about 0.05 to about 0.75 mm, and in one embodiment from about 0.05 to about 0.5 mm. The width (w) may be of any dimension, for example, up to about 3 meters, and in one embodiment about 0.01 to about 3 meters, and in one embodiment about 0.1 to about 3 meters. The length (l) may be of any dimension, for example, up to about 10 meters, and in one embodiment from about 0.1 to about 10 meters, and in one embodiment from about 0.2 to about 6 meters. The maximum cross-sectional may be at least about two-times (2×) the minimum cross-sectional area, and in one embodiment at least about 5-times (5×), and in one embodiment at least about 20-times (20×) the minimum cross-sectional area. The linear velocity (or local contact time between reactants and catalyst) of fluid flowing in this microchannel may be increased as the fluid flows along the linear flow path in the microchannel in the direction indicated in FIG. 2. A non-Newtonian fluid flowing in this microchannel in the direction indicated by the arrows may undergo increased shear resulting in a reduction in viscosity. WO 03/099429 A1 is incorporated herein by reference for its disclosure of microchannels with varying cross-sectional areas.

The term "unit operation" may refer to a process and/or apparatus wherein a chemical reaction, chemical separation (including absorption, adsorption, distillation, extraction), condensation, vaporization, distillation, heating, cooling, compression, expansion, phase separation, mixing, or a combination of two or more thereof, is conducted.

The term "microchannel processing unit" may refer to an apparatus comprising at least one process microchannel wherein a non-Newtonian fluid is processed. The processing of the non-Newtonian fluid may comprise conducting one or more unit operations. This may comprise heating the fluid, cooling the fluid, forming the fluid by mixing two or more fluids (which may or may not be non-Newtonian fluids), contacting the fluid with another fluid (which may or may not be a non-Newtonian fluid), conducting a reaction using one or more non-Newtonian fluids as a reactant, forming a non-Newtonian fluid by reacting one or more fluids (which may or may not be non-Newtonian fluids), separating one or more components of the non-Newtonian fluid from the non-Newtonian fluid, or a combination of two or more of the foregoing. The microchannel processing unit may comprise a plurality of the process microchannels that may be operated in parallel, a header or manifold assembly for providing for the flow of fluid into the process microchannels, and a footer or manifold assembly providing for the flow of fluid out of the process microchannels. The microchannel processing unit may comprise one or more staged addition channels, for example staged addition microchannels, positioned adjacent to one or more of the process microchannels. The microchannel processing unit may comprise one or more heat exchange channels, for example heat exchange microchannels, adjacent to and/or in thermal contact with the process microchannels for cooling and/or heating the contents of the process microchannels.

The term "process microchannel" may refer to a microchannel wherein a process is conducted. The process may relate to any of the unit operations disclosed above.

The term "process zone" may refer to a section within a process microchannel wherein one or more unit operations are conducted.

The term "microchannel reactor" may refer to an apparatus comprising one or more process microchannels for conducting a reaction. The microchannel reactor may comprise a plurality of the process microchannels that may be operated in parallel, a header or manifold assembly for providing for the flow of fluid into the process microchannels, and a footer or manifold assembly providing for the flow of fluid out of the process microchannels. The microchannel reactor may comprise one or more staged addition channels, for example staged addition microchannels, positioned adjacent to one or more of the process microchannels. The microchannel reactor may comprise one or more heat exchange channels, for example heat exchange microchannels, adjacent to and/or in thermal contact with the process microchannels for cooling and/or heating the contents of the process microchannels.

The term "structured wall" or "SW" may refer to an interior channel wall, for example, a microchannel wall, with one or more strips or shims positioned or mounted on its surface. The strips or shims may contain one or more void spaces, openings or through holes. See, for example, FIGS. 48-49. These may be referred to as surface features. Two or more layers of the strips or shims may be stacked one above another or positioned side by side to provide a porous structure positioned or mounted on the channel wall. A catalyst may be supported by the structured wall. An open bulk flow region or gap may be positioned in the process microchannel adjacent the structured wall.

The term "structured wall reactor" may refer to a microchannel reactor comprising at least one process microchannel wherein the process microchannel contains one or more structured walls. A catalyst may be supported by the one or more structured walls. An open bulk flow region or gap may be positioned in the process microchannel adjacent the structured wall.

The term "volume" with respect to volume within a process microchannel may include all volume in the process microchannel a process fluid may flow through or flow by. This volume may include the volume within microgrooves of a microgrooved support that may be positioned in the process microchannel and adapted for the flow of fluid in a flow-through manner or in a flow-by manner. This volume may include volume within surface features that may be positioned in the process microchannel and adapted for the flow of fluid in a flow-through manner or in a flow-by manner.

The term "shim" may refer to a planar or substantially planar sheet or plate. The thickness of the shim may be the smallest dimension of the shim and may be up to about 2 mm, and in one embodiment in the range from about 0.05 to about 2 mm, and in one embodiment in the range of about 0.05 to about 1 mm, and in one embodiment in the range from about 0.05 to about 0.5 mm. The shim may have any length and width.

Figure 46:
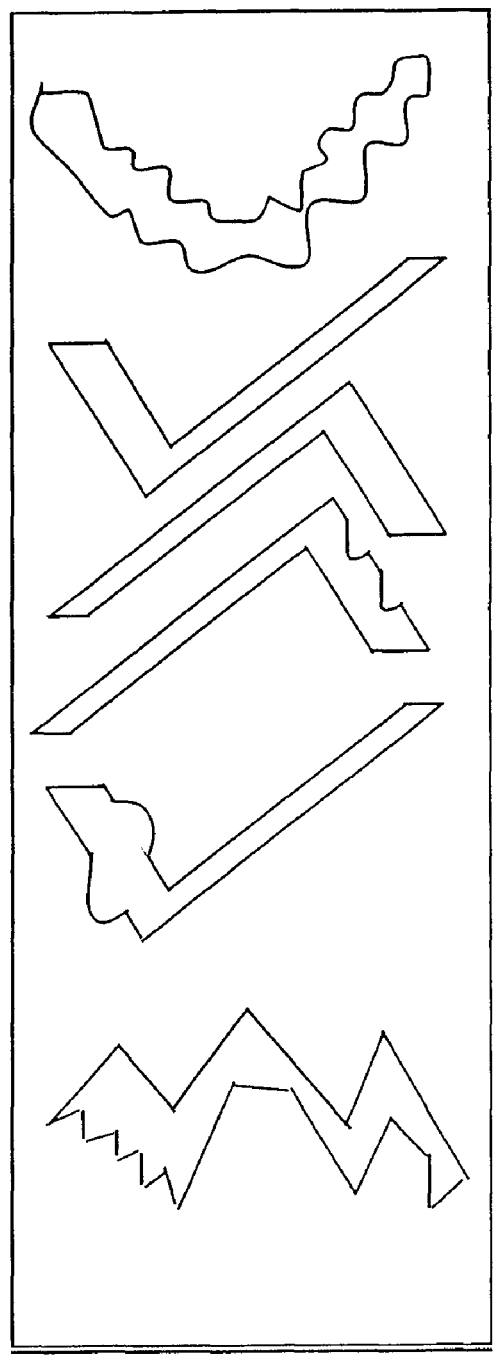
FIGS. 46 and 47 are schematic illustrations of surface features that may be used in the microchannels used with the inventive process.
Figure 47:
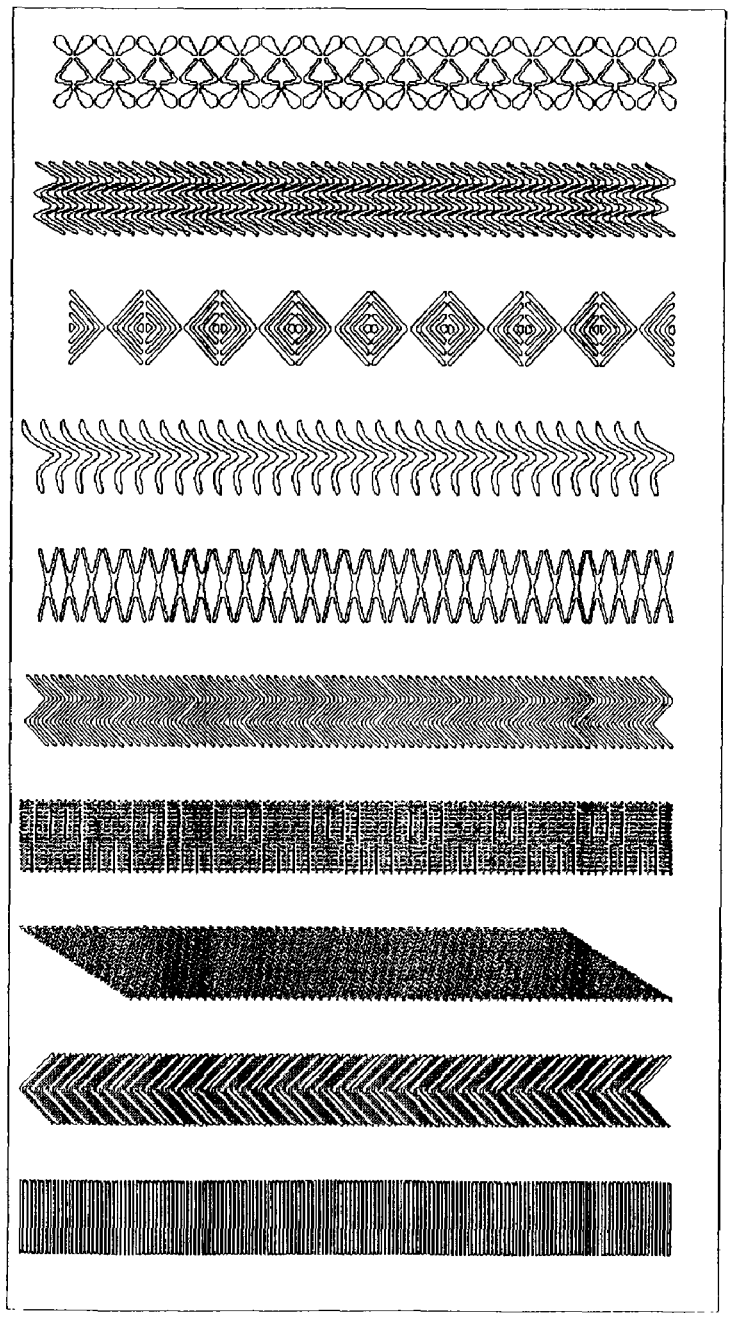

The term "surface feature" may refer to a depression in a microchannel wall and/or a projection from a microchannel wall that modifies flow and/or mixing within the microchannel. The surface features may be in the form of circles, spheres, frustrums, oblongs, squares, rectangles, angled rectangles, checks, chevrons, vanes, air foils, wavy shapes, and the like. The surface features may contain subfeatures where the major walls of the surface features further contain smaller surface features that may take the form of notches, waves, indents, holes, burrs, checks, scallops, and the like. The surface features may have a depth, a width, and for non-circular surface features a length. Examples are illustrated in FIGS. 46-47. The surface features may be formed on or in one or more of the interior walls of the process microchannels used in accordance with the invention. The surface features may be formed on or in one or more of the interior walls of the heat exchange channels employed herein. The surface features may be referred to as passive surface features or passive mixing features. The surface features may be used to disrupt laminar flow streamlines and create advective flow at an angle to the bulk flow direction. This may enhance contact between fluid components or between fluid components and catalyst. The surface features may comprise voids and/or protrusions formed in a structured wall, see, for example, FIGS. 48-49.

The term "microgroove" may refer to a groove in a substrate having a depth of up to about 1000 microns, and in one embodiment in the range from about 1 to about 1000 microns, and in one embodiment in the range from about 1 to about 500 microns, and in one embodiment from about 1 to about 100 microns. The microgrooves may penetrate all the way through the substrate over part or all of the length of the microgrooves. The microgrooves may penetrate only partially through the substrate. The depth of the microgrooves may be measured at the deepest point of penetration into the substrate. The microgrooves may have a width up to about 1000 microns, and in one embodiment in the range from about 0.1 to about 1000 microns, and in one embodiment in the range from about 1 to about 500 microns. The width may be the width measured at the widest point of the microgroove. The microgroove may have any length, for example, up to about 100 cm, and in one embodiment from about 0.1 to about 100 cm, and in one embodiment from about 0.1 to about 10 cm. The microgroove may have a cross section of any shape. Examples include square, rectangle, vee, semi-circle, dovetail, trapezoid, and the like. The shape and/or size of the cross section of the microgroove may vary over the length of the microgroove.

The term "adjacent" when referring to the position of one channel relative to the position of another channel may mean directly adjacent such that a wall separates the two channels. This wall may vary in thickness. However, "adjacent" channels may not be separated by an intervening channel that would interfere with heat transfer between the channels.

The term "thermal contact" may refer to two bodies, for example channels, that are not necessarily in contact with each other or adjacent to each other but still may exchange heat with each other. Thus, for example, one body in thermal contact with another body may heat or cool the other body.

The term "bulk flow region" may refer to open areas within a process microchannel. A contiguous bulk flow region may allow rapid fluid flow through a process microchannel without significant pressure drops. In one embodiment there may be laminar flow in the bulk flow region. A bulk flow region may comprise at least about 5%, and in one embodiment from about 30 to about 80% of the internal volume of a process microchannel or the cross-sectional area of the process microchannel.

The term "bulk flow direction" may refer to the vector through which fluid may travel in an open path in a channel.

The term "residence time," which may also be referred to as the "average residence time," may be the internal volume of a channel occupied by a fluid flowing through the channel divided by the average volumetric flowrate for the fluid flowing through the channel at the temperature and pressure being used.

The terms "upstream" and "downstream" may refer to positions within a channel (e.g., a process microchannel) that is relative to the direction of flow of a fluid stream in the channel. For example, a position within the channel not yet reached by a portion of a fluid stream flowing toward that position would be downstream of that portion of the fluid stream. A position within the channel already passed by a portion of a fluid stream flowing away from that position would be upstream of that portion of the fluid stream. The terms "upstream" and "downstream" do not necessarily refer to a vertical position since the channels used herein may be oriented horizontally, vertically or at an inclined angle.

The terms "standard cubic feet" or "standard cubic meters" may refer to volumes measured at a temperature of 20° C. and atmospheric pressure.

The term "normal liters" may refer to volumes measured at a temperature of 20° C. and atmospheric pressure.

The term "gauge pressure" may refer to absolute pressure, less atmospheric pressure. For example, a gauge pressure of zero atmospheres corresponds to atmospheric pressure. However, throughout the text and in the appended claims, unless otherwise indicated, all pressures are absolute pressures.

The term "cycle" may refer to a single pass of reactants through the process microchannels.

The term "ml (milliliter) per gram of catalyst per hour" may refer to a volume (ml) of product produced per gram of catalyst per hour wherein the gram of catalyst refers to catalytic material in the catalyst but not any support that may be present.

The term "yield" may refer to moles of reactant converted to a specific product divided by the number of moles of reactant converted. The yield may be calculated by multiplying the conversion of the reactant by the selectivity to the product in question.

The term "superficial velocity" for the velocity of a fluid flowing in a channel may refer to the volumetric flow rate at standard pressure and temperature divided by the open cross sectional area of the channel.

The term "immiscible" may refer to one liquid not being soluble in another liquid or only being soluble to the extent of up to about 1 milliliter per liter at 25° C.

The term "water insoluble" may refer to a material that is insoluble in water at 25° C., or soluble in water at 25° C. up to a concentration of about 0.1 gram per liter.

The term "fluid" may refer to a gas, a liquid, a gas or a liquid containing dispersed solids, a gas containing liquid droplets, a liquid containing gas bubbles, a gas containing liquid droplets and dispersed solids, or a liquid containing gas bubbles and dispersed solids.

The term "multiphase mixture" may refer to a composition containing two or more phases. The multiphase mixture may comprise a continuous liquid phase with one or more discontinuous liquid, gas and/or solid phases (eg., solid particulates) dispersed in the continuous liquid phase. The multiphase mixture may be an emulsion.

The term "emulsion" may refer to a composition containing a continuous liquid phase and one or more discontinuous liquid phases dispersed in the continuous liquid phase. The emulsion may include one or more gas and/or solid phases dispersed in one or more of the liquid phases.

The term "heat source" may refer to a substance or device that gives off heat and may be used to heat another substance or device. The heat source may be in the form of a heat exchange channel having a heat exchange fluid in it that transfers heat to another substance or device; the another substance or device being, for example, a channel that is adjacent to or in thermal contact with the heat exchange channel. The heat exchange fluid may be in the heat exchange channel and/or it may flow through the heat exchange channel. The heat source may be in the form of a heating element, for example, an electric heating element or a resistance heater.

The term "heat sink" may refer to a substance or device that absorbs heat and may be used to cool another substance or device. The heat sink may be in the form of a heat exchange channel having a heat exchange fluid in it that receives heat transferred from another substance or device; the another substance or device being, for example, a channel that is adjacent to or in thermal contact with the heat exchange channel. The heat exchange fluid may be in the heat exchange channel and/or it may flow through the heat exchange channel. The heat sink may be in the form of a cooling element, for example, a non-fluid cooling element.

The term "heat source and/or heat sink" may refer to a substance or a device that may give off heat or absorb heat. The heat source and/or heat sink may be in the form of a heat exchange channel having a heat exchange fluid in it that transfers heat to another substance or device adjacent to or in thermal contact with the heat exchange channel when the another substance or device is to be heated, or receives heat transferred from the another substance or device adjacent to or in thermal contact with the heat exchange channel when the another substance or device is to be cooled. The heat exchange channel functioning as a heat source and/or heat sink may function as a heating channel at times and a cooling channel at other times. A part or parts of the heat exchange channel may function as a heating channel while another part or parts of the heat exchange channel may function as a cooling channel.

The term "heat exchange channel" may refer to a channel having a heat exchange fluid in it that may give off heat and/or absorb heat. The heat exchange channel may be a microchannel.

The term "heat transfer wall" may refer to a common wall between a process microchannel and an adjacent heat exchange channel where heat transfers from one channel to the other through the common wall.

The term "heat exchange fluid" may refer to a fluid that may give off heat and/or absorb heat.

The term "adjacent" when referring to the position of one channel relative to the position of another channel may mean directly adjacent such that a wall separates the two channels.

This wall may vary in thickness. However, "adjacent" channels may not be separated by an intervening channel that would interfere with heat transfer between the channels.

The term "thermal contact" may refer to two bodies, for example channels, that are not necessarily in contact with each other or adjacent to each other but still may exchange heat with each other. Thus, for example, one body in thermal contact with another body may heat or cool the other body.

The term "residence time," which may also be referred to as the "average residence time," may be the internal volume of a channel occupied by a fluid flowing through the channel divided by the average volumetric flowrate for the fluid flowing through the channel at the temperature and pressure being used.

The term "graded catalyst" may refer to a catalyst with one or more gradients of catalytic activity. The graded catalyst may have a varying concentration or surface area of a catalytically active metal. The graded catalyst may have a varying turnover rate of catalytically active sites. The graded catalyst may have physical properties and/or a form that varies as a function of distance. For example, the graded catalyst may have an active metal concentration that is relatively low at the entrance to a process microchannel and increases to a higher concentration near the exit of the process microchannel, or vice versa; or a lower concentration of catalytically active metal nearer the center (i.e., midpoint) of a process microchannel and a higher concentration nearer a process microchannel wall, or vice versa, etc. The thermal conductivity of a graded catalyst may vary from one location to another within a process microchannel. The surface area of a graded catalyst may be varied by varying size of catalytically active metal sites on a constant surface area support, or by varying the surface area of the support such as by varying support type or particle size. A graded catalyst may have a porous support where the surface area to volume ratio of the support is higher or lower in different parts of the process microchannel followed by the application of the same catalyst coating everywhere. A combination of two or more of the preceding embodiments may be used. The graded catalyst may have a single catalytic component or multiple catalytic components (for example, a bimetallic or trimetallic catalyst). The graded catalyst may change its properties and/or composition gradually as a function of distance from one location to another within a process microchannel. The graded catalyst may comprise rimmed particles that have "eggshell" distributions of catalytically active metal within each particle. The graded catalyst may be graded in the axial direction along the length of a process microchannel or in the lateral direction. The graded catalyst may have different catalyst compositions, different loadings and/or numbers of active catalytic sites that may vary from one position to another position within a process microchannel. The number of catalytically active sites may be changed by altering the porosity of the catalyst structure. This may be accomplished using a washcoating process that deposits varying amounts of catalytic material. An example may be the use of different porous catalyst thicknesses along the process microchannel length, whereby a thicker porous structure may be left where more activity is required. A change in porosity for a fixed or variable porous catalyst thickness may also be used. A first pore size may be used adjacent to an open area or gap for flow and at least one second pore size may be used adjacent to the process microchannel wall.

The term "hydrocarbon" may refer to purely hydrocarbon compounds; that is, aliphatic compounds, (e.g., alkane or alkylene), alicyclic compounds (e.g., cycloalkane, cycloalkylene), aromatic compounds, aliphatic- and alicyclic-substituted aromatic compounds, aromatic-substituted aliphatic compounds, aromatic-substituted alicyclic compounds, and the like. Examples may include methane, ethane, ethylene, propane, propylene, cyclohexane, ethyl cyclohexane, toluene, the xylenes, ethyl benzene, styrene, etc. The term "hydrocarbon" may refer to substituted hydrocarbon compounds; that is, hydrocarbon compounds containing non-hydrocarbon substituents. Examples of the non-hydrocarbon substituents may include hydroxyl, acyl, nitro, etc. The term "hydrocarbon" may refer to hetero substituted hydrocarbon compounds; that is, hydrocarbon compounds which contain atoms other than carbon in a chain or ring otherwise comprising carbon atoms. Examples of hetero atoms may include, for example, nitrogen, oxygen and sulfur. In one embodiment, no more than about three, and in one embodiment no more than about one, substituents or hetero atoms may be present for each 10 carbon atoms in the hydrocarbon compound.

The term "mm" may refer to millimeter. The term "nm" may refer to nanometer. The term "ms" may refer to millisecond. The term "μm" may refer to micron or micrometer. The terms "micron" and "micrometer" have the same meaning and may be used interchangeably.

The non-Newtonian fluid treated and/or formed in the inventive process may comprise any fluid polymer or polymer composition (e.g., polymer solution) that exhibits non-Newtonian properties. The non-Newtonian fluid may comprise one or more polymers or a polymer solution. The non-Newtonian fluid may comprise one or more molten polymers. The polymer may be combined with an aqueous or an organic solvent or dispersing medium. The non-Newtonian fluid may comprise a multiphase mixture or an emulsion which exhibits non-Newtonian properties. The multiphase mixture or emulsion may comprise one or more polymers. The solutions, multiphase mixtures and/or emulsions may comprise aqueous compositions.

The polymer may comprise one or more homopolymers, copolymers, terpolymers, and the like. The polymer may comprise repeating units derived from one or more polymerizable monomers including olefins (eg., ethylene, propylene, isobutylene, and the like), cyclic olefins, dienes (eg., butadiene, isoprene, chloroprene), ethers, esters, amides, carbonates, acetates, acrylics, alkylacrylics, acrylates, alkylacrylates (eg., methyl acrylate, methyl methacrylate), vinyl acetate, styrene, vinyls (eg., vinyl chloride), vinylidenes (eg., vinylidene chloride, vinylidene fluoride), acrylonitrite, cyanoacrylates (eg., methylcyanoacrylate), tetrafluoroethylene, and combinations of two or more thereof. The polymer may comprise one or more thermoplastic resins.

The polymer may comprise one or more of polyethylene, polypropylene, polystyrene, rubber modified polystyrene, styrene-butadiene copolymers, vinyl polymers and copolymers, acrylonitrile-butadiene-styrene (ABS) copolymers, polymethylmethacrylate, polycarbonate, and the like.

The polymer may comprise one or more copolymers, terpolymers, and the like, derived from ethylene and/or propylene, and one or more functional monomers, for example, alkylacrylate, acrylic acid, alkylacrylic acid, vinyl acetate, and the like. Examples of these may include ethylene/vinyl acetate copolymers; ethylene/methyl acrylate copolymers; ethylene/ethylacrylate copolymers; ethylene/butyl acrylate copolymers; ethylene/methacrylic acid copolymers; ethylene/acrylic acid copolymers; ethylene/methacrylic acid copolymers containing sodium or zinc (also referred to as ionomers); acid-, anhydride- or acrylate-modified ethylene/vinyl acetate copolymers; acid- or anhydride-modified ethylene/acrylate copolymers; anhydride-modified polyethylenes; and mixtures of two or more thereof.

The polymer may comprise one or more natural rubbers, reclaimed rubbers, synthetic rubbers, and the like. The polymer may comprise one or more polyisoprenes, polychloroprenes, styrene butadiene rubbers, tackified natural or synethetic rubbers, styrene butadiene or styrene isoprene block copolymers, random copolymers of ethylene and vinyl acetate, ethylene-vinyl-acrylic terpolymers, polyisobutylenes, poly(vinyl ethers), poly(acrylic) esters, and the like.

The polymer may comprise one or more homopolymers or copolymers of acrylic acid crosslinked with one or more polyakenyl polyethers. These may be available from Noveon under the tradename Carbopol.

The non-Newtonian fluid that may be treated and/or formed using the inventive process may comprise any multiphase fluid mixture that exhibits non-Newtonian properties. The multiphase fluid mixture may be an emulsion. The multiphase fluid mixture may comprise two or more liquids which may be immiscible relative to each other. A third liquid, which may be immiscible relative to either or both of the other liquids, may be included. Each liquid may be organic, aqueous, or a combination thereof. For example, one liquid may comprise benzene and the other liquid may comprise glycerol. One of the liquids may be an ionic liquid (e.g., a salt of 1-butyl-3-methylimidazolium) while another may be an organic liquid. One of the liquids may comprise water, and another liquid may comprise a hydrophobic organic liquid such as an oil. The multiphase fluid mixture may comprise a water-in-oil (w/o) or oil-in-water (o/w) emulsion. The multiphase fluid mixture may comprise a double emulsion, for example, a water-in-oil-in-water (w/o/w) or an oil-in-water-in-oil (o/w/o) emulsions. The term "oil" may be used to refer to an organic phase of a multiphase fluid mixture although the organic material may or may not be an oil. One of the liquids may be present in the multiphase fluid mixture at a concentration in the range from about 0.1 to about 99.9% by weight, and in one embodiment about 1 to about 99% by weight, and in one embodiment about 5 to about 95% by weight, with the other liquid making up the difference. The third liquid, when used, may be present in the multiphase fluid mixture at a concentration in the range up to about 50% by weight, and in one embodiment from about 0.1 to about 20% by weight, and in one embodiment about 0.5 to about 10% by weight.

One or more of the liquids in the multiphase fluid mixture may comprise one or more liquid hydrocarbons. These may comprise natural oils, synthetic oils, or mixtures thereof. The natural oils may include animal oils and vegetable oils (e.g., castor oil, lard oil) as well as mineral oils. The natural oils may include oils derived from coal or shale. The oil may be a saponifiable oil from the family of triglycerides, for example, soybean oil, sesame seed oil, cottonseed oil, safflower oil, and the like. The oil may be a silicone oil. The oil may be an aliphatic or naphthenic hydrocarbon such as Vaseline, squalane, squalene, or one or more dialkyl cyclohexanes, or a mixture of two or more thereof. Synthetic oils may include hydrocarbon oils such as polymerized and interpolymerized olefins (e.g., polybutylenes, polypropylenes, propylene isobutylene copolymers, etc.); poly(1-hexenes), poly-(1-octenes), poly(1-decenes), etc. and mixtures thereof; alkylbenzenes (e.g., dodecylbenzenes, tetradecylbenzenes, dinonylbenzenes, di-(2-ethylhexyl)benzenes, etc.); polyphenyls (e.g., biphenyls, terphenyls, alkylated polyphenyls, etc.); alkylated diphenyl ethers and alkylated diphenyl sulfides and the derivatives, analogs and homologs thereof and the like. Alkylene oxide polymers and interpolymers and derivatives thereof where the terminal hydroxyl groups have been modified by esterification, etherification, etc., are synthetic oils that may be used. The synthetic oil may comprise a poly-alpha-olefin or a Fischer-Tropsch synthesized hydrocarbon. The oil may comprise a normally liquid hydrocarbon fuel, for example, a distillate fuel such as motor gasoline as defined by ASTM Specification D439, or diesel fuel or fuel oil as defined by ASTM Specification D396.

The multiphase fluid mixture may comprise one or more fatty alcohols, fatty acid esters, or mixtures thereof. The fatty alcohol may be a Guerbet alcohol. The fatty alcohol may contain from about 6 to about 22 carbon atoms, and in one embodiment about 6 to about 18 carbon atoms, and in one embodiment about 8 to about 12 carbon atoms. The fatty acid ester may be an ester of a linear fatty acid of about 6 to about 22 carbon atoms with linear or branched fatty alcohol of about 6 to about 22 carbon atoms, an ester of a branched carboxylic acid of about 6 to about 13 carbon atoms with a linear or branched fatty alcohol of about 6 to about 22 carbon atoms, or a mixture thereof. Examples include myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. The fatty acid ester may comprise: an ester of alkyl hydroxycarboxylic acid of about 18 to about 38 carbon atoms with a linear or branched fatty alcohol of about 6 to about 22 carbon atoms (e.g., dioctyl malate); an ester of a linear or branched fatty acid of about 6 to about 22 carbon atoms with a polyhydric alcohol (for example, propylene glycol, dimer diol or trimer triol) and/or a Guerbet alcohol; a triglyceride based on one or more fatty acids of about 6 to about 18 carbon atoms; a mixture of mono-, di- and/or triglycerides based on one or more fatty acids of about 6 to about 18 carbon atoms; an ester of one or more fatty alcohols and/or Guerbet alcohols of about 6 to about 22 carbon atoms with one or more aromatic carboxylic acids (e.g., benzoic acid); an ester of one or more dicarboxylic acids of 2 to about 12 carbon atoms with one or more linear or branched alcohols containing 1 to about 22 carbon atoms, or one or more polyols containing 2 to about 10 carbon atoms and 2 to about 6 hydroxyl groups, or a mixture of such alcohols and polyols; an ester of one or more dicarboxylic acids of 2 to about 12 carbon atoms (e.g., phthalic acid) with one or more alcohols of 1 to about 22 carbon atoms (e.g., butyl alcohol, hexyl alcohol); an ester of benzoic acid with linear and/or branched alcohol of about 6 to about 22 carbon atoms; or mixture of two or more thereof.

The multiphase fluid mixture may comprise: one or more branched primary alcohols of about 6 to about 22 carbon atoms; one or more linear and/or branched fatty alcohol carbonates of about 6 to about 22 carbon atoms; one or more Guerbet carbonates based on one or more fatty alcohols of about 6 to about 22 carbon atoms; one or more dialkyl (e.g., diethylhexyl) naphthalates wherein each alkyl group contains 1 to about 12 carbon atoms; one or more linear or branched, symmetrical or nonsymmetrical dialkyl ethers containing about 6 to about 22 carbon atoms per alkyl group; one or more ring opening products of epoxidized fatty acid esters of about 6 to about 22 carbon atoms with polyols containing 2 to about 10 carbon atoms and 2 to about 6 hydroxyl groups; or a mixture of two or more thereof.

The multiphase fluid mixture may comprise water in one or more phases. The water may be taken from any convenient source. The water may be deionized or purified using osmosis or distillation.

The multiphase fluid mixture may comprise one or more emulsifiers and/or surfactants. The emulsifiers and/or surfactants may comprise ionic or nonionic compounds having a hydrophilic lipophilic balance (HLB) in the range of zero to about 18 in Griffin's system, and in one embodiment about 0.01 to about 18. The ionic compounds may be cationic or amphoteric compounds. Examples include those disclosed in *McCutcheons Surfactants and Detergents,* 1998, North American & International Edition. Pages 1-235 of the North American Edition and pages 1-199 of the International Edition are incorporated herein by reference for their disclosure of such emulsifiers. The emulsifiers and/or surfactants that may be used include alkanolamines (eg., triethanolamine), alkylarylsulfonates, amine oxides, poly(oxyalkylene) compounds, including block copolymers comprising alkylene oxide repeat units, carboxylated alcohol ethoxylates, ethoxylated alcohols, ethoxylated alkyl phenols, ethoxylated amines and amides, ethoxylated fatty acids, ethoxylated fatty esters and oils, fatty esters, fatty acid amides, glycerol esters, glycol esters, sorbitan esters, imidazoline derivatives, lecithin and derivatives, lignin and derivatives, monoglycerides and derivatives, olefin sulfonates, phosphate esters and derivatives, propoxylated and ethoxylated fatty acids or alcohols or alkyl phenols, sorbitan derivatives, sucrose esters and derivatives, sulfates or alcohols or ethoxylated alcohols or fatty esters, sulfonates of dodecyl and tridecyl benzenes or condensed naphthalenes or petroleum, sulfosuccinates and derivatives, and tridecyl and dodecyl benzene sulfonic acids. The emulsifiers and/or surfactants may comprise: one or more polyalkylene glycols; one or more partial esters of glycerol or sorbitan and fatty acids containing about 12 to about 22 carbon atoms; or a mixture thereof. The emulsifier and/or surfactant may comprise a pharmaceutically acceptable material such as lecithin. The concentration of these emulsifiers and/or surfactants in the emulsions may range up to about 20% by weight of the emulsion, and in one embodiment in the range from about 0.01 to about 5% by weight, and in one embodiment from about 0.01 to about 2% by weight. In one embodiment, the concentration may be up to about 2% by weight, and in one embodiment up to about 1% by weight, and in one embodiment up to about 0.5% by weight.

The multiphase fluid mixture may contain one or more additional functional additives. These functional additives may be premixed with any of the liquids used to form the multiphase mixture or emulsion. These functional additives may include: UV protection factors (e.g., 3-benzylidene camphor and derivatives thereof, 4-aminobenzoic acid derivatives, esters of salicylic acid, derivatives of benzophenone, esters of benzalmalonic acid, triazine derivatives, 2-phenyl-benzimidazole-5-sulfonic acid and salts thereof, sulfonic acid derivatives of benzophenone and salts thereof, derivatives of benzoyl methane); waxes (e.g., candelilla wax, carnauba wax, Japan wax, cork wax, rice oil wax, sugar cane wax, beeswax, petrolatum, polyalkylene waxes, polyethylene glycol waxes); consistency factors (e.g., fatty alcohols, hydroxy fatty alcohols; partial glycerides, fatty acids, hydroxy fatty acids); thickeners (e.g., polysaccharides such as xanthan gum, guar-guar and carboxymethyl cellulose, polyethylene glycol monoesters and diesters, polyacrylates, polyacrylamides, polyvinyl alcohol, polyvinyl pyrrolidone); superfatting agents (e.g., lanolin, lecithin, polyol fatty acid esters, monoglycerides, fatty acid alkanolamides); stabilizers (e.g., metal salts of fatty acids, such as magnesium, aluminum or zinc stearate or ricinoleate); polymers (e.g., catonic polymers such as cationic cellulose derivatives, cationic starch, copolymers of diallyl ammonium salts and acrylamides, quaternized vinyl pyrrolidone/vinyl imidazole polymers, polyethyene-imine, cationic silicone polymers, polyaminopolyamides; anionic, zwitterionic, amphoteric and nonionic polymers); silicone compounds (e.g., dimethyl polysiloxanes; methyl phenyl polysiloxanes; cyclic silicones; amino-, fatty acid-, alcohol-, polyether-, epoxy-, fluorine-, glycoside- and/or alkyl-modified silicone compounds; simethicones; dimethicones); fats; waxes; lecithins; phospholipids; biogenic agents (e.g., tocopherol, ascorbic acid, deoxyribonucleic acid, retinol, amino acids, plant extracts, vitamin complexes); antioxidants (e.g., amino acids, imidazoles, peptides, carotinoids, carotenes, liponic acid and derivatives thereof, aurothioglucose, propylthiouracil, dilaurylthiodipropionate, sulfoximine compounds, metal chelators such as alpha-hydroxy fatty acids, alpha-hydroxy acids such as citric or lactic acid, humic acid, bile acid, EDTA, EGTA, folic acid and derivatives thereof, vitamin complexes such as vitamins A, C or E, stilbenes and derivatives thereof); deodorants; antiperspirants; antidandruff agents; swelling agents (e.g., montmorillonites, clay minerals); insect repellents; self-tanning agents (e.g., dihydroxyacetone); tyrosine inhibitors (depigmenting agents); hydrotropes (e.g., ethanol, isopropyl alcohol, and polyols such as glycerol and alkylene glycols used to improve flow behavior); solubilizers; preservatives (e.g., phenoxy-ethanol, formaldehyde solution, parabens, pentane diol, sorbic acid), perfume oils (e.g., extracts of blossoms, fruit peel, roots, woods, herbs and grasses, needles and branches, resins and balsams, and synthetic perfumes including esters, ethers, aldehydes, ketones, alcohols and hydrocarbons); dyes; and the like. The concentration of each of these additives in the multiphase fluid mixture may be up to about 20% by weight, and in one embodiment from about 0.01 to about 10% by weight, and in one embodiment about 0.01 to about 5% by weight, and in one embodiment about 0.01 to about 2% by weight, and in one embodiment about 0.01 to about 1% by weight. The multiphase fluid mixture may contain one or more particulate solids.

The particulate solids may be organic, inorganic, or a combination thereof. The particulate solids may comprise catalysts (e.g., combustion catalysts such as $CeO_2/BaAl_{12}O_{19}$, $Pt/Al_2O_3$, etc., polymerization catalysts, and the like), pigments (e.g., $TiO_2$, carbon black, iron oxides, etc.), fillers (e.g., mica, silica, talcum, barium sulfate, polyethylenes, polytetrafluoroethylene, nylon powder, methyl methacrylate powder), etc. The particulate solids may comprise nanosize particles. The particulate solids may have a mean particle diameter in the range of about 0.001 to about 10 microns, and in one embodiment about 0.01 to about 1 micron. The concentration of the particulate solids in the multiphase fluid mixture may range up to about 70% by weight, and in one embodiment from about 0.1 to about 30% by weight based on the weight of the emulsion.

The multiphase fluid mixture may comprise one or more discontinuous phases dispersed in a continuous phase. The discontinuous phase may comprise gas bubbles, liquid droplets and/or particulate solids having a volume-based mean diameter of up to about 200 microns, and in one embodiment about 0.01 to about 200 microns, and in one embodiment about 0.01 to about 100 microns, and in one embodiment about 0.01 to about 50 microns, and in one embodiment about 0.01 to about 25 microns, and in one embodiment about 0.01 to about 10 microns, and in one embodiment about 0.01 to about 5 microns, and in one embodiment about 0.01 to about 2 microns, and in one embodiment about 0.01 to about 1 micron, and in one embodiment about 0.01 to about 0.5 micron, and in one embodiment about 0.01 to about 0.2 micron, and in one embodiment about 0.01 to about 0.1 micron, and in one embodiment about 0.01 to about 0.08 micron, and in one embodiment about 0.01 to about 0.05 micron, and in one embodiment about 0.01 to about 0.03 micron.

The discontinuous phase may comprise water and the continuous phase may comprise an organic liquid. The discontinuous phase may comprise an organic liquid and the continuous phase may comprise water or another organic liquid. The continuous phase may contain particulate solids dispersed or suspended in the continuous phase. The discontinuous phase may contain gas bubbles, particulate solids and/or droplets encapsulated within droplets in the discontinuous phase. An advantage of the invention is that at least in one embodiment the gas bubbles, liquid droplets and/or particulate solids may be characterized by having a relatively narrow distribution of bubble, droplet or particulate sizes. In one embodiment, the bubble, droplet or particulate sizes in the dispersed phase may be plotted with the result being a normal distribution curve.

"Relative span" is often referred to as "span." It is a dimensionless parameter calculated from volume distribution. As with volume median droplet size (VMD), D[v,0.1] and D[v, 0.9] are diameters representing the points at which 10% and 90%, respectively, of the volume of liquid dispersed is in droplets of smaller diameter. The span may be defined as D[v,0.9] minus D[v,0.1] which is then divided by the VMD (D[v,0.5]). The span for the bubbles, droplets or particulates may be in the range from about 0.005 to about 10, and in one embodiment about 0.01 to about 10, and in one embodiment about 0.01 to about 5, and in one embodiment about 0.01 to about 2, and in one embodiment about 0.01 to about 1, and in one embodiment about 0.01 to about 0.5, and in one embodiment about 0.01 to about 0.2, and in one embodiment about 0.01 to about 0.1. In one embodiment, the inventive process may be conducted in a single process microchannel and the span may be in the range of from about 0.01 to about 0.5. In one embodiment, the inventive process may be conducted in a scaled-up process employing multiple process microchannels and the span may be in the range from about 0.01 to about 1.

In one embodiment, the volume-based diameter for the gas bubbles, liquid droplets and/or solid particulates may be in the range from about 0.01 to about 200 microns, and the span may be in the range from about 0.005 to about 10. In one embodiment, the volume-based mean diameter may be in the range from about 0.01 to about 100 microns, and the span may be in the range from about 0.01 to about 5. In one embodiment, the volume-based mean diameter may be in the range from about 0.01 to about 50 microns, and the span may be in the range from about 0.02 to about 5. In one embodiment, the volume-based mean diameter may be in the range from about 0.01 to about 10 microns, and the span may be in the range from about 0.05 to about 2.5. In one embodiment, the volume-based mean diameter may be in the range from about 0.01 to about 5 microns, and the span may be in the range from about 0.01 to about 2. In one embodiment, the volume-based mean diameter may be in the range of about 0.01 to about 1 micron, and the span may be in the range of about 0.005 to about 1.

Multiphase fluid mixtures treated and/or formed in accordance with the inventive process may provide the advantage of enabling the manufacturer to supply the multiphase fluid mixtures in concentrate form, thus enabling the end user to add additional ingredients, such as water or oil, to obtain the final fully formulated product.

The multiphase fluid mixtures treated and/or formed by the inventive process may have numerous applications. These may include personal skin care products wherein reduced concentrations of emulsifiers or surfactants are desirable (e.g., waterproof sun screen, waterproof hand creams or lotions).

The multiphase fluid mixtures treated and/or formed by the inventive process may be useful as paints or coatings. These may include water-resistant latex paints with strong weatherability characteristics. The multiphase fluid mixtures may be useful as adhesives, glues, caulks, waterproof sealants, and the like. The inclusion of an aqueous phase in these compositions may reduce the problem of volatile organic compounds (VOC) in these products.

The inventive process may be used in various food processing applications, particularly continuous processing operations.

The inventive process may be used in the treatment and/or production of agricultural chemicals where the use of a dispersed phase with a narrow distribution of droplet sizes is advantageous for spreading the chemicals on leafs, and providing enhanced waterproofing with smaller concentrations of chemicals. The inventive process may be used in the treatment and/or production of agricultural chemicals such as pesticides wherein it may be desired to employ a droplet size for the dispersed phase that is smaller than the wavelength of visible light.

The inventive process may be used for the treatment and/or production of emulsified lubricants and fuels. These may include on-board fuel emulsification systems such as those that may be used for diesel engines.

The inventive process may be used in emulsion polymerization processes. For example, it may be possible to solubilize monomers in a surfactant with a catalyst.

The inventive process may be used to make rapid setting emulsions containing bitumen. These emulsions may be used as surface dressings for cement or asphalt surfaces such as roads, driveways, and the like. These emulsions may contain from about 60 to about 70% by weight bitumen and may be sprayed onto the surface being treated. Chippings may be spread on top of these surface dressings and rolled to ensure proper embedding and alignment. This may provide a water impervious surface seal and also an improved surface texture.

The multiphase fluid mixtures treated and/or made using the inventive process may comprise silicone emulsions. These emulsions may be used for treating fibers and other substrates to alter their water repellant properties.

The inventive process may be used in a crystallization process, for example, a continuous crystallization process. This process may be used to isolate, purify and/or produce powders of a specified size. An example of such crystals include highly refined sugar. In emulsion crystallization, a melt may be crystallized within droplets of the emulsion so that homogeneous nucleation may occur at a lower rate than in a bulk melt. This process may be conducted without solvents, and thus may provide the advantage of low capital and operating costs.

The inventive process may be used to treat and/or make liquid crystals. The liquid crystals formed in the process may help to reduce the use of emulsifiers and/or surfactants, as the dispersed phase may be "locked" in place.

The inventive process may be used to treat and/or make wax emulsions for adhesives, liquid soaps, laundry detergents, coatings for textiles or fabrics, and the like.

The inventive process may be used in the manufacture of pharmaceuticals wherein the provision of a dispersed oil phase with a narrow distribution of droplet sizes is advantageous. These may include oral or injectable compositions as well as dermatological creams, lotions and ophthalmics. The droplet size and distribution achieved with the inventive process may increase the efficacy of the drug and provide for reduced levels of use of the drug for required treatments. This also may provide the advantage of avoiding or limiting the use of non-aqueous solvent components which tend to solubilize organic substances used in packaging materials. The droplet size for the dispersed oil phase for these applications may be up to about 0.5 micron in order to avoid being eliminated by the spleen or liver, and in one embodiment in the range from about 0.01 to about 0.2 micron, and in one embodiment 0.01 to about 0.1 micron. The multiphase fluid mixtures treated or produced by the inventive process may function as emulsion vehicles for insoluble or poorly soluble drugs (e.g., ibuprofen, diazepam, griseofulvin, cyclosporin, cortisone, proleukin, etoposide, paclitaxel, cytotoxin, vitamin E, alpha-tocopherol, and the like). Many of the pharmaceutical compounds or drugs, oils and surfactants disclosed in U.S. Patent Application Publication No. 2003/0027858A1 may be used in making pharmaceutical compositions using the inventive process; this patent publication is incorporated herein by reference for its disclosure of such compounds or drugs, oils and surfactants. An advantage of using the inventive process relates to the fact that many of the problems associated with using conventional high-shear mixing equipment for attempting to achieve small droplets with a narrow droplet size distribution while maintaining a sterile environment may be avoided.

The invention relates to a process which employs one or more process microchannels, wherein each process microchannel has two or more process zones, and one or more different unit operations are conducted in each process zone. With each unit operation a non-Newtonian fluid is treated and/or formed.

The unit operation may comprise a chemical reaction, chemical separation (including sorption (i.e., absorption and/or adsorption), distillation, extraction), condensation, vaporization, heating, cooling, compression, expansion, phase separation, mixing, or a combination of two or more thereof. Thus, for example, the inventive process may comprise heating a non-Newtonian fluid in a first process zone and then conducting a chemical reaction with the non-Newtonian fluid in a second or subsequent process zone. The non-Newtonian fluid may be heated or cooled during the chemical reaction. The process may comprise mixing various ingredients in a first process zone to form the non-Newtonian fluid and then cooling the non-Newtonian fluid in a second or subsequent process zone.

The inventive process may be used to heat the non-Newtonian fluid, cool the non-Newtonian fluid, form the non-Newtonian fluid by mixing two or more fluids (which may or may not be non-Newtonian fluids), contact and/or mix the non-Newtonian fluid with one or more other fluids (which may or may not be a non-Newtonian fluid) and/or particulate solids, conduct a reaction using two or more fluids (which may or may not be non-Newtonian fluids) to form a non-Newtonian fluid, conduct a reaction using as the reactant one or more non-Newtonian fluids, compress the non-Newtonian fluid, expand the non-Newtonian fluid, condense the non-Newtonian fluid, vaporize the non-Newtonian fluid, separate one or more components from the non-Newtonian fluid, or a combination of two or more of the foregoing.

The inventive process includes applying shear stress to the non-Newtonian fluid that is sufficient to reduce the viscosity of the non-Newtonian fluid prior to and/or during each unit operation. Prior to conducting the inventive process the non-Newtonian fluid may have viscosity in the range from about $10^{-3}$ to about $10^8$ centipoise, and in one embodiment from about $10^2$ to about $10^5$ centipoise. The viscosity may be reduced in each process zone to a level in the range up to about $10^5$ centipoise, and in one embodiment in the range from about $10^{-5}$ to about $10^5$ centipoise, and in one embodiment from about $10^{-3}$ to about $10^3$ centipoise, and in one embodiment from about $10^{-3}$ to about 10 centipoise.

The shear rate in each process zone may be in excess of about 100 $\sec^{-1}$, and in one embodiment in excess of about 250 $\sec^{-1}$, and in one embodiment in excess of about 500 $\sec^{-1}$, and in one embodiment in excess of about 750 $\sec^{-1}$, and in one embodiment in excess of about 1000 $\sec^{-1}$, and in one embodiment in excess of about 2500 $\sec^{-1}$, and in one embodiment in excess of about 500 $\sec^{-1}$, and in one embodiment in excess of about 7500 $\sec^{-1}$, and in one embodiment in excess of about 10,000 $\sec^{-1}$, and in one embodiment in excess of about 50,000 $\sec^{-1}$, and in one embodiment in excess of about 100,000 $\sec^{-1}$. The average shear rate in one process zone may differ from the average shear rate in another process zone by a factor of at least about 1.2, and in one embodiment by a factor of at least about 1.5, and in one embodiment by a factor of at least about 2, and in one embodiment by a factor of at least about 3, and in one embodiment by a factor of at least about 4, and in one embodiment by a factor of at least about 5, and in one embodiment by a factor of at least about 7, and in one embodiment by a factor of at least about 10, and in one embodiment by a factor of at least about 20, and in one embodiment by a factor of at least about 30, and in one embodiment by a factor of at least about 40, and in one embodiment by a factor of at least about 50, and in one embodiment by a factor of at least about 75, and in one embodiment by a factor of at least about 100.

Figure 68:
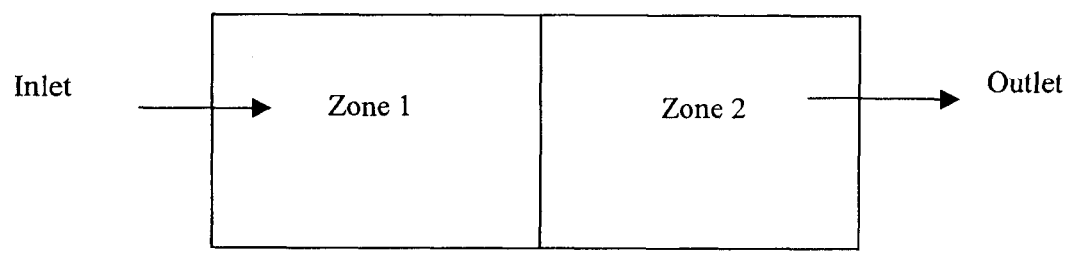
FIG. 68 is a schematic illustration of a process microchannel which has two process zones.
Figure 69:
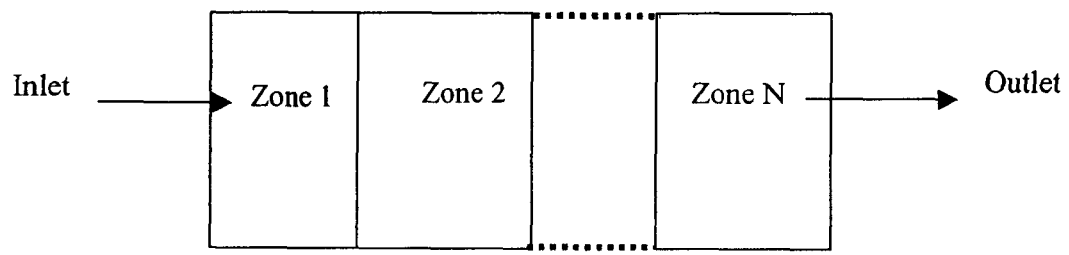
FIG. 69 is a schematic illustration of a process microchannel which has a plurality of process zones.

An advantage of the inventive process relates to utilizing the nature of non-Newtonian fluids and optimizing channel dimensions for different unit operations in the same process microchannel. FIG. 68 shows a process microchannel with separate process zones: process zone 1 and process zone 2. A first unit operation may be conducted in process zone 1 and a different unit operation may be conducted in process zone 2. The dependence of viscosity of the non-Newtonian fluid on shear rate may be used to select microchannel dimensions to maximize the process efficiency in each process zone. Similarly, FIG. 69 shows a process microchannel containing a plurality or "n" process zones. The value of n may be any number, for example from 3 to about 20, and in one embodiment from 3 to about 10, and in one embodiment from 3 to about 5.

The average shear rate, $\gamma_{avg}$, in a process zone may be determined by the following formula, wherein A is the wetted surface area in the process zone:

$$\gamma_{avg} = \frac{\int_{Wall\text{-}surface} \gamma dA}{\int_{wall\text{-}surface} dA}$$

The surface area A comprises the internal surface area of the process microchannel walls in the process zone including protrusions and/or voids (e.g., from surface features or a structured wall) on and/or in the process microchannel walls. The surface area, A, does not include catalyst or sorption material surfaces.

In one embodiment, the average shear rate in one process zone may be greater by a factor of at least about 1.2, than the average shear rate in at least about 25% of the process zones in the process microchannel. In one embodiment, the average shear rate in one process zone may be greater by a factor of at least about 1.2, than the average shear rate in at least about 50% of the process zones in the process microchannel.

Figure 3:
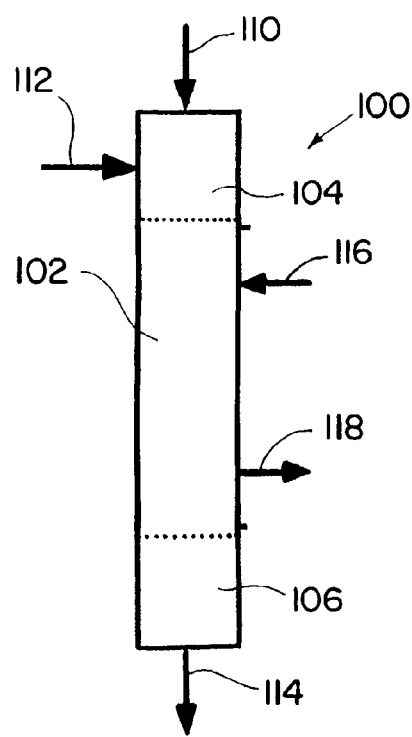
FIG. 3 is a schematic illustration of a microchannel processing unit that may be useful in treating a non-Newtonian fluid.

Referring to FIG. 3, the process may be conducted using microchannel processing unit 100 which includes microchannel processing unit core 102, process fluid header 104, and product footer 106. The microchannel processing unit core 102 may contain a plurality of process microchannels useful for conducting two or more unit operations for treating and/or forming a non-Newtonian fluid. The microchannel processing unit core 102 may optionally contain one or more staged addition channels adjacent to each process microchannel and/or one or more heat exchange channels. The staged addition channels and/or heat exchange channels may be microchannels. The process microchannels, and optionally staged addition channels and/or heat exchange channels may be stacked in layers, one above the other, or positioned side by side. The process header 104 may provide a passageway for a first fluid stream to flow into the process microchannels. The first fluid may be Newtonian or non-Newtonian. The first fluid stream may flow into the microchannel processing unit 100 through the header 104, as indicated by arrow 110. Optionally, a second fluid stream may flow into the microchannel processing unit 100 through the header 104, as indicated by arrow 112. Optionally, one or more additional fluid streams (not shown in FIG. 3) may also flow through the header 104 into the process microchannels. The second fluid and/or additional fluids may be Newtonian or non-Newtonian. The fluid streams may be mixed in the header 104 and flow into the process microchannels, or they may flow into the microchannel processing unit core 102 and be mixed in the process microchannels. Alternatively, the fluid streams may be mixed upstream of the header 104 and then flow through the header 104 into the process microchannels. The product footer 106 may provide a passageway for product to flow from the process microchannels. The product may be Newtonian or non-Newtonian. The product flows from the microchannel processing unit core 102 through the product footer 106, and out of product footer 106, as indicated by arrow 114. One or more of the first fluid stream, second fluid stream, additional fluid stream, fluid stream mixtures, and/or product comprises a non-Newtonian fluid. The product may be recycled back through the microchannel processing unit core 102 any number of times, for example, one, two, three, four times, etc. A heat exchange fluid may flow into the microchannel processing unit core 102, as indicated by arrow 116, through heat exchange channels in the microchannel processing unit core 102, and out of the microchannel processing unit core 102, as indicated by arrow 118. The microchannel processing unit 100 may be employed in conjunction with storage vessels, pumps, manifolds, valves, flow control devices, conduits, and the like, which are not shown in the drawings, but would be apparent to those skilled in the art.

The microchannel processing unit core 102 may comprise a plurality of microchannel processing units for conducting one or more unit operations with the non-Newtonian fluid. The microchannel processing unit core 102 may contain any number of these repeating units, for example, one, two, three, four, five, six, eight, ten, hundreds, thousands, etc. Examples of these are illustrated in FIGS. 4-26 and 42-43.

In one embodiment the process microchannel may have a converging cross-sectional area (see, FIG. 2, 8-12 or 19-22) in at least one process zone and the shear stress may be applied to the non-Newtonian fluid by flowing the non-Newtonian fluid through the converging cross-sectional area. In one embodiment, the process microchannel may comprise surface features (see, FIGS. 46-47) on and/or in one or more interior surfaces in at least one process zone, and the shear stress may be applied to the non-Newtonian fluid by flowing the non-Newtonian fluid in contact with the surface features. In one embodiment, the process microchannel may comprise one or more interior structured walls (see, FIGS. 48-49) in at least one process zone, and the shear stress may be applied to the non-Newtonian fluid by flowing the non-Newtonian fluid in contact with one or more structured walls. The voids and/or protrusions in the structured walls may be referred to as surface features. In one embodiment the process microchannels may comprise a coating layer containing voids and/or protrusions on one or more interior surfaces in at least one process zone, and the shear stress may be applied to the non-Newtonian fluid by flowing the non-Newtonian fluid in contact with the coating layer. In one embodiment, the process microchannel may comprise internal flow restriction devices (e.g., static mixers, monoliths, ribs, etc.) in at least one process zone and the shear stress may be applied to the non-Newtonian fluid by flowing the non-Newtonian fluid in contact with the flow restriction devices.

Figure 4:
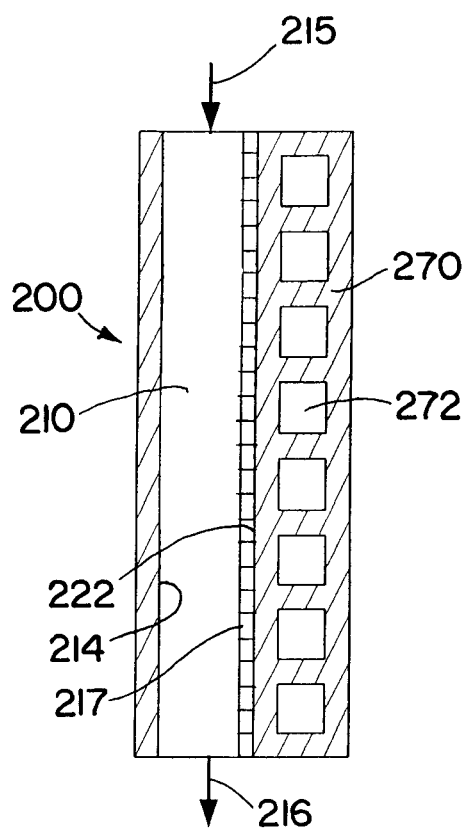
FIGS. 4-12 are schematic illustrations of microchannel repeating units that may be used in the microchannel processing unit illustrated in FIG. 3. These repeating units comprise a process microchannel and heat exchange channels, the heat exchange channels being adjacent to and in thermal contact with the process microchannels.

Referring to FIG. 4, repeating unit 200 comprises process microchannel 210 and heat exchange zone 270. The process microchannel 210 may contain two or more process zones. Heat exchange zone 270 comprises heat exchange channels 272. A process fluid flows in the process microchannel in the direction indicated by arrows 215 and 216. Heat exchange fluid flows in heat exchange channels 272 in a direction that is cross-current relative to the flow in the process microchannel 210. The heat exchange channels 272 may be used to provide a tailored heating or cooling profile along the length of the process microchannel 210. The process microchannel 210 includes opposite side walls 212 and 214. Sidewall 212 may be referred to as a heat transfer wall. Surface features 217 are positioned on and/or in sidewall 212. The process fluid may comprise the first fluid stream, or a mixture of the first fluid stream and second fluid stream and optionally one or more additional fluid streams. One or more of the fluid streams and/or the fluid mixture may be a non-Newtonian fluid. The process fluid flows from the process fluid header 104 into the process microchannel 210 as indicated by arrow 215. The flow of the fluid in the process microchannel and the contacting of the surface features 217 provide for the application of shear stress on the non-Newtonian fluid that is sufficient to reduce its viscosity. One or more unit operations is conducted with the non-Newtonian fluid in the process microchannel 210. The resulting product flows out of the process microchannel 210 as indicated by arrow 216. The product flows from the repeating unit 200 to and through the product footer 106. Heat exchange fluid flows in heat exchange channels 272 and exchanges heat with the process microchannel 210. The exchange of heat between the heat exchange channels 272 and process microchannel 210 may result in a cooling and/or heating of the process microchannel 210.

Figure 5:
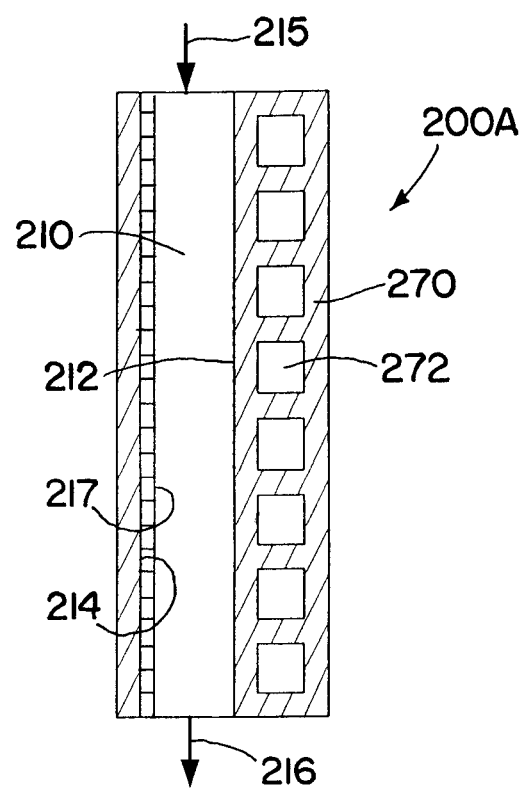

Repeating unit 200A illustrated in FIG. 5 is the same as repeating unit 200 illustrated in FIG. 4 with the exception that the surface features 217 are positioned on sidewall 214, rather than sidewall 212.

Figure 6:
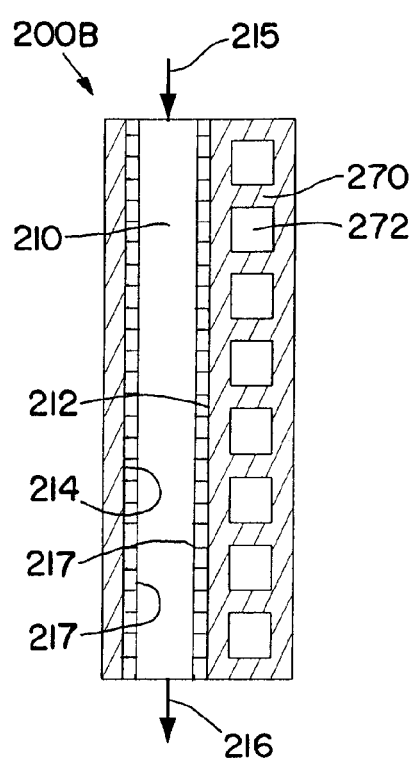

Repeating unit 200B illustrated in FIG. 6 is the same as repeating unit 200 illustrated in FIG. 4 with the exception that the surface features 217 are positioned on both sidewalls 212 and 214.

Figure 7:
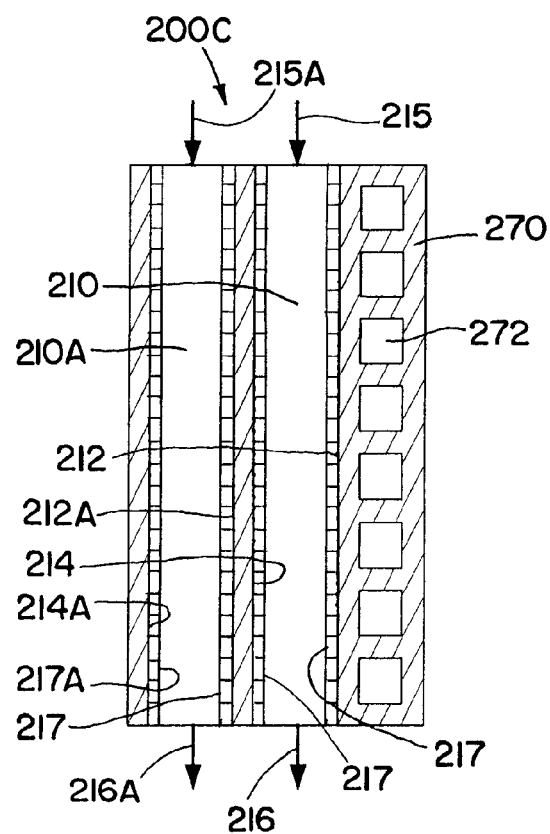

The microchannel repeating unit 200C illustrated in FIG. 7 is the same as repeating unit 200B illustrated in FIG. 6 with the exception that the repeating unit 200C includes two process microchannels 210 and 210A rather than one process microchannel. Repeating unit 200C comprises process microchannels 210 and 210A and heat exchange zone 270. In operation, the first fluid stream or a mixture of the first fluid stream and the second fluid stream (and optionally one or more additional fluid streams) flows into process microchannels 210 and 210A from process fluid header 104 as indicated by arrows 215 and 215A, respectively. One or more of the process fluids and/or the fluid mixture may be a non-Newtonian fluid. The process fluid contacts the surface features 217 and 217A as indicated above. This provides for the application of shear stress on the non-Newtonian fluid resulting in a reduction in viscosity. The process fluid flows in the process microchannels 210 and 210A. One or more unit operations are conducted in the process microchannels 210 and 210A. The resulting product exits the process microchannels 210 and 200A as indicated by arrows 216 and 216A. The product flows from the process microchannels 210 and 210A to and through the product footer 106 and out of the microchannel processing unit 100 as indicated by arrow 114. Heat exchange fluid flowing in the heat exchange channels 272 exchanges heat with the process fluids in the process microchannels 210 and 210A.

Figure 8:
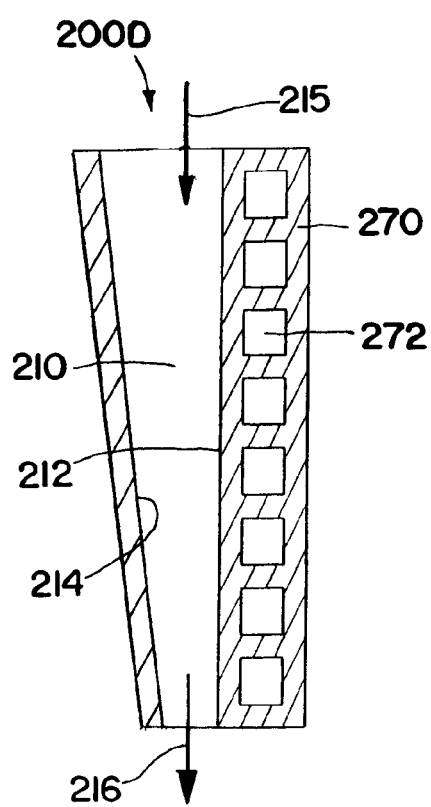

The repeating unit 200D illustrated in FIG. 8 is the same as the repeating unit 200 illustrated in FIG. 4 with the exception that process microchannel 210 in repeating unit 200D has a converging cross-sectional area. The cross-sectional area at the entrance of the process microchannel 210 near the arrow 215 is larger than the cross-sectional area at the outlet of the process microchannel 210 near the arrow 216. The repeating unit 200D is also different than the repeating unit 200 by virtue of the fact that the surface features in the repeating unit 200 have been excluded in the repeating unit 200D. In operation, shear stress is applied to the non-Newtonian fluid in the process microchannel 210 by flowing the non-Newtonian fluid through the converging cross-sectional area. As the fluid flows through the process microchannel 210, the velocity of the fluid increases. The viscosity of the non-Newtonian fluid decreases. The pressure drop of the fluid flowing in the process microchannel 210 decreases. One or more unit operations are conducted in the process microchannel 210.

Figure 9:
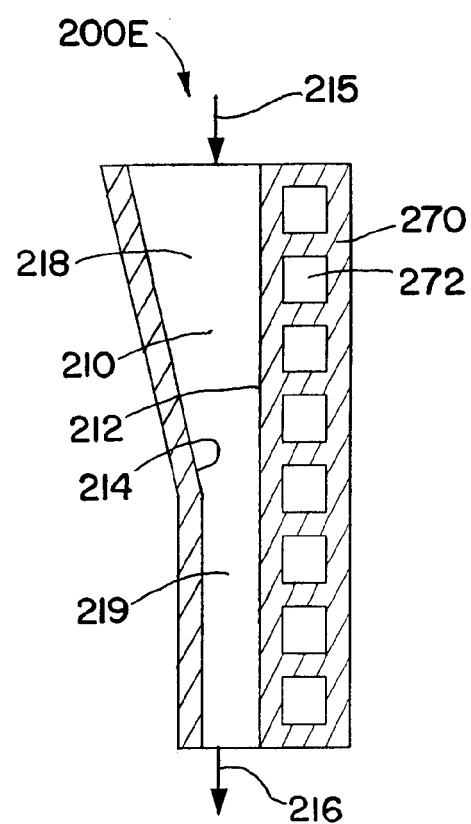

The repeating unit 200E illustrated in FIG. 9 is the same as the repeating unit 200D illustrated in FIG. 8 with the exception that the process microchannel 210 in the repeating unit 200E includes a converging section 218 which has a converging cross-sectional area and a non-converging section 219 which has a non-converging cross-sectional area. Shear stress is applied to the non-Newtonian fluid by flowing the non-Newtonian fluid in the converging section 218. This results in a reduction in viscosity. During flow in the non-converging section 219, the viscosity of the non-Newtonian fluid may increase.

Figure 10:
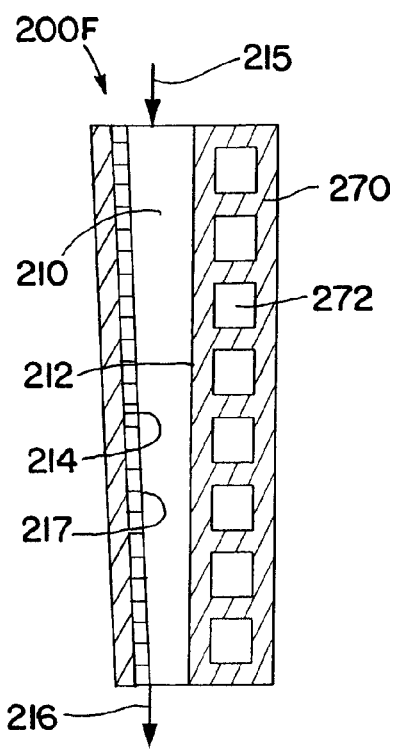

The repeating unit 200F illustrated in FIG. 10 is the same as the repeating unit 200D illustrated in FIG. 8 with the exception that surface features 217 are formed on and/or in the interior wall 214. In this embodiment, enhanced shear stress may be achieved by use of the combination of the converging cross-sectional area and the surface features 217.

Figure 11:
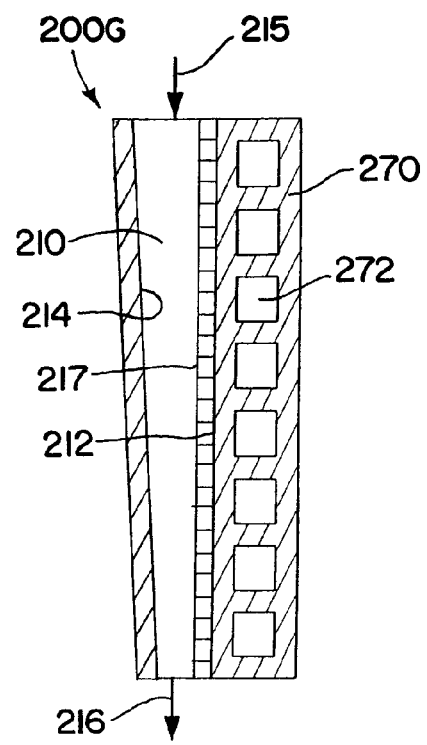

The repeating unit 200G illustrated in FIG. 11 is the same as the repeating unit 200F illustrated in FIG. 10 with the exception that the surface features 217 are positioned on the interior wall 212, rather than the interior wall 214.

Figure 12:
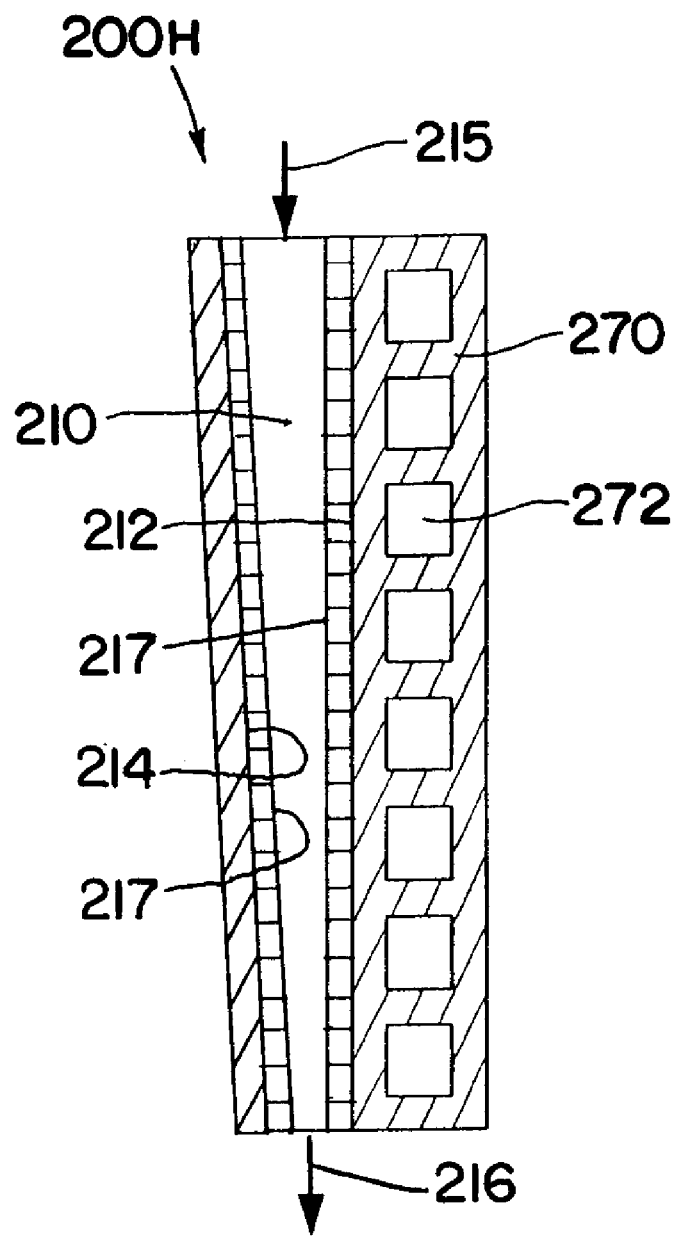

The repeating 200H illustrated in FIG. 12 is the same as the repeating unit 200F illustrated in FIG. 10 with the exception that the surface features 217 are positioned on both interior walls 212 and 214.

Referring to FIG. 13, microchannel repeating unit 200I comprises process microchannel 210, staged addition channel 240, apertured section 250, and heat exchange zone 270. The process microchannel 210 includes at least two process zones, and opposite side walls 212 and 214. Surface features 217 are positioned on sidewall 212. Sidewall 212 may also be referred to as a heat transfer wall. Apertured section 250 is positioned in sidewall 214 which is a common wall for process microchannel 210 and staged addition channel 240. The apertured section 250 may be referred to as a porous section or porous substrate. The apertured section 250 may comprise a sheet or plate having a plurality of apertures extending through it. Additional embodiments of the apertured section 240 are discussed in detail below. The stage addition channel 240 opens to process microchannel 210 through apertured section 250. The staged addition channel 240 may be a flow-through channel with an outlet opening 243 or it may be a closed end channel. The process microchannel 210 has mixing zone 211, and may have non-apertured regions (not shown in the drawings) upstream and/or downstream from mixing zone 211. The mixing zone 211 is adjacent to the apertured section 250. The mixing zone 211 may have a restricted cross section to enhance mixing. In operation, the first fluid stream flows into process microchannel 210, as indicated by directional arrow 215, and into the mixing zone 211. The second fluid stream flows into staged addition channel 240, as indicated by arrow 242, and then flows through apertured section 250, as indicated by arrows 244, into the mixing zone 211. In mixing zone 211, the second fluid stream contacts and mixes with the first fluid stream to form a multiphase mixture or an emulsion. The second fluid stream may form a discontinuous phase (e.g., gas bubbles, liquid droplets) within the first fluid stream. The first fluid stream may form a continuous phase. The fluids contact the surface features 217 resulting in the application of shear stress on the fluids. The first and/or second fluid stream and/or resulting multiphase mixture or emulsion may be non-Newtonian. The applied shear stress reduces the viscosity of the non-Newtonian fluid. The multiphase mixture or emulsion flows from the mixing zone 211 out of the process microchannel 210, as indicated by arrow 216. The first and/or second fluid stream may contain a homogeneous catalyst and a reaction between the first fluid stream and the second fluid stream may be conducted in the process microchannel 210. Part of the second fluid stream may flow through the opening 243 in the staged addition channel 240 and be recycled back to the header 104, while the remainder of the second fluid stream may flow through the apertured section 250, as discussed above.

The microchannel repeating unit 200I has a heat exchange zone 270 which includes heat exchange channels 272. When heating or cooling is desired, heat exchange fluid flows through the heat exchange channels 272, and heats or cools the fluids in the process microchannel 210 and staged addition channel 240. The degree of heating or cooling may vary over the axial length of the process microchannel 210 and staged addition channel 240. The heating or cooling may be negligible or non-existent in some sections of the process microchannel 210 and staged addition channel 240, and moderate or relatively high in other sections. Alternatively, the heat exchange fluid may flow in a direction that is counter-current or cross current relative to the flow of fluid in the process microchannel 210. Alternatively, the heating or cooling may be effected using heating or cooling mediums other than a heat exchange fluid. For example, heating may be effected using an electric heating element. Cooling may be effected using a non-fluid cooling element. The electric heating element and/or non-fluid cooling element may be used to form one or more walls of the process microchannel 210 and/or staged addition channel 240. The electric heating element and/or non-fluid cooling element may be built into one or more walls of the process microchannel 210 and/or staged addition channel 240. Multiple heating or cooling zones may be employed along the axial length of the process microchannel 210. Similarly, multiple heat exchange fluids at different temperatures may be employed along the length of the process microchannel 210.

The fluid flowing through the process microchannel 210 may undergo a pressure drop as it flows from the process microchannel inlet to the process microchannel outlet. As a result of this pressure drop the internal pressure within the process microchannel 210 may decrease progressively from a high point near the process microchannel inlet to a low point near the process microchannel outlet. In order to produce gas bubbles or liquid droplets that are relatively uniform in size, it may be desirable to maintain a substantially constant pressure differential across the apertured section 250 along the axial length of the apertured section 250. In order to do this, the internal pressure within the staged addition channel 240 may be reduced along its axial length to match the drop in internal pressure in the process microchannel 210 as a result of the pressure drop resulting from the flow of fluid through the process microchannel. This may be done by providing the staged addition channel 240 in the form of a microchannel such that the second fluid stream flowing in the staged addition channel undergoes a pressure drop similar to the pressure drop for the fluid flowing through the process microchannel 210.

In one embodiment, the apertured section 250 may comprise a plurality of discrete feed introduction points rather than a continuous introduction of the second fluid stream along the axial length of the apertured section 250. The number of discrete feed introduction points may be any number, for example, one, two, three, four, five six, seven, eight, 10, 20, 50, 100, etc.

The microchannel repeating unit 200J illustrated in FIG. 14 is the same as the microchannel repeating unit 200I illustrated in FIG. 13 except that the repeating unit 200J has a first repeating section 205 and a second repeating section 205A positioned adjacent to one another. The first repeating section 205 comprises first process microchannel 210, first staged addition channel 240 and first apertured section 250. The second repeating section 205A comprises a second process microchannel 210A, second staged addition channel 240A, and second apertured section 250A. The process microchannel 210 includes surface features 217, and the process microchannel 210A includes surface features 217A. Heat exchange channels 272 are adjacent to and in thermal contact with the first repeating section 205 and are remote from but in thermal contact with the second repeating section 205A.

The microchannel repeating unit 200K illustrated in FIG. 15 comprises process microchannel 210 which includes at least two process zones, one of which includes reaction zone 220 wherein catalyst 222 is situated, and heat exchange zone 270, which includes heat exchange channels 272. The catalyst 222 illustrated in FIG. 15 is in the form of a bed of particulate solids. However, any of the catalyst forms discussed in the specification may be used in the process microchannel illustrated in FIG. 15. Surface features 217 are positioned on and/or in opposite sidewalls 212 and 214 upstream of the reaction zone 220. In operation, the first fluid stream or a mixture of the first fluid stream and the second fluid stream, and optionally one or more additional fluid streams, enter the reaction zone 220, as indicated by arrow 215, contact the catalyst 222 and react to form a product. One or more of the fluids and/or the mixture of fluids may be non-Newtonian. Shear stress is applied to the non-Newtonian fluid by flowing the non-Newtonian fluid in contact with the surface features 217. This reduces the viscosity of the non-Newtonian fluid. The product flows out of the reaction zone 220, as indicated by arrow 216.

Figure 16:
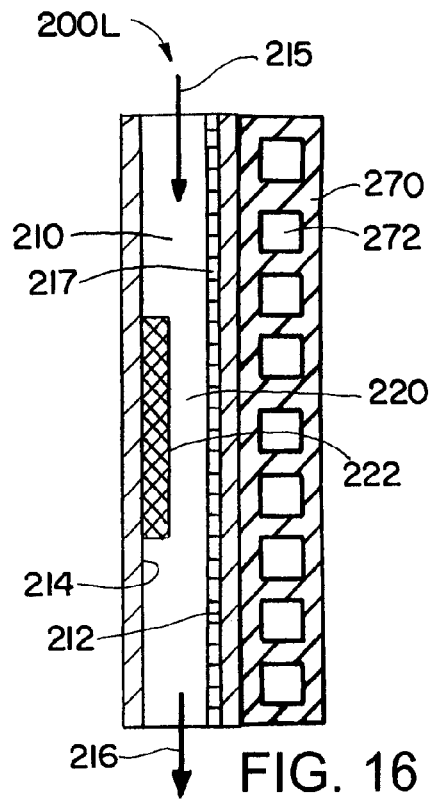
FIG. 16 is a schematic illustration of a repeating unit comprising a process microchannel and adjacent heat exchange channels that may be used in the microchannel processing unit illustrated in FIG. 3. The process microchannel contains a reaction zone comprising a catalyst. The catalyst is positioned on one of the interior walls of the process microchannel. The interior wall of the process microchannel opposite the catalyst comprises surface features for applying shear stress to the non-Newtonian fluid.

The microchannel repeating 200L illustrated in FIG. 16 comprises process microchannel 210, which includes at least two process zones, one of which includes reaction zone 220 wherein catalyst 222 is situated, and heat exchange zone 270, which includes heat exchange channels 272. The catalyst 222 is positioned on interior wall 214. Surface features 217 are positioned on the opposite interior wall 212. The catalyst 222 may be positioned on a support which is mounted on the interior wall 214. The catalyst may be in any of the forms discussed in the specification. In operation, the first fluid stream or a mixture of the first fluid stream and the second fluid stream, and optionally one or more additional fluid streams, enter the reaction zone 220, as indicated by arrow 215, contact the catalyst 222 and react to form a product. Shear stress is applied to the non-Newtonian fluid, which may be one or more of the reactant fluid streams and/or the product, as the non-Newtonian fluid flows through the process microchannel 210 in contact with the surface features 217. The shear stress applied to the non-Newtonian fluid reduces the viscosity of the non-Newtonian fluid.

Figure 17:
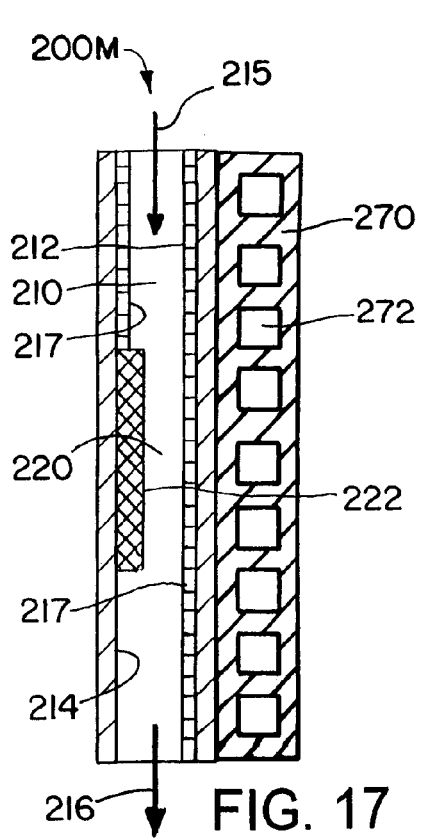
FIG. 17 is a schematic illustration of a repeating unit that is similar to the repeating unit illustrated in FIG. 16 with the exception that the interior wall of the process microchannel wherein the catalyst is mounted also includes surface features for applying shear stress to the non-Newtonian fluid, these surface features being upstream of the catalyst.

Repeating unit 200M illustrated in FIG. 17 is the same as repeating unit 200L illustrated in FIG. 16 with the exception that the repeating unit 200M includes additional surface features 217 on the interior sidewall 214 upstream of the catalyst 222. The additional surface features 217 in the repeating unit 200M provide for additional shear stress and therefore a further reduction in viscosity in the process microchannel 210 upstream of the reaction zone 220.

Figure 18:
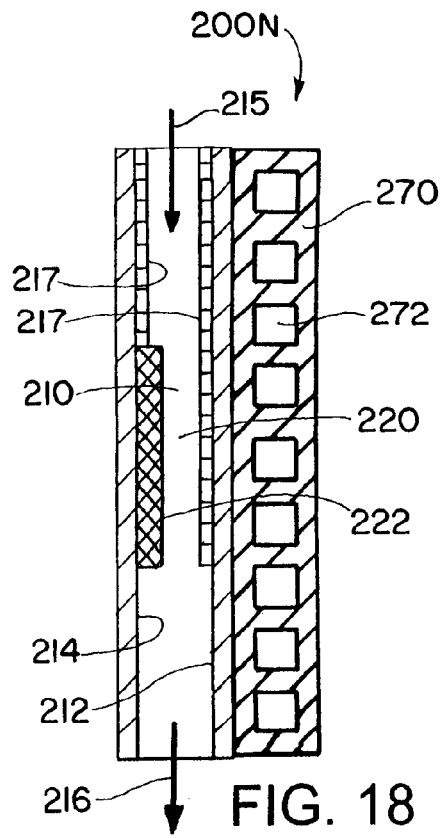
FIG. 18 is a schematic illustration of a repeating unit similar to the repeating unit illustrated in FIG. 17 with the exception that the surface features that are downstream of the catalyst in FIG. 17 are excluded in FIG. 18.

Repeating 200N illustrated in FIG. 18 is the same as the repeating unit 200M illustrated in FIG. 17 with the exception that in the repeating 200N the surface features 217 downstream of the reaction zone have been eliminated. This provides for reduced shear stress on the product flowing out of the reaction zone 220 as compared to repeating unit 200M.

Figure 19:
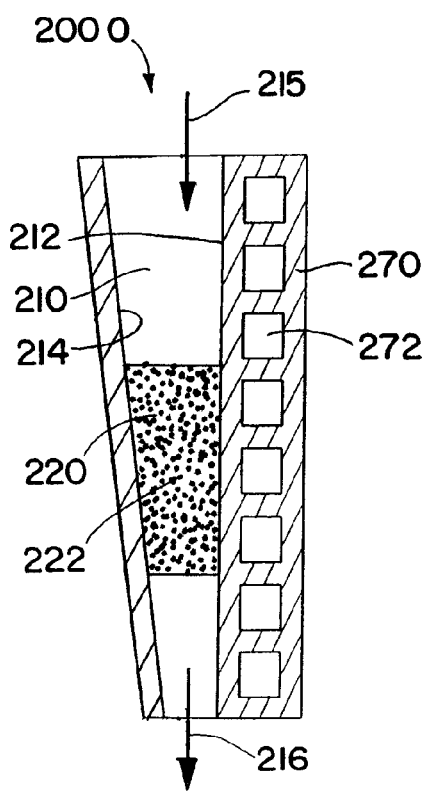
FIG. 19 is a schematic illustration of a repeating unit comprising a process microchannel and adjacent heat exchange channels that may be used in the microchannel processing unit illustrated in FIG. 3. The process microchannel has a converging cross-sectional area. A catalyst in the form of a bed of particulate solids is positioned in the process microchannel. However, any of the catalysts forms discussed in the specification may be used in the process microchannel illustrated in FIG. 19.

Repeating 200O illustrated in FIG. 19 is similar to repeating unit 200D illustrated in FIG. 8 with the exception that repeating 200O includes reaction zone 220 which contains catalyst 222. The catalyst 222 illustrated in FIG. 19 is in the form of a bed of particulate solids. However, any of the catalyst forms discussed in the specification may be used in the reaction zone 220. The reactants and/or product may be non-Newtonian. The process microchannel 210 has a converging cross-sectional area which applies shear stress to the non-Newtonian fluid flowing in the process microchannel. This reduces the viscosity of the non-Newtonian fluid. Heat exchange is provided by the heat exchange channels 272 which are positioned in the heat exchange zone 270.

Figure 20:
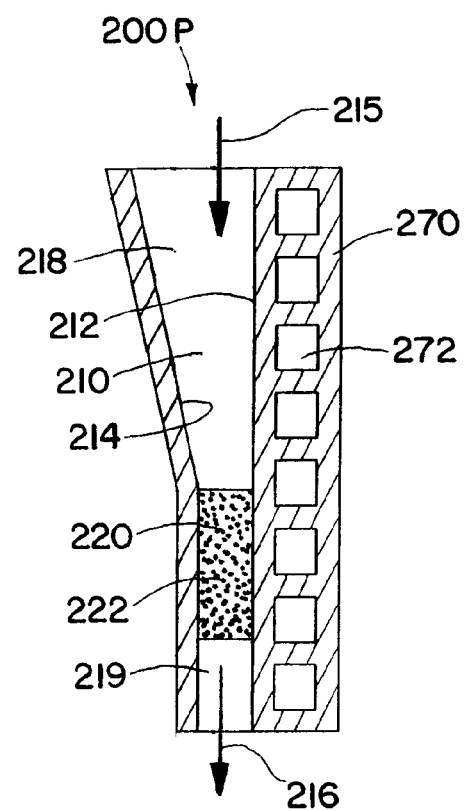
FIG. 20 is a schematic illustration of a repeating unit that is similar to the repeating unit illustrated in FIG. 19 with the exception that the process microchannel includes two sections, one of the sections having a converging cross-sectional area, and the other section having a non-converging cross-sectional area. The catalyst, which is in the form of a bed of particulate solids, is in the section of the process microchannel having the non-converging cross-sectional area. Alternatively, instead of being in the form of a bed of particulate solids, the catalyst may have any of the forms discussed herein.

Repeating unit 200P, which is illustrated in FIG. 20, is the same as repeating unit 200E illustrated in FIG. 9 with the exception that repeating 200P includes reaction zone 220, which contains catalyst 222. The catalyst 222 illustrated in FIG. 20 is in the form of a bed of particulate solids. However, any of the catalyst forms discussed in the specification may be used. The process microchannel 210 includes converging section 218 and non-converging section 219. The reaction zone 220 is positioned in the non-converging section 219. The reactants which are non-Newtonian and which may comprise the first fluid or a mixture of the first fluid and second fluid and optionally one or more additional fluids, flow in the process microchannel 210 as indicated by arrow 215, contact the catalyst 222, and form a product which flows out of the process microchannel 210 as indicated by arrow 216. Shear stress is applied to the non-Newtonian fluid flowing in the converging section 218 and as a result the viscosity of the non-Newtonian fluid is reduced. Heat exchange may be provided between the heat exchange channels 272 in the heat exchange zone 270 and the process microchannel 210.

Figure 21:
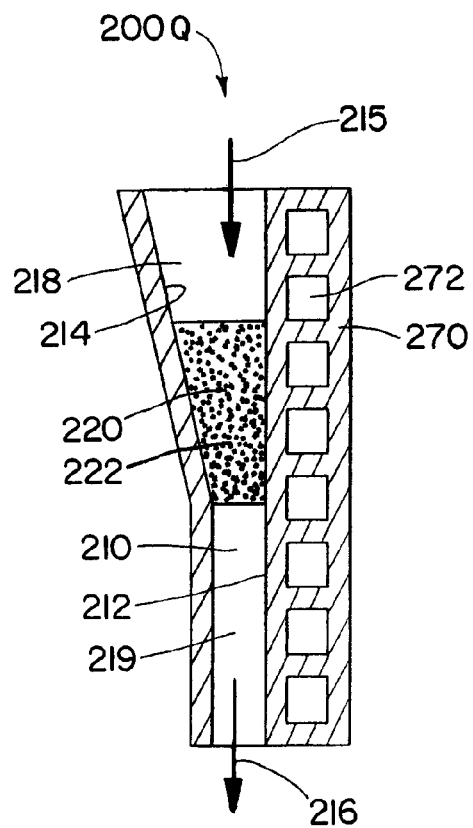
FIG. 21 is a schematic illustration of a repeating unit that is similar to the repeating unit illustrated in FIG. 20 with the exception that the catalyst is in the section of the process microchannel having the converging cross-sectional area.

The repeating unit 200Q illustrated in FIG. 21 is the same as the repeating unit 200P illustrated in FIG. 20 with the exception that the reaction zone 220 is positioned in the converging section 218 of the process microchannel 210 rather than in the non-converging section 219 as illustrated in FIG. 20.

Figure 22:
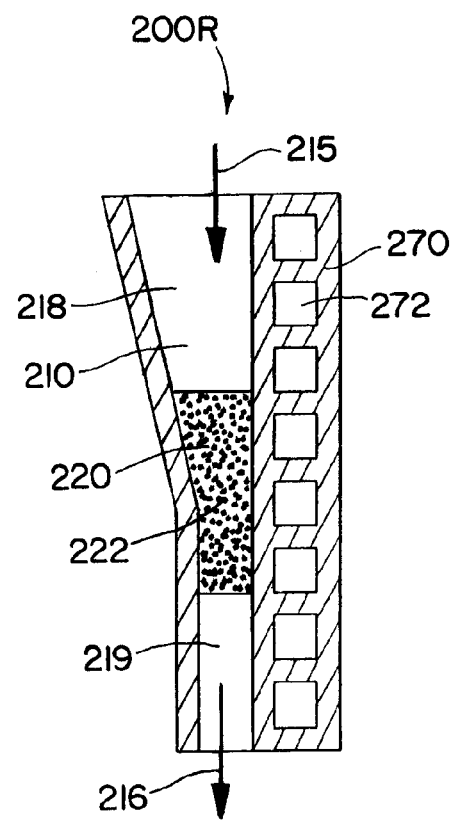
FIG. 22 is a schematic illustration of a repeating unit that is similar to the repeating unit illustrated in FIG. 20 with the exception that the catalyst is positioned partly in the section having the converging cross-sectional area and partly in the section having the non-converging cross-sectional area.

The repeating unit 200R illustrated in FIG. 22 is the same as the repeating unit 200P illustrated in FIG. 20 with the exception that the reaction zone 220 is positioned partly in the converging section 218 of process microchannel 210 and partly in the non-converging section 219 of process microchannel 210.

Figure 23:
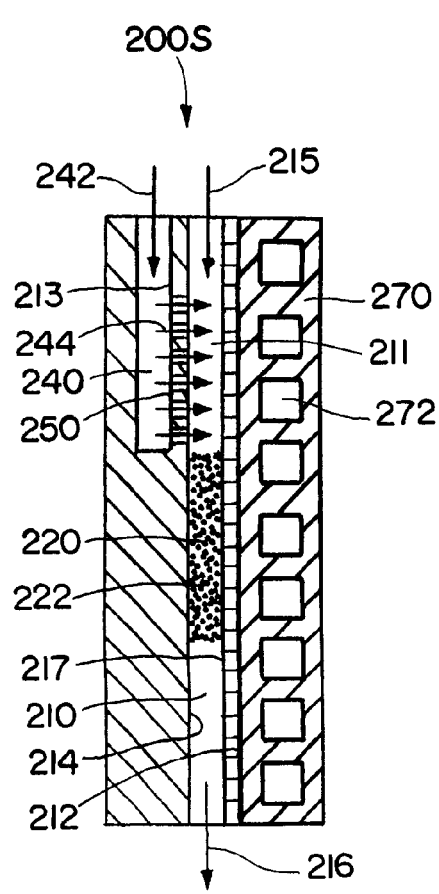
FIG. 23 is a schematic illustration of a repeating unit that may be used in the microchannel processing unit illustrated in FIG. 3. The repeating unit comprises a process microchannel and a staged addition channel. An apertured section is positioned between the process microchannel and staged addition channel. Heat exchange channels are positioned adjacent to the process microchannel. The process microchannel contains a reaction zone and a mixing zone. The mixing zone is upstream of the reaction zone. The process microchannel includes surface features for applying shear stress to the non-Newtonian fluid. The surface features are positioned on or in one of the interior walls of the process microchannel along the length of the process microchannel. A catalyst is positioned in the reaction zone. The catalyst illustrated in FIG. 23 is in the form of a bed of particulate solids. However, the catalyst may have any of the forms discussed in the specification. A feed stream flows in the process microchannel. A staged addition stream flows from the staged addition channel through the apertured section into the process microchannel where it contacts the feed stream in the mixing zone to form a reactant mixture. The reactant mixture flows in the reaction zone, and reacts to form product.

Microchannel repeating unit 200S is illustrated in FIG. 23. Repeating unit 200S comprises process microchannel 210, staged addition channel 240, and apertured section 250. A common side wall 214 separates process microchannel 210 and staged addition channel 240. The apertured section 250 is positioned in common wall 214. The apertured section 250 contains a plurality of apertures for permitting the flow of the second fluid stream through the apertured section. The process microchannel 210 includes two process zones, one of which is mixing zone 211, and the other is reaction zone 220. Catalyst 222 is positioned in the reaction zone 220. The mixing zone 211 is upstream from the reaction zone 220. Surface features 217 are positioned on and/or in sidewall 212 of process microchannel 210. Sidewall 212 may be referred to as a heat transfer wall. The first fluid stream flows into process microchannel 210, as indicated by the arrow 215, and into the mixing zone 211. The second fluid stream flows into staged addition channel 240, as indicated by arrow 242, and from the staged addition channel 240 through the apertured section 250 into mixing zone 211, as indicated by arrows 244. The direction of flow of the second fluid stream in the staged addition channel 240, as indicated by arrow 242, is cocurrent with the direction of flow of the first fluid stream in the process microchannel 210, as indicated by arrow 215. Alternatively, the flow of second fluid stream in the staged addition channel 240 may be counter-current or cross-current relative to the flow of the first fluid stream in the process microchannel 210. The first fluid stream and second fluid stream contact each other in the mixing zone 211 and form a reactant mixture. The reactant mixture flows from the mixing zone 211 into the reaction zone 220, contacts the catalyst, and reacts to form the product. The product exits the process microchannel 210, as indicated by arrow 216. The first fluid stream, the reactant mixture and/or the product may be non-Newtonian. Shear stress is applied to the non-Newtonian fluid as the non-Newtonian fluid contacts the surface features 217. The shear stress applied to the non-Newtonian fluid reduces the viscosity of the non-Newtonian fluid. Heat exchange channels 272 in heat exchange zone 270 exchange heat with the process fluids in the staged addition channel 240 and the process microchannel 210.

In an alternate embodiment of the repeating unit 200S illustrated in FIG. 23, a supplemental mixing zone may be provided in the process microchannel 210 between the mixing zone 211 and the reaction zone 220.

Figure 24:
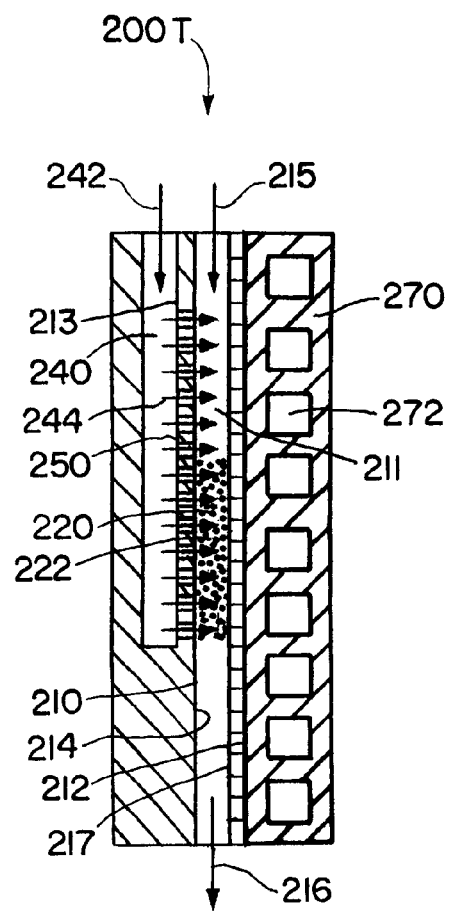
FIG. 24 is a schematic illustration of a repeating unit that is the same as the repeating unit illustrated in FIG. 23 except that part of the staged addition stream contacts the feed steam in the mixing zone and part of the staged addition stream contacts the feed stream in the reaction zone.

The repeating unit 200T illustrated in FIG. 24 is the same as the repeating unit 200S illustrated in FIG. 23 with the exception that part of the second fluid stream mixes with the first fluid stream in the mixing zone 211, and part of the second fluid stream mixes with the first fluid stream in the reaction zone 220. The amount of the second fluid stream that mixes with the first fluid stream in the mixing zone 211 may be from about 1% to about 99% by volume of the second fluid stream, and in one embodiment from about 5% to about 95% by volume, and in one embodiment from about 10% to about 90% by volume, and in one embodiment from about 20% to about 80% by volume, and in one embodiment from about 30% to about 70% by volume, and in one embodiment from about 40% to about 60% by volume of the second fluid stream. The remainder of the second fluid stream mixes with the first fluid stream in the reaction zone 220.

Figure 25:
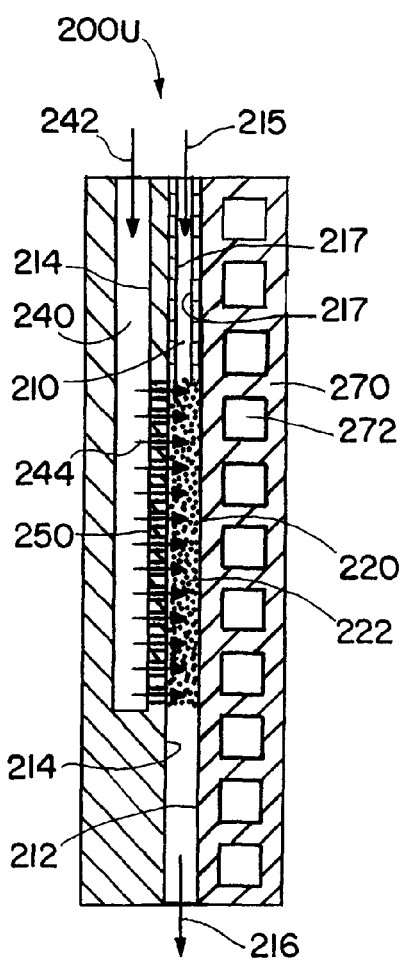
FIG. 25 is a schematic illustration of a repeating unit that is similar to the repeating unit illustrated in FIG. 23 except that the staged addition stream contacts the feed stream in the reaction zone. Also, the surface features are positioned on and/or in opposite interior walls of the process microchannel upstream of the catalyst.

The repeating unit 200U illustrated in FIG. 25 is the same as the repeating unit 200T illustrated in FIG. 24 with the exception that the repeating unit 200U does not contain the separate mixing zone 211. Also, in the repeating unit 200U, the sidewalls 212 and 214 of the process microchannel 210 have surface features 217 on and/or in the surface of each upstream of the reaction zone 220. With repeating unit 200U, the second fluid stream flows through the apertured section 250 into the reaction zone 220 where it contacts the first fluid stream and reacts in the presence of the catalyst 222 to form the product. The product then flows out of the process microchannel 210, as indicated by arrow 216.

Figure 26:
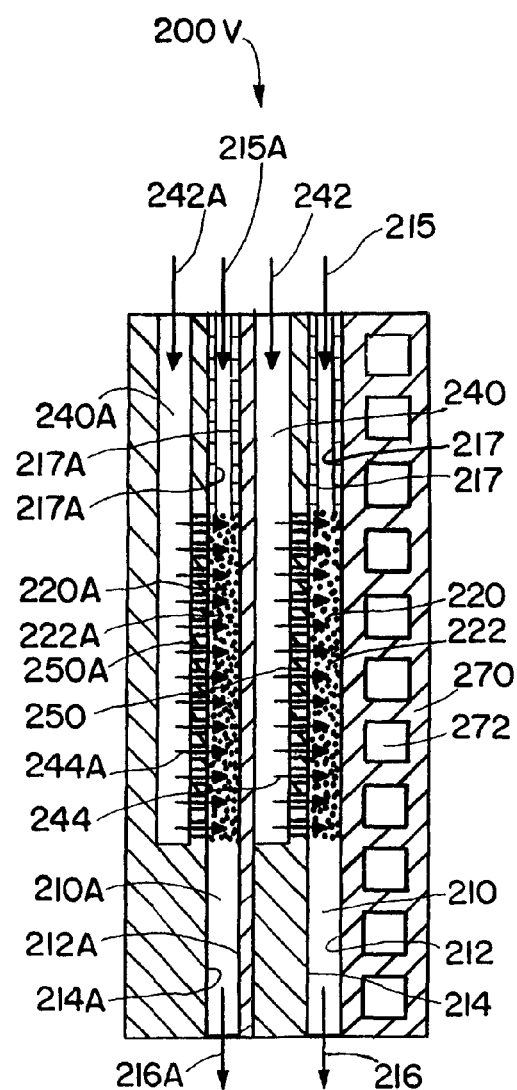
FIG. 26 is a schematic illustration of a repeating unit that is similar to the repeating unit illustrated in FIG. 25 with the exception that the repeating unit illustrated in FIG. 26 contains two adjacent sets of process microchannels, staged addition channels and apertured sections. One of these sets is adjacent to and in thermal contact with the heat exchange channels while the other set is in thermal contact with the heat exchange channels.

The repeating unit 200V illustrated in FIG. 26 is the same as repeating unit 200U illustrated in FIG. 25 with the exception that the repeating unit 200V contains two adjacent sets of process microchannels, staged addition channels and apertured sections. One of these sets is adjacent to the heat exchange channels 272 while the other set is remote from but in thermal contact with the heat exchange channels 272.

In an alternate embodiment, the repeating unit may comprise two process microchannels and a single staged addition channel. In this embodiment the repeating unit may comprise a first process microchannel, a second process microchannel, and a staged addition channel positioned between the first process microchannel and the second process microchannel. Each process microchannel may have a wall with an apertured section. Surface features may be positioned on and/or in one or more sidewalls in each process microchannel. A catalyst may be positioned in each process microchannel. The first fluid flows in the first process microchannel and the second process microchannel in contact with the catalyst. The second fluid flows from the staged addition channel through the apertured section in the first process microchannel in contact with the catalyst and the first fluid and through the apertured section in the second process microchannel in contact with the catalyst and the first fluid to form a reaction product. Non-Newtonian fluids flow in the process microchannels in contact with the surface features. This reduces the viscosity of the non-Newtonian fluids.

The microchannel processing unit core 102 including the process microchannels, staged addition channels, and heat exchange channels, as well as any process headers, process footers, heat exchange headers, heat exchange footers, and the like, may be made of any material that provides sufficient strength, dimensional stability and heat transfer characteristics to permit operation of the inventive process. These materials may include steel; aluminum, titanium; nickel, platinum; rhodium; copper; chromium; brass; alloys of any of the foregoing metals; polymers (e.g., thermoset resins); ceramics; glass; composites comprising one or more polymers (e.g., thermoset resins) and fiberglass; quartz; silicon; or a combination of two or more thereof.

The flow and/or mixing within the process microchannels 210, staged addition channels 240, and/or heat exchange channels 272 may be modified by the use of surface features formed on one, two or more interior walls of such channels. The surface features may be in the form of depressions in and/or projections from one or more of the channel walls. These surface features may be oriented at angles relative to the direction of flow through the channels. The surface features may be aligned at an angle from about 1° to about 89°, and in one embodiment from about 30° to about 75°, relative to the direction of flow. The angle of orientation may be an oblique angle. The angled surface features may be aligned toward the direction of flow or against the direction of flow. The flow of fluids in contact with the surface features may force one or more of the fluids into depressions in the surface features, while other fluids may flow above the surface features. Flow within the surface features may conform with the surface feature and be at an angle to the direction of the bulk flow in the channel. As fluid exits the surface features it may exert momentum in the x and y direction for an x,y,z coordinate system wherein the bulk flow is in the z direction. This may result in a churning or rotation in the flow of the fluids. This pattern may be helpful for mixing a two-phase flow as the imparted velocity gradients may create fluid shear that breaks up one of the phases into small and well dispersed droplets.

Two or more surface feature regions within the process microchannels 210 may be placed in series such that mixing of the fluids to form a multiphase mixture or emulsion may be accomplished using a first surface feature region, followed by at least one second surface feature region where a different flow pattern may be used. The second flow pattern may be used to separate one or more liquids or gases from the fluid mixture. In the second surface feature region, a flow pattern may be used that creates a centrifugal force that drives one liquid toward the interior walls of the process microchannels while another liquid remains in the fluid core. One pattern of surface features that may create a strong central vortex may comprise a pair of angled slots on the top and bottom of the process microchannel. This pattern of surface features may be used to create a central swirling flow pattern.

The apertured section 250 may comprise an interior portion that forms part of one or more of the interior walls of each process microchannel 210. A surface feature sheet may overlie this interior portion of the apertured section. Surface features may be formed in and/or on the surface feature sheet. The second fluid may flow through the apertured section and the surface feature sheet into the process microchannel. Part of the second fluid may be detached from the surface of the surface feature sheet while part may flow within the surface features of the surface feature sheet. The surface feature sheet may contain angled surface features that have relatively small widths or spans relative to the overall flow length. The surface feature sheet may provide mechanical support for the apertured section. The surface features may impart a vortical flow pattern to the fluids in the process microchannel and promote good mixing of the two phases and or promote the formation of small emulsion droplets. The vortical flow pattern may impart shear to the second liquid flowing through the apertured section and thus reduce the size of the droplets in the bulk flow path.

Examples of the surface features are illustrated in FIGS. 46-47. The surface features may have two or more layers stacked on top of each other or intertwined in a three-dimensional pattern. The pattern in each discrete layer may be the same or different. Flow may rotate or advect in each layer or only in one layer. Sub-layers, which may not be adjacent to the bulk flow path of the channel, may be used to create additional surface area. The flow may rotate in the first level of surface features and diffuse molecularly into the second or more sublayers to promote reaction. Three-dimensional surface features may be made via metal casting, photochemical machining, laser cutting, etching, ablation, or other processes where varying patterns may be broken into discrete planes as if stacked on top of one another. Three-dimensional surface features may be provided adjacent to the bulk flow path within the microchannel where the surface features have different depths, shapes, and/or locations accompanied by sub-features with patterns of varying depths, shapes and/or locations.

The use of surface features or fully etched plates with patterns may be advantageous to provide structural support for thin or weak apertured plates or sheets used to form the apertured section. In one embodiment, the apertured sheet may be made from a polymeric material that has very small mean pore diameters (less than 1 micron) but can not withstand a high pressure differential (greater than about 10 psi, or greater than about 50 psi, or greater than about 100 psi, or larger) that is required to force the second liquid through the apertured section into the process microchannel. The open span required for structural support may be reduced from the cross section of the process microchannel to the open span and run the length of the surface feature. The span of the surface feature may be made smaller as required if the apertured sheet or plate has reduced mechanical integrity. One advantage of the surface features, is the convective flow that may occur within the surface features such that a significant shear stress may be created at the wall of the apertured section to assist with the detachment of small droplets.

An example of a three-dimensional surface feature structure may include recessed chevrons at the interface adjacent the bulk flow path of the microchannel. Beneath the chevrons there may be a series of three-dimensional structures that connect to the surface features adjacent to the bulk flow path but are made from structures of assorted shapes, depths, and/or locations. It may be further advantageous to provide sub-layer passages that do not directly fall beneath an open surface feature that is adjacent to the bulk flow path within the microchannel but rather connect through one or more tortuous two-dimensional or three-dimensional passages. This approach may be advantageous for creating tailored residence time distributions in the microchannels, where it may be desirable to have a wider versus more narrow residence time distribution.

The length and width of a surface feature may be defined in the same way as the length and width of a microchannel. The depth may be the distance which the surface feature sinks into or rises above the microchannel surface. The depth of the surface features may correspond to the direction of stacking a stacked and bonded microchannel device with surface features formed on or in the sheet surfaces. The dimensions for the surface features may refer the maximum dimension of a surface feature; for example the depth of a rounded groove may refer to the maximum depth, that is, the depth at the bottom of the groove.

The surface features may have depths that are less than about 2 mm, and in one embodiment less than about 1 mm, and in one embodiment in the range from about 0.01 to about 2 mm, and in one embodiment in the range from about 0.01 to about 1 mm, and in one embodiment in the range from about 0.01 mm to about 0.5 mm. The width of the surface features may be sufficient to nearly span the microchannel width (for example, herringbone designs), but in one embodiment (such as fill features) may span about 60% or less of the width of the microchannel, and in one embodiment about 50% or less, and in one embodiment about 40% or less, and in one embodiment from about 0.1% to about 60% of the microchannel width, and in one embodiment from about 0.1% to about 50% of the microchannel width, and in one embodiment from about 0.1% to about 40% of the microchannel width. The width of the surface features may be in the range from about 0.05 mm to about 100 cm, and in one embodiment in the range from about 0.5 mm to about 5 cm, and in one embodiment in the range from about 1 to about 2 cm.

Multiple surface features or regions of surface features may be included within a microchannel, including surface features that recess at different depths into one or more microchannel walls. The spacing between recesses may be in the range from about 0.01 mm to about 10 mm, and in one embodiment in the range from about 0.1 to about 1 mm. The surface features may be present throughout the entire length of a microchannel or in portions or regions of the microchannel. The portion or region having surface features may be intermittent so as to promote a desired mixing or unit operation (for example, separation, cooling, etc.) in tailored zones. For example, a one-centimeter section of a microchannel may have a tightly spaced array of surface features, followed by four centimeters of a flat channel without surface features, followed by a two-centimeter section of loosely spaced surface features. The term "loosely spaced surface features" may be used to refer to surface features with a pitch or feature to feature distance that is more than about five times the width of the surface feature.

In one embodiment, the surface features may be in one or more surface feature regions that extend substantially over the entire axial length of a channel. In one embodiment, a channel may have surface features extending over about 50% or less of its axial length, and in one embodiment over about 20% or less of its axial length. In one embodiment, the surface features may extend over about 10% to about 100% of the axial length of the channel, and in one embodiment from about 20% to about 90%, and in one embodiment from about 30% to about 80%, and in one embodiment from about 40% to about 60% of the axial length of a channel.

FIGS. 46 and 47 show a number of different patterns that may be used for surface features. These patterns are not intended to limit the invention, only to illustrate a number of possibilities. As with any surface feature, the patterns may be used in different axial or lateral sections of a microchannel. The process microchannels may comprise one or more structured walls.

Figure 48:
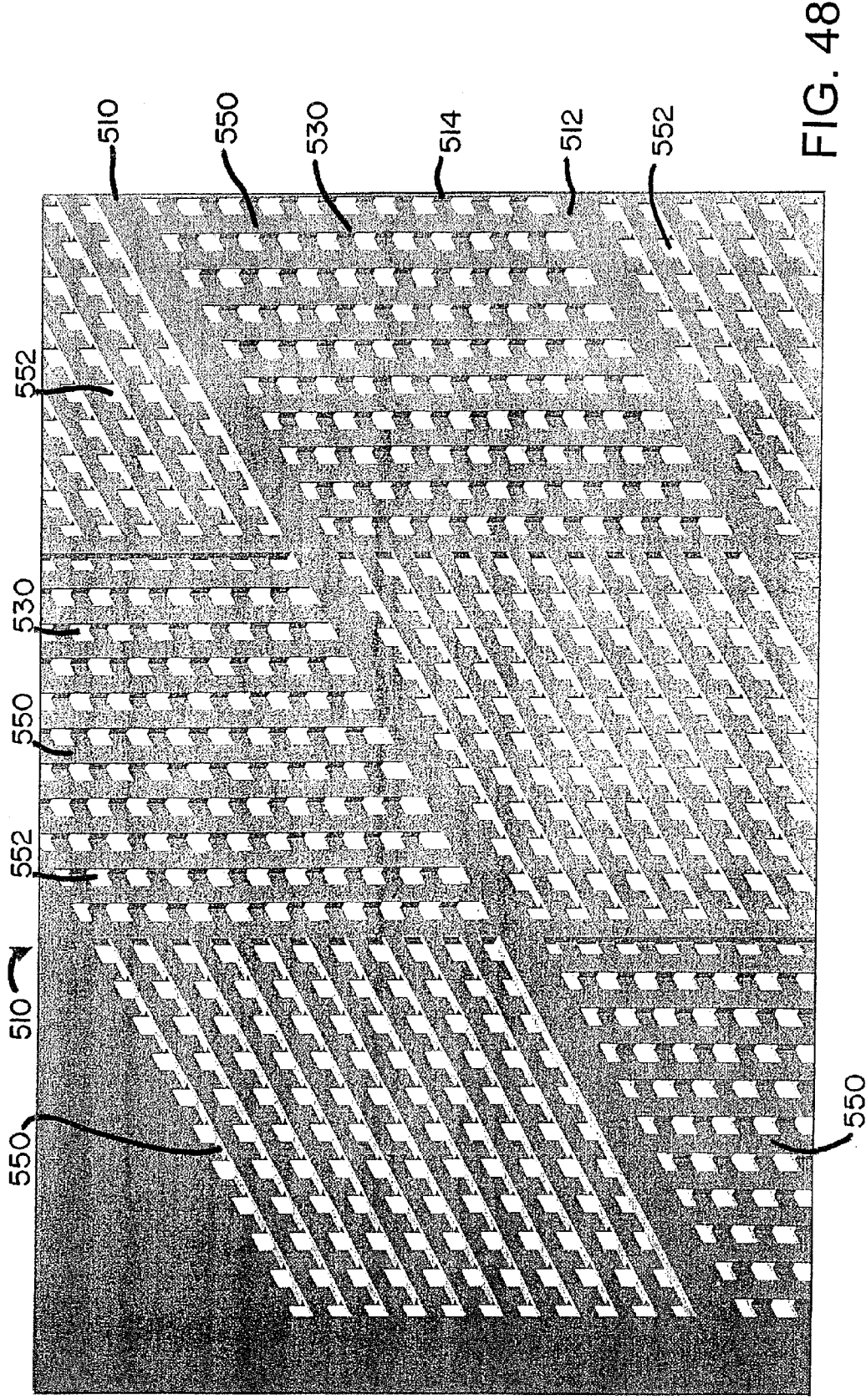
FIG. 48 is a schematic illustration of a shim which has a front or first surface and a back or second surface, and grooves or microgrooves formed in each surface. The grooves or microgrooves in the front or first surface intersect the grooves or microgrooves in the back or second surface with the result being the formation of a plurality of voids, through holes or openings in the shim. The voids, through holes or openings may be referred to as surface features.
Figure 49:
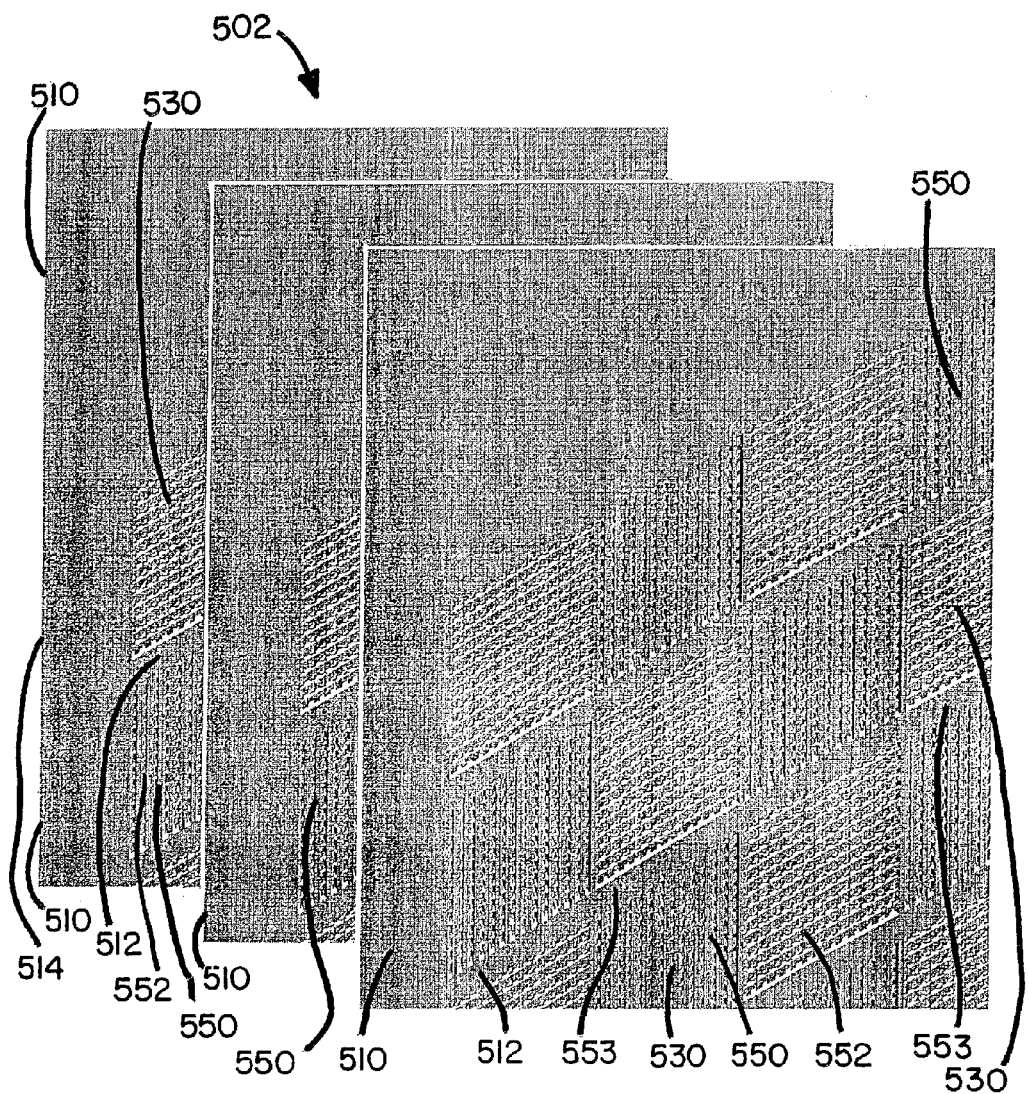
FIG. 49 is a schematic illustration of an exploded view of a composite structure comprising a plurality of the shims illustrated in FIG. 48.

These may be formed from one or more shims. One or more of the shims may contain one or more void spaces, openings or through holes. These may be referred to as surface features. The shims may contain grooves or microgrooves that are formed in one surface of the shims or in both the front or first surface and the back or second surface of the shims. The grooves or microgrooves from the first surface may intersect the grooves or microgrooves from the second surface to form a plurality of voids, through holes or openings in the shim. Examples are illustrated in FIGS. 48 and 49. FIG. 48 illustrates a shim 510 which has a front or first surface 512 and a back or second surface 514, and a plurality of grooves or microgrooves 530 formed in each surface. The grooves or microgrooves 530 formed in the front surface 512 are parallel to each other and are positioned in an array of block patterns 550 wherein in a first block pattern 550 the grooves or microgrooves are aligned in a first or horizontal direction and then in an adjacent second block pattern 550 the grooves or microgrooves are aligned in a second or vertical direction. The array of block patterns 550 comprises a plurality of block patterns 550 arranged in successive rows positioned one above another, the successive rows forming a plurality of columns positioned side by side one another. The grooves or microgrooves 530 formed in the back surface 514 are also parallel to each other and are positioned in an array of block patterns 550 similar to the block patterns 550 in the front surface 512 with the exception that where the front surface 512 has grooves or microgrooves that are aligned in a first or horizontal direction the back surface 514 has grooves or microgrooves 530 that are aligned in a second or vertical direction. Similarly, where the front surface 512 has grooves or microgrooves 530 that are aligned in a second or vertical direction the back surface 514 has grooves or microgrooves that are aligned in a first or horizontal direction. The grooves or microgrooves 530 in the front surface 512 and the grooves or microgrooves 530 in the back surface 514 partially penetrate the shim 510. The penetration of the grooves or microgrooves 530 in the front surface and back surface is sufficient for the grooves or microgrooves 530 in the front surface 512 to intersect the grooves or microgrooves 530 in the back surface 514 with the result being the formation of an array of voids, through holes or openings 552 in the shim 510 at the points where the grooves or microgrooves intersect. The openings 552 may be of sufficient size to permit a fluid to flow or diffuse through the openings 552. The number of openings may range from about 1 to about 200,000 openings per $cm^2$, and in one embodiment from about 10 to about 100,000 openings per $cm^2$. The openings 552 may have average dimensions (e.g., diameter) in the range from about 1 to about 2000 microns, and in one embodiment from about 10 to about 1000 microns. The block patterns 550 may have the dimensions of about 0.01 by about 500 mm, and in one embodiment about 0.5 by about 20 mm. The separation between each block pattern 550 and the next adjacent block pattern may be in the range from about 0.01 to about 10 mm, and in one embodiment about 0.1 to about 1 mm. In this embodiment, the pattern is alternated in an A, B, A, B fashion. In an alternate embodiment the geometry may be varied such that the surface area to volume of the structure may be different along the length of the reactor or in different zones of the reactor. By this manner a reaction with a very high rate of heat release near the top of the reactor may be advantaged by the use of a structure with a higher surface area to volume near the middle or end of the reactor where the kinetics are slower and the rate of heat transfer lower. The resulting heat generation rate along the reactor length or heat flux profile along the reactor length may be made more even or uniform. The pattern may be further optimized to maximize selectivity to the desired reaction products. The pattern may also be optimized to create a tailored gradient within the catalyst structure, along the length of the catalyst structure, or both.

The grooves or microgrooves 530 in the front or first surface 512 intersect the grooves or microgrooves in the back or second surface 514 at right angles in the illustrated embodiment, however, it is to be understood that the angles of intersection may be of any value (e.g., from about 30° to about 120°) and are therefore not limited to being only right angles.

Figure 59:
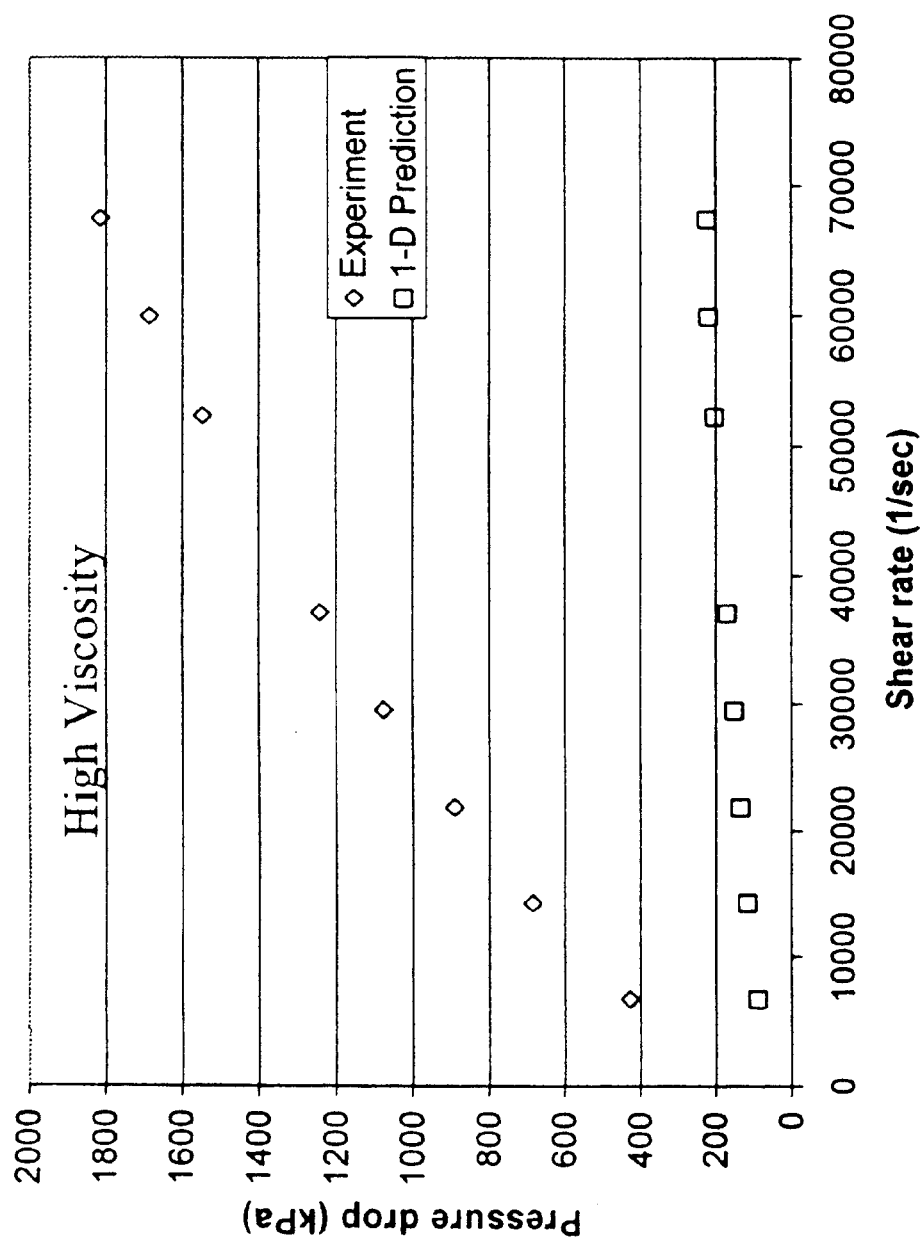
FIG. 59 is a plot showing a comparison of experimental pressure drop with pressure drop predicted using Brookfield viscometer information for a high viscosity non-Newtonian fluid.

FIG. 49 illustrates a composite structure 502 comprising a plurality of the shims 510 illustrated in FIG. 59 which may be stacked one above another or positioned side by side. Any number of shims 510 may be stacked one above the other or positioned side by side in the composite support structure 502. For example, 2, 3, 4, 6, 8, 10, 20, 30, 50, 100, etc., shims 510 may be stacked one above another.

The process microchannels 210, staged addition channels 240 and/or heat exchange channels 272 may have their interior walls coated with a lipophobic coating (the same coating may also provide hydrophobic properties) to reduce surface energy. Teflon may be an example of a coating material that may exhibit both lipophobic and hydrophobic tendencies. The surface of the apertured section 240 that faces the interior of the process microchannel 210 may be coated with a lipophobic coating to reduce droplet drag and promote the formation of smaller droplets. The coating on the apertured section may reduce the energy required to detach a droplet from the surface of the apertured section. In addition, the drag exerted on the second liquid may be lower during droplet detachment and while flowing beyond the apertured section downstream in the process microchannel. In one embodiment, a hydrophobic coating may be applied to the apertured section to assist with the detachment of water droplets into an oil phase. Fluids may not wet surfaces coated with the lipophobic coating. As such, the fluids may slip past the surface and thus negate or reduce the usual no-slip boundary condition of fluids against a wall. As the fluids slip, the local friction factor may decrease as a result of reduced drag and the corresponding pressure drop may be reduced per unit length of the channels. The local heat transfer rate may increase as a result of forced convection over a coated surface as opposed to conductive heat transfer through a stagnant film. The effect of the coating may have a different impact on different types of non-Newtonian fluids. For the case of pseudoplastic (power law) fluid without yield may appear Newtonian above shear rates that are fluid dependent. The viscosity of the fluid may be higher when the shear rate is below a certain value. If the shear rate is locally larger because of the coated wall, then the fluid may be able to shear droplets more easily, move with less energy (lower pumping requirements), and have better heat transfer properties than if the coating were not used. For the case of pseudoplastic (power law) fluid with yield may still have a yield stress, at the wall the yield stress may be greatly reduced with the use of the lipophobic coating. Heat transfer and frictional properties may be enhanced if the apparent yield is low when the coating is used as compared to when the coating is not used. The shear-related effects may be more pronounced for non-Newtonian fluids than for Newtonian fluids.

The microchannel processing unit core 102 may be fabricated using known techniques including wire electrodischarge machining, conventional machining, laser cutting, photochemical machining, electrochemical machining, molding, water jet, stamping, etching (for example, chemical, photochemical or plasma etching) and combinations thereof.

The microchannel processing unit core 102 may be constructed by forming layers or sheets with portions removed that allow flow passage. A stack of sheets may be assembled via diffusion bonding, laser welding, diffusion brazing, and similar methods to form an integrated device. The microchannel processing unit core 102 may be assembled using a combination of sheets or laminae and partial sheets or strips. In this method, the channels or void areas may be formed by assembling strips or partial sheets to reduce the amount of material required.

In one embodiment, subsections or modular units of the microchannel processing unit core 102 may be fabricated using the following components: a substrate piece with a hermetically sealed perimeter and open top/bottom for process flow; and a heat exchange piece. The substrate piece and heat exchange piece may be joined (welded, glued, soldered, etc.) to form a leak-free operating unit. The heat exchange piece may be extruded. The substrate piece and the heat exchange piece may be made from plastic, metal, or other materials as discussed above.

In one embodiment, the microchannel processing unit core 102 may be made by a process that comprises laminating or diffusion bonding shims made of any of the above-indicated materials (e.g., metal, plastic or ceramic) so that each layer has a defined geometry of channels and openings through which to convey fluids. After the individual layers have been created, the catalyst may be inserted. The layers may then be stacked in a prescribed order to build up the lamination. The layers may be stacked side-by-side or one above the other. The completed stack may then be diffusion bonded to prevent fluids from leaking into or out of the microchannel processing unit. After bonding, the device may be trimmed to its final size and prepared for attachment of pipes and manifolds.

Feature creation methods include photochemical etching, milling, drilling, electrical discharge machining, laser cutting, and stamping. A useful method for mass manufacturing may be stamping. In stamping, care should be taken to minimize distortion of the material and maintain tight tolerances of channel geometries. Preventing distortion, maintaining shim alignment and ensuring that layers are stacked in the proper order are factors that should be controlled during the stacking process.

The stack may be bonded through a diffusion process. In this process, the stack may be subjected to elevated temperatures and pressures for a precise time period to achieve the desired bond quality. Selection of these parameters may require modeling and experimental validation to find bonding conditions that enable sufficient grain growth between metal layers.

The next step, after bonding, may be to machine the device. A number of processes may be used, including conventional milling with high-speed cutters, as well as highly modified electrical discharge machining techniques. A full-sized bonded microchannel reactor or microchannel separator unit or sub-unit that has undergone post-bonding machining operations may comprise, for example, tens, hundreds or thousands of shims.

The process microchannels 210 may have a height or width in the range from about 0.05 to about 10 mm, and in one embodiment from about 0.05 to about 5 mm, and in one embodiment from about 0.05 to about 2 mm, and in one embodiment from about 0.05 to about 1.5 mm, and in one embodiment from about 0.05 to about 1 mm, and in one embodiment from about 0.05 to about 0.75 mm, and in one embodiment from about 0.05 to about 0.5 mm. The other dimension of height or width may be of any dimension, for example, up to about 3 meters, and in one embodiment about 0.01 to about 3 meters, and in one embodiment about 0.1 to about 3 meters. The length of the process microchannel 210 may be of any dimension, for example, up to about 10 meters, and in one embodiment from about 0.1 to about 10 meters, and in one embodiment from about 0.2 to about 10 meters, and in one embodiment from about 0.2 to about 6 meters, and in one embodiment from 0.2 to about 3 meters. The process microchannel 210 may have a cross section that is rectangular, or alternatively it may have a cross section having any shape, for example, a square, circle, semi-circle, trapezoid, etc. The shape and/or size of the cross section of the process microchannel 210 may vary over its length. For example, the height or width may taper from a relatively large dimension to a relatively small dimension, or vice versa, over the length of the microchannel.

The process microchannel 210 may have the construction illustrated in FIG. 2. The microchannel illustrated in FIG. 2 has a cross-sectional area that varies from a maximum to a minimum. In one embodiment, the minimum cross-sectional area may be at or near the outlet of the microchannel and the maximum cross-sectional area may be at or near the inlet. This microchannel may be referred to as a microchannel with a converging cross-sectional area. This microchannel may be referred to as a trapezoid microchannel. The microchannel has two dimensions of height, one being a minimum dimension ($h^1$) and the other being a maximum dimension ($h^2$). The height increases gradually from $h^1$ to $h^2$. Alternatively, the microchannel may have a cross-section in the shape of a circle, oval, triangle, etc. The microchannel has at least one dimension of height ($h^1$) that may be in the range of about 0.05 to about 10 mm, and in one embodiment from about 0.05 to about 5 mm, and in one embodiment from about 0.05 to about 2 mm, and in one embodiment from about 0.05 to about 1.5 mm, and in one embodiment from about 0.05 to about 1 mm, and in one embodiment from about 0.05 to about 0.75 mm, and in one embodiment from about 0.05 to about 0.5 mm. The width (w) may be of any dimension, for example, up to about 3 meters, and in one embodiment about 0.01 to about 3 meters, and in one embodiment about 0.1 to about 3 meters. The length (l) may be of any dimension, for example, up to about 10 meters, and in one embodiment from about 0.1 to about 10 meters, and in one embodiment from about 0.2 to about 6 meters. The maximum cross-sectional area may be at least about two-times (2×) the minimum cross-sectional area, and in one embodiment at least about 5-times (5×), and in one embodiment at least about 20-times (20×) the minimum cross-sectional area. The linear velocity of fluid flowing in this microchannel may be increased as the fluid flows along the linear flow path in the microchannel. The local contact time between reactants and catalyst may be reduced as the reactants flow along the linear path in the microchannel.

The staged addition channels 240 and 240A may be microchannels or they may have larger dimensions. The staged addition channels 240 and 240A may have cross sections with any shape, for example, a square, rectangle, circle, semicircle, etc. The staged addition channels 240 and 240A may have an internal height or gap of up to about 10 mm, and in one embodiment up to about 6 mm, and in one embodiment up to about 4 mm, and in one embodiment up to about 2 mm. In one embodiment, the height or gap may be in the range of about 0.05 to about 10 mm, and in one embodiment about 0.05 to about 6 mm, and in one embodiment about 0.05 to about 4 mm, and in one embodiment about 0.05 to about 2 mm. The width of staged addition channel 240 and 240A may be of any dimension, for example, up to about 3 meters, and in one embodiment about 0.01 to about 3 meters, and in one embodiment about 0.1 to about 3 meters. The length of each and staged addition channel 240 and 240A may be of any dimension, for example, up to about 10 meters, and in one embodiment from about 0.1 to about 10 meters, and in one embodiment from about 0.2 to about 10 meters, and in one embodiment from about 0.2 to about 6 meters, and in one embodiment from 0.2 to about 3 meters.

The heat exchange channels 272 may be microchannels or they may have larger dimensions. Each of the heat exchange channels 272 may have a cross section having any shape, for example, a square, rectangle, circle, semi-circle, etc. Each of the heat exchange channels 272 may have an internal height or gap of up to about 10 mm, and in one embodiment in the range of about 0.05 to about 10 mm, and in one embodiment from about 0.05 to about 5 mm, and in one embodiment from about 0.05 to about 2 mm. The width of each of these channels may be of any dimension, for example, up to about 3 meters, and in one embodiment from about 0.01 to about 3 meters, and in one embodiment about 0.1 to about 3 meters. The length of each of the heat exchange channels 272 may be of any dimension, for example, up to about 10 meters, and in one embodiment from about 0.1 to about 10 meters, and in one embodiment from about 0.2 to about 6 meters, and in one embodiment from 0.2 to about 3 meters.

In one embodiment, the process microchannels, optional staged addition channels, and heat exchange channels used in the microchannel processing unit core 102 may have rectangular cross sections and be aligned in side-by-side vertically oriented planes or horizontally oriented stacked planes. These planes may be tilted at an inclined angle from the horizontal. These configurations may be referred to as parallel plate configurations. Various combinations of two or more process microchannels, and optionally adjacent staged addition channels, with a single heat exchange channel, or two or more heat exchange channels in combination with a single process microchannel, and optionally adjacent staged addition channels, may be employed. An array of these rectangular channels may be arranged in a modularized compact unit for scale-up.

The cross-sectioned shape and size of the process microchannels may vary along their axial length to accommodate changing hydrodynamics within the channel. For example, if a reaction is conducted and one of the reactants is in excess, the fluidic properties of the reaction mixture may change over the course of the reaction. Surface features may be used to provide a different geometry, pattern, angle, depth, or ratio of size relative to the cross-section of the process microchannel along its axial length to accommodate these hydrodynamic changes.

The separation between adjacent process microchannels, staged addition channels and/or heat exchange channels may be in the range from about 0.05 mm to about 50 mm, and in one embodiment about 0.1 to about 10 mm, and in one embodiment about 0.2 mm to about 2 mm.

The process microchannels and the staged addition channels may be formed from parallel spaced sheets and/or plates, the staged addition channels being adjacent to the process microchannels. The heat exchange channels may be formed from parallel spaced sheets and/or plates. The heat exchange channels may be adjacent to the process microchannels, the staged addition channels, or both the process microchannels and the staged addition channels. The process microchannels and staged addition channels may be aligned in interleaved side-by-side planes or interleaved planes stacked one above another.

The process microchannel and the staged addition channel may comprise circular tubes aligned concentrically. The process microchannel may be in an annular space and the staged addition channel may be in the center space or an adjacent annular space. The process microchannel may be in the center space and the staged addition channel may be in an adjacent annular space.

The reaction zone 220 in the process microchannel 210 may be characterized by having a bulk flow path. The term "bulk flow path" refers to an open path (contiguous bulk flow region) within the process microchannels. A contiguous bulk flow region allows rapid fluid flow through the process microchannels without large pressure drops. In one embodiment, the flow of fluid in the bulk flow region is laminar. Bulk flow regions within each process microchannel 210 may have a cross-sectional area in the range from about 0.05 to about 10,000 mm$^2$, and in one embodiment from about 0.05 to about 5000 mm$^2$, and in one embodiment from about 0.1 to about 2500 mm$^2$. The bulk flow regions may comprise from about 5% to about 95%, and in one embodiment from about 30% to about 80% of the cross-section of the process microchannels.

The apertures in the apertured section 250 and 250A may be of sufficient size to permit the flow of the second fluid stream through the apertured sections. The apertures may be referred to as pores. The apertured sections 250 and 250A containing the foregoing apertures may have thicknesses in the range from about 0.01 to about 50 mm, and in one embodiment about 0.05 to about 10 mm, and in one embodiment about 0.1 to about 2 mm. The apertures may have average diameters in the range up to about 250 microns, and in one embodiment up to about 100 microns, and in one embodiment up to about 50 microns, and in one embodiment in the range from about 0.001 to about 50 microns, and in one embodiment from about 0.05 to about 50 microns, and in one embodiment from about 0.1 to about 50 microns. In one embodiment, the apertures may have average diameters in the range from about 0.5 to about 10 nanometers (nm), and in one embodiment about 1 to about 10 nm, and in one embodiment about 5 to about 10 nm. The number of apertures in the apertured sections may be in the range from about 1 to about $5 \times 10^8$ apertures per square centimeter, and in one embodiment about 1 to about $1 \times 10^6$ apertures per square centimeter. The apertures may or may not be isolated from each other. A portion or all of the apertures may be in fluid communication with other apertures within the apertured section. That is, a fluid may flow from one aperture to another aperture. The ratio of the thickness of the apertured sections 250 and 250A to the length of the apertured sections along the flow path of the fluids flowing through the process microchannels 210 may be in the range from about 0.001 to about 1, and in one embodiment about 0.01 to about 1, and in one embodiment about 0.03 to about 1, and in one embodiment about 0.05 to about 1, and in one embodiment about 0.08 to about 1, and in one embodiment about 0.1 to about 1.

Figure 27:
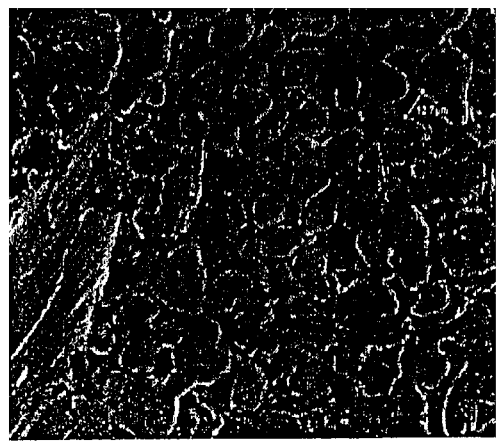
FIG. 27 is a scanning electron microscopic (SEM) image of a porous stainless steel substrate before being heat treated. This substrate may be used for making an apertured section which can be used to provide for flow between a staged addition channel and an adjacent process microchannel.
Figure 28:
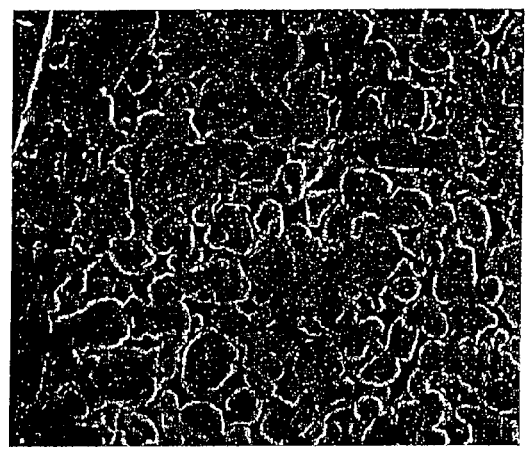
FIG. 28 is an SEM image of the substrate illustrated in FIG. 27 after being heat treated. This substrate may be used for making an apertured section which can be used to provide for flow between a staged addition channel and an adjacent process microchannel.

The apertured sections 250 and 250A may be constructed of any material that provides sufficient strength and dimensional stability to permit the operation of the inventive process. These materials include: steel (e.g., stainless steel, carbon steel, and the like); monel; inconel; aluminum; titanium; nickel; platinum; rhodium; copper; chromium; brass; alloys of any of the foregoing metals; polymers (e.g., thermoset resins); ceramics; glass; composites comprising one or more polymers (e.g., thermoset resins) and fiberglass; quartz; silicon; microporous carbon, including carbon nanotubes or carbon molecular sieves; zeolites; or a combination of two or more thereof. The apertures may be formed using known techniques such as laser drilling, microelectro machining system (MEMS), lithography electrodeposition and molding (LIGA), electrical sparkling, photochemical machining (PCM), electrochemical machining (ECM), electrochemical etching, and the like. The apertures may be formed using techniques used for making structured plastics, such as extrusion, or membranes, such as aligned carbon nanotube (CNT) membranes. The apertures may be formed using techniques such as sintering or compressing metallic powder or particles to form tortuous interconnected capillary channels and the techniques of membrane fabrication. The apertures may be reduced in size from the size provided by any of these methods by the application of coatings over the apertures internal side walls to partially fill the apertures. The selective coatings may also form a thin layer exterior to the porous body that provides the smallest pore size adjacent to the continuous flow path. The smallest average pore opening may be in the range from about one nanometer to about several hundred microns depending upon the desired droplet size for the emulsion. The apertures may be reduced in size by heat treating as well as by methods that form an oxide scale or coating on the internal side walls of the apertures. These techniques may be used to partially occlude the apertures to reduce the size of the openings for flow. FIGS. 27 and 28 show a comparison of SEM surface structures of a stainless steel porous substrate before and after heat treatment at the same magnification and the same location. FIG. 27 shows the surface before heat treating and FIG. 28 shows the surface after heat treating. The surface of the porous material after the heat treatment has a significantly smaller gap and opening size. The average distance between the openings is correspondingly increased.

Figure 29:
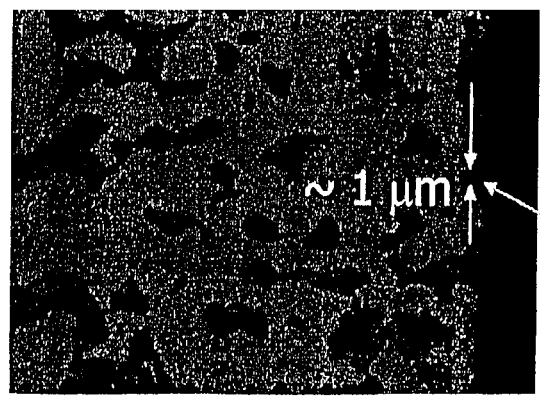
FIG. 29 is an SEM image of a tailored porous substrate which may be used for making an apertured section which can be used to provide for flow between a staged addition channel and an adjacent process microchannel.

The apertured sections 250 and 250A may be made from a metallic or nonmetallic porous material having interconnected channels or pores of an average pore size in the range from about 0.01 to about 1000 microns, and in one embodiment in the range from about 0.01 to about 200 microns. These pores may function as the apertures. The porous material may be made from powder or particulates so that the average inter-pore distance is similar to the average pore size. The porous material may be tailored by oxidization at a high temperature in the range from about 300° C. to about 1000° C. for a duration of about 1 hour to about 20 days, or by coating a thin layer of another material such as alumina by sol coating or nickel using chemical vapor deposition over the surface and the inside of pores to block the smaller pores, decrease pore size of larger pores, and in turn increase the inter-pore distance. An SEM image of a tailored substrate or apertured section is shown in FIG. 29.

The making of substrates for use as apertured sections 250 and 250A with sufficiently small micro-scale apertures or pores to provide a second fluid stream having bubble or droplet sizes smaller than about one micron can be problematic. One of the reasons for this lies in the fact that relatively high surface roughness occurs with untreated regular porous materials such as a metallic porous substrates made from powder/particles by compression and/or sintering. These metallic porous substrates typically do not have the required pore size in the surface region when a given nominal pore size is lower than a certain value. While the bulk of the porous material may have the specified nominal pore size, the surface region is often characterized by merged pores and cavities of much larger sizes. This problem can be overcome by tailoring these substrates to provide for the desired pore size and inter-pore distance in the surface region. This may be done by removing a surface layer from the porous substrate and adding a smooth new surface with smaller openings. The droplet size or bubble size of staged addition feed stream that may be formed using these tailored substrates may be reduced without increasing the pressure drop across the substrate. Since direct grinding or machining of the porous surface may cause smearing of the surface structure and blockage of the pores, the porous structure may be filled with a liquid filler, followed by solidification and mechanical grinding/polishing. The filler is then removed to regain the porous structure of the material. The filler may be a metal with a low melting point such as zinc or tin or the precursor of a polymer such as an epoxy. The liquid filling and removing steps may be assisted by the use of a vacuum. Grinding/polishing may be effected using a grinding machine and a grinding powder. Metal filler removal may be effected by melting and vacuum suction, or by acid etching. Epoxies or other polymers may be removed by solvent dissolution or by burn-off in air.

Figure 30:
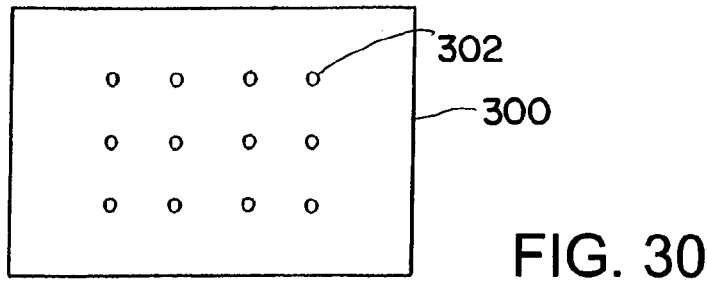
FIG. 30 is a schematic illustration of a plan view of an apertured sheet which may be used in making an apertured section. The apertured section may be used to provide for flow between a staged addition channel and an adjacent process microchannel.
Figure 31:
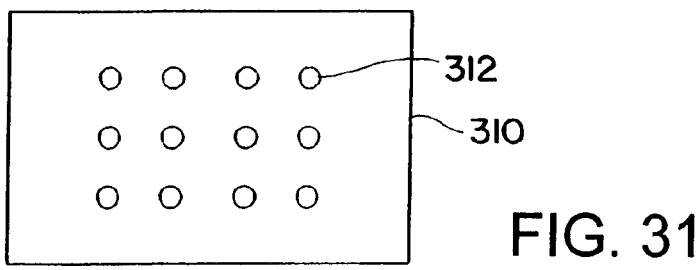
FIG. 31 is a schematic illustration of a plan view of an apertured sheet or plate which may be used in making an apertured section. The apertured section may be used to provide for flow between a staged addition channel and an adjacent process microchannel.
Figure 32:
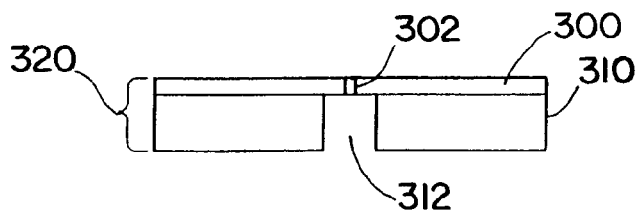
FIG. 32 is a schematic illustration of a relatively thin apertured sheet overlying a relatively thick apertured sheet or plate which may be used in making an apertured section. The apertured section may be used to provide for flow between a staged addition channel and an adjacent process microchannel.

Referring to FIGS. 30-32, the apertured sections 250 and 250A, in one embodiment, may be constructed of a relatively thin sheet 300 containing relatively small apertures 302, and a relatively thick sheet or plate 310 containing relatively large apertures 312. The sheet 300 and sheet or plate 310 may each be referred to as orifice plates. The apertures 312 may be aligned with or connected to the apertures 302. The relatively thin sheet 300 may overlie and be bonded to the relatively thick sheet or plate 310, the relatively thin sheet 300 facing the interior of process microchannel 210 and the relatively thick sheet 310 facing the interior of the staged addition channel 250 or 250A. The relatively thin sheet 300 may be bonded to the relatively thick sheet 310 using any suitable procedure (e.g., diffusion bonding) to provide a composite construction 320 with enhanced mechanical strength. The relatively thin sheet 300 may have a thickness in the range from about 0.001 to about 0.5 mm, and in one embodiment about 0.05 to about 0.2 mm. The relatively small apertures 302 may have any shape, for example, circular, triangular or rectangular. The relatively small apertures 302 may have an average diameter in the range from about 0.05 to about 50 microns, and in one embodiment about 0.05 to about 20 microns. The relatively thick sheet or plate 310 may have a thickness in the range from about 0.01 to about 5 mm, and in one embodiment about 0.1 to about 2 mm. The relatively large apertures 312 may have any shape, for example, circular, triangular or rectangular. The relatively large apertures 312 may have an average diameter in the range from about 0.01 to about 4000 microns, and in one embodiment about 1 to about 2000 microns, and in one embodiment about 10 to about 1000 micron. The total number of apertures 302 in sheet 300 and the total number of apertures 312 in sheet or plate 310 may be in the range from about 1 to about 10000 apertures per square centimeter, and in one embodiment from about 1 to about 1000 apertures per square centimeter. The sheet 300 and the sheet or plate 310 may be constructed of any of the materials described above as being useful for constructing the apertured sections 250 and 250A. The apertures 302 and 312 may be aligned or connected in such a manner that fluid flowing through the apertured sections 250 and 250A flows initially through the apertures 312 then through the apertures 302. The relatively short passageway for the fluid to flow through the relatively small apertures 302 enables the fluid to flow through the apertures 302 with a relatively low pressure drop as compared to the pressure drop that would occur if the passageway in the apertures had a depth equal to the combined depth of apertures 302 and 312.

Figure 33:
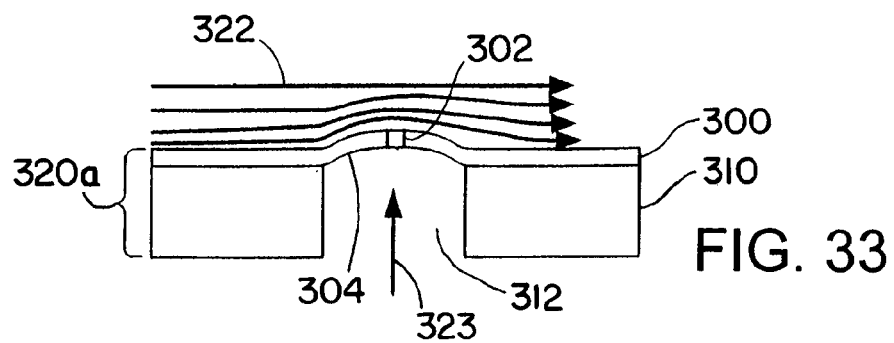
FIG. 33 is a schematic illustration of a relatively thin apertured sheet overlying a relatively thick apertured sheet or plate which may be used in making an apertured section. The apertured section may be used to provide for flow between a staged addition channel and an adjacent process microchannel. The relatively thin sheet has a convex portion that projects into the process microchannel.

In the embodiment illustrated in FIG. 33, the composite construction 320a has the same design as illustrated in FIG. 32 with the exception that convex portion 304 of the relatively thin sheet 300 covering the aperture 312 is provided. Convex portion 304 provides increased local shear force in the adjacent channel. The staged addition feed stream flows through the apertures 312 and 302 in the direction indicated by arrow 323. The directional arrows 322 in FIG. 33 show the flow of the feed composition in the process microchannel adjacent to the aperture 302. The increased local shear force leads to a smaller droplet size or gas bubble for the fluid flowing through the aperture 302.

Figure 34:
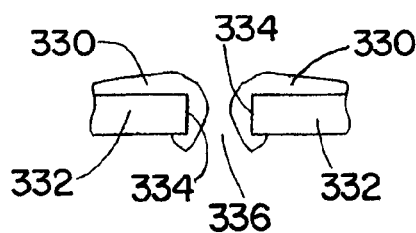
FIG. 34 is a schematic illustration of an alternate embodiment of an aperture that may be used an the apertured section. The apertured section may be used to provide for flow between a staged addition channel and an adjacent process microchannel. The aperture has a coating partially filling it and overlying its sidewalls.

In the embodiment illustrated in FIG. 34, a surface coating 330 is deposited on the surface of sheet or plate 332 and on the internal sidewalls 334 of aperture 336. This coating provides a facilitated way of reducing the diameter of the apertures. The coating material used to form coating 330 may be alumina, nickel, gold, or a polymeric material (e.g., Teflon). The coating 330 may be applied to the sheet or plate 332 using known techniques including chemical vapor deposition, metal sputtering, metal plating, sintering, sol coating, and the like. The diameter of the apertures may be controlled by controlling the thickness of the coating 330.

The apertured sections 250 and 250A may be formed from an asymmetric porous material, for example, a porous material having multiple layers of sintered particles. The number of layers may be two, three, or more. An advantage of these multilayered substrates is that they provide enhanced durability and adhesion. Examples include sintered ceramics that have relatively large pores on one side and relatively small pores on the other side. The relatively small pores may have diameters in the range of about 2 to about 10 nm. The relatively small pores may be positioned in a relatively thin layer of the multilayered substrate. The relatively thin layer may have a thickness in the range of about 1 to about 10 microns. The side with the relatively small pores may be placed facing the interior of the process microchannel 210 to take advantage of relatively high shear forces to remove the relatively small droplets of reactant and/or liquid catalyst as they are formed.

The apertured sections 250 and 250A may extend along at least about 5% of the axial length of the process microchannel 210, and in one embodiment at least about 20% of the axial length of the process microchannel, and in one embodiment at least about 35% of the axial length of the process microchannel, and in one embodiment at least about 50% of the axial length of the process microchannel, and in one embodiment at least about 65% of the axial length of the process microchannel, and in one embodiment at least about 80% of the axial length of the process microchannel, and in one embodiment at least about 95% of the axial length of the process microchannel, and in one embodiment from about 5% to about 100% of the axial length of the process microchannel, and in one embodiment from about 10% to about 95% of the axial length of the process microchannel, and in one embodiment from about 25% to about 75% of the axial length of the process microchannel, and in one embodiment from about 40% to about 60% of the axial length of the process microchannel 210.

The microchannel processing unit 100 may comprise one or more of the repeating units 200-200X illustrated in FIGS. 4-26 and 42-43. In one embodiment, the microchannel processing unit may comprise from 1 to about 50,000 of the repeating units, and in one embodiment from about 10 to about 50,000 of the repeating units, and in one embodiment from about 10 to about 30,000 repeating units, and in one embodiment from about 10 to about 10,000 of the repeating units, and in one embodiment from about 10 to about 5000 repeating units, and in one embodiment from about 10 to about 2000 repeating units, and in one embodiment from about 10 to about 1000 repeating units, and in one embodiment from about 10 to about 500 repeating units, and in one embodiment from about 10 to about 100 repeating units.

The inventive process may involve the use of non-Newtonian and/or Newtonian feed streams which may be used to form a non-Newtonian product. For example, when forming a non-Newtonian emulsion as the product, the following combinations of feed streams may be used:

| Case | Continuous Phase (Feed A) | Dispersed Phase (Feed B) | Product/emulsion |
| --- | --- | --- | --- |
| 1 | Newtonian | Newtonian | Non-Newtonian |
| 2 | Newtonian | Non-Newtonian | Non-Newtonian |
| 3 | Non-Newtonian | Newtonian | Non-Newtonian |
| 4 | Non-Newtonian | Non-Newtonian | Non-Newtonian |

Two approaches may be adopted for the design of the process fluid header 104. The header 104 may comprise one or more inlet manifolds for each of the inlet feed streams. When the inlet feed stream is a Newtonian fluid, the inlet feed stream may flow straight through the inlet manifold into the process microchannels without making any turns in the inlet manifold or the inlet feed stream may make one or more turns in the inlet manifold prior to entering the process microchannels. On the other hand, when the inlet feed stream is a non-Newtonian fluid, the inlet feed stream may flow through the inlet manifold directly into the process microchannels without making any turns in the inlet manifold. The same may be true with respect to the product footer 106, which may comprise an outlet manifold. When the product that is formed in the process microchannels is a non-Newtonian fluid, the product may flow directly through the footer 106 out of the microchannel processing unit 100. The footer 106 may comprise one or more straight through outlet manifolds wherein the fluid flows through the manifold without making any turns in the outlet manifold. Various manifold designs which may be used in the header 104 and footer 106 are disclosed in U.S. Patent Publication Nos. 2005/0087767 A1, 2006/0275185 A1, and 2006/0289662 A1, which are incorporated herein by reference.

Figure 62:
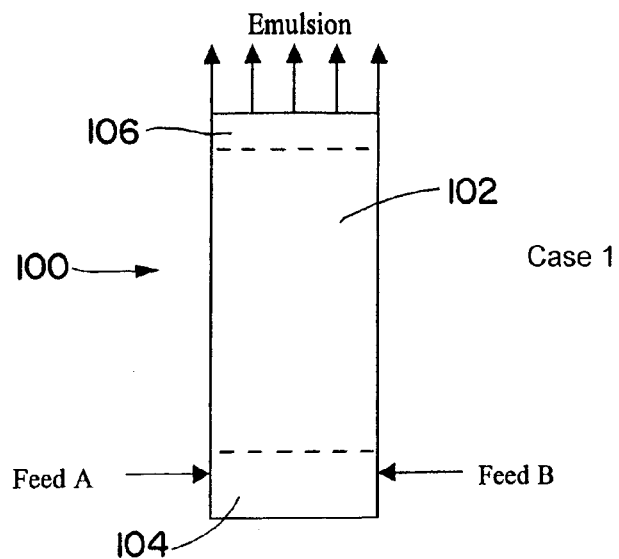
FIGS. 62 and 65-67 are schematic illustrations of microchannel processing units which may be used in accordance with the inventive process.
Figure 66:
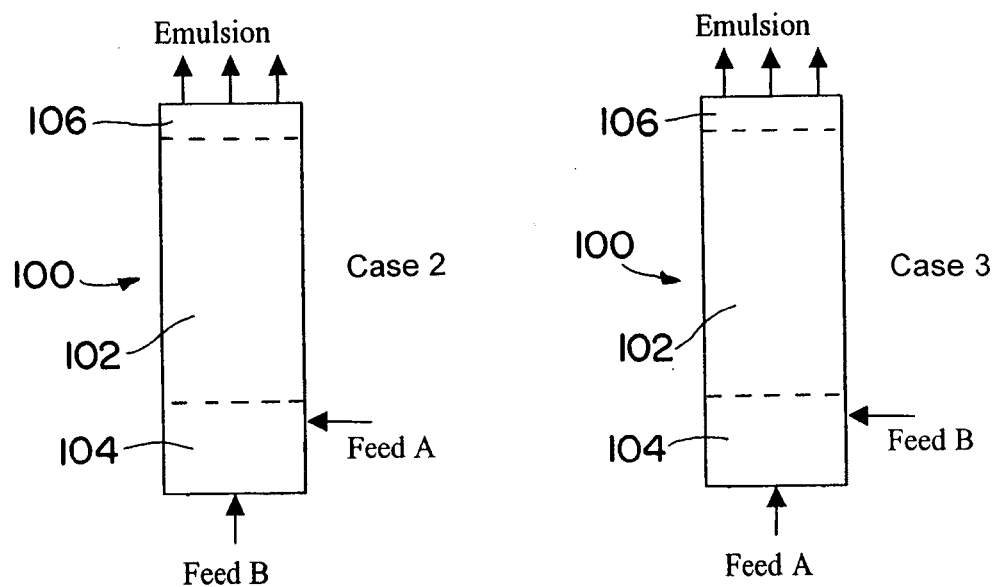
Figure 67:
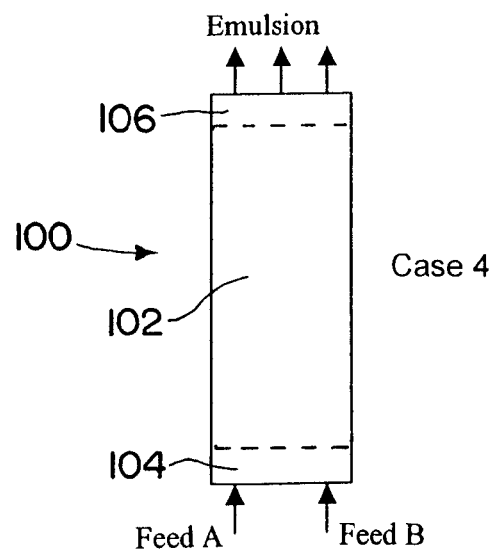

The flow patterns for Cases 1-4 referred to in the table above are illustrated in FIGS. 62, 66 and 67. In each of FIGS. 62, 66 and 67, a microchannel processing unit 100 is used. These are the same as the microchannel processing unit 100 illustrated in FIG. 3 with the exception that the headers disclosed in these figures are different. Each of these microchannel processing units comprise microchannel processing unit core 102, process fluid header 104 and product footer 106. Case 1 is illustrated in FIG. 62. Referring to FIG. 62, both feed streams A and B are Newtonian fluids which enter the header 104. The header 104 includes one or more inlet manifolds for each of the feed streams. Each of the feed streams enter the header from a side of the header and make one or more turns in the inlet manifolds to flow into the process microchannels in the microchannel processing unit core 102. The product emulsion, which is non-Newtonian, flows from the process microchannels directly through footer 106 out of the microchannel processing unit 100. The product may flow through one or more outlet manifolds in the footer 106 without making turns in the outlet manifold.

For Cases 2 and 3, the flow patterns are illustrated in FIG. 66. Referring to Case 2 in FIG. 66, the feed stream A, which is Newtonian, flows into the header 104 from a side of the header. The header includes at least one inlet manifold for each feed stream. Feed stream A makes at least one turn within the inlet manifold prior to entering the process microchannels. The feed stream B, which is non-Newtonian, flows directly through the inlet manifold in the header 104 into the process microchannels without making any turns in the inlet manifold. The feed streams A and B are mixed in the process microchannels to form the product emulsion which flows directly through the footer 106 and out of the microchannel processing unit 100. The product may flow through one or more outlet manifolds in the footer 106 without making any turns in the outlet manifolds.

Case 3, which is also illustrated in FIG. 66, is the same as Case 2 with the exception that the feed stream B is the Newtonian fluid which flows into the header 104 from a side of the header and into one or more inlet manifolds. Feed stream B makes one or more turns in the inlet manifolds prior to entering the process microchannels. The feed stream A, which is non-Newtonian, flows directly through one or more inlet manifolds in the header 104 without making any turns in the inlet manifolds. The product emulsion flows directly through the footer 106 and out of the microchannel processing unit 100. The product may flow through one or more outlet manifolds in the footer 106 without making any turns in the outlet manifolds.

Case 4, which is illustrated in FIG. 67, involves the use of inlet feed streams A and B, both of which are non-Newtonian. Both feed streams flow directly through the inlet manifolds in the header 104 without making any turns in the inlet manifolds. The product emulsion, which is non-Newtonian, flows directly through the footer 106 and out of the microchannel processing unit 104. The product may flow through one or more outlet manifolds in the footer 106 without making any turns in the outlet manifolds.

Figure 63:
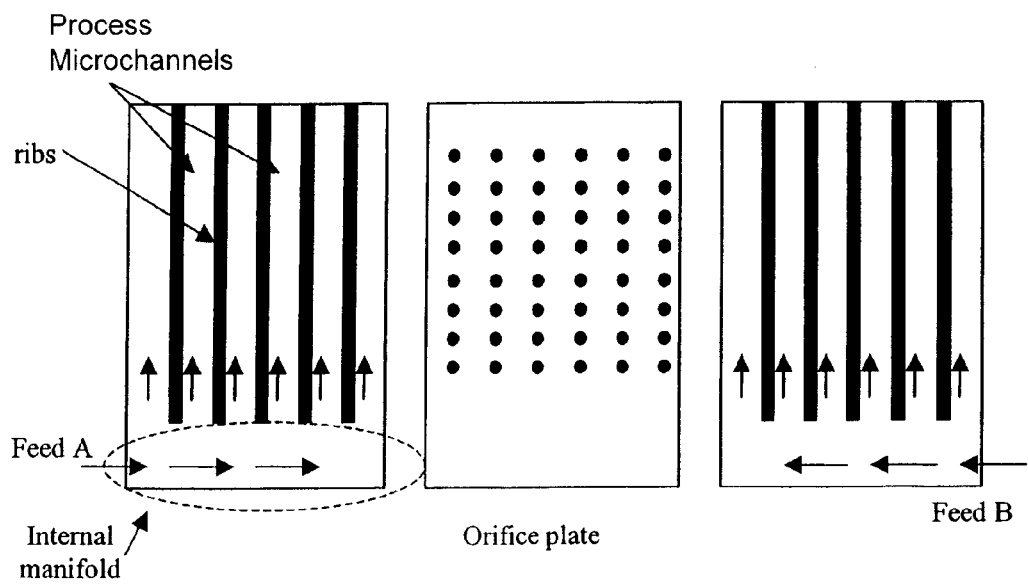
FIG. 63 is a schematic illustration of a pair of shims and an orifice plate which may be used for making a repeating unit that can be used in forming the microchannel processing unit illustrated in FIG. 62.

The microchannel device illustrated in FIG. 62 may be formed using the shims and orifice plate illustrated in FIG. 63. The shim on the left provides for the inlet and flow of feed stream A. The shim on the right provides for the inlet and flow of feed stream B. These shims may be stacked one above the other with the orifice plate illustrated in the center of FIG. 63 positioned between the shims. The two shims and orifice plate illustrated in FIG. 63 may comprise a single repeating unit which may be used to form the microchannel processing unit 100. Additional repeating units similar to the foregoing may be stacked one above the other. Additional shims providing for heat exchange channels 272 may be interleaved between the repeating units.

In order to control the distribution of feed from the inlet manifold to the process microchannels, flow resistors and/or flow distribution features may be provided in the manifold to control the distribution of flow from the inlet manifold to the process microchannels. A flow resistor may be an obstruction or an area of increased channel wall roughness that reduces the mass flow rate through the manifold. Examples of flow resistors that may be used are disclosed in the above-mentioned U.S. Patent Publications 2005/0087767 A1 and 2006/0275185 A1.

Figure 64:
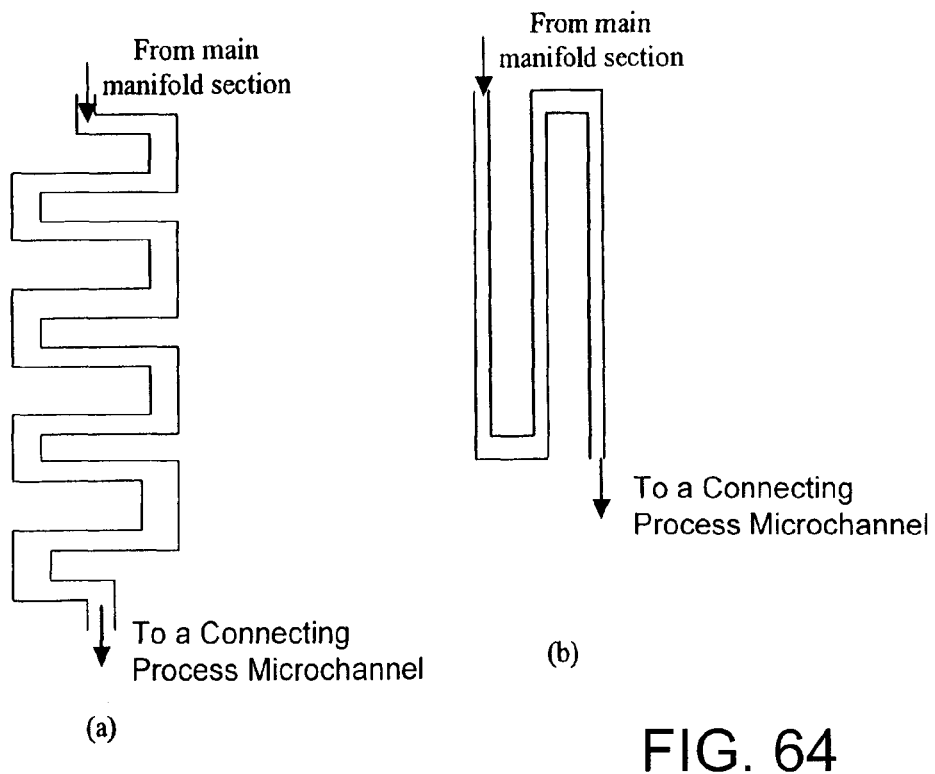
FIG. 64 is a schematic illustration of flow distribution features which may be used with the inventive process.

A flow distribution feature may be a micro-dimensioned channel connecting an inlet manifold to a process microchannel. Examples of connecting flow distribution features that may be used are illustrated in FIG. 64. In each of the illustrations provided in FIG. 64, a micro-dimensioned channel is shown which provides for the flow of fluid from the manifold to a process microchannels. These micro-dimensioned channels may have heights in the range from about 0.05 to about 10 mm, and in one embodiment from about 0.05 to about 5 mm, and widths in the range from about 0.05 to about 1 mm, and in one embodiment from about 0.05 to about 0.25 mm. The heights and widths may be aligned normal to the flow of fluid in the micro-dimensioned channels. The cross-sectional area of the flow distribution feature may be up to about 100 times smaller than the cross-sectional area of the process microchannel it is connected to, and in one embodiment up to about 50 times smaller, and in one embodiment up to about 10 times smaller, and in one embodiment up to about 2 times smaller. These micro-dimensioned channels may be useful when the pressure drops provided by the different feed streams flowing from the manifolds to the process microchannels are different. For example, the pressure drop for feed stream A may be three times smaller than the pressure drop for the feed stream B and flow distribution features may be used for the feed with the smaller pressure drop. Alternatively, flow resistors may be used for the feed streams with the lower pressure drops.

Figure 65:
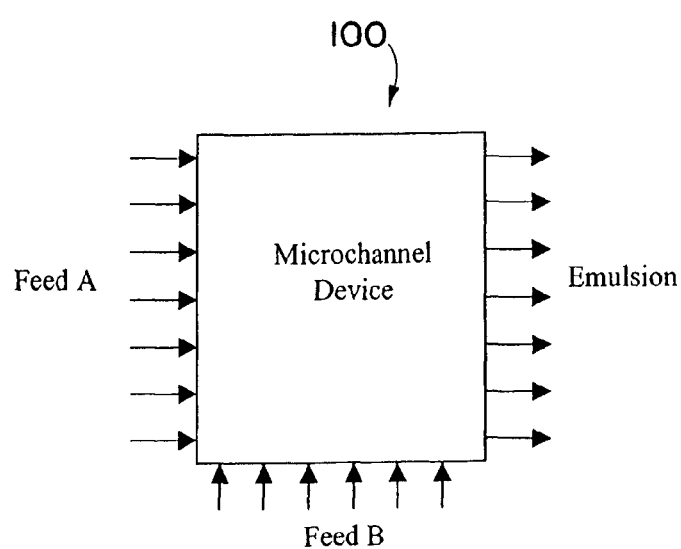

The feed streams may enter the microchannel processing unit 100 using a cross-flow orientation as illustrated in FIG. 65. Both feed streams A and B may enter the microchannel processing unit using one or more straight flow through inlet manifolds. This microchannel processing unit may be constructed using alternating shims and orifice plates as illustrated in FIG. 63, with the exception that the feed streams flow directly into the process microchannels, rather than through manifolds requiring at least one turn in the direction of flow as illustrated in FIG. 63.

Flow resistors and/or flow distribution features in the manifolds may be used to reduce sensitivities to manufacturing tolerances. The flow resistors and/or flow distribution features may reduce the sensitivity of overall pressure drop to manufacturing tolerance variations. Tight tolerances for manufacturing flow resistors and/or flow distribution features may be achieved by etching the flow resistors and/or flow distribution features in shims made from the same stock.

Figure 50:
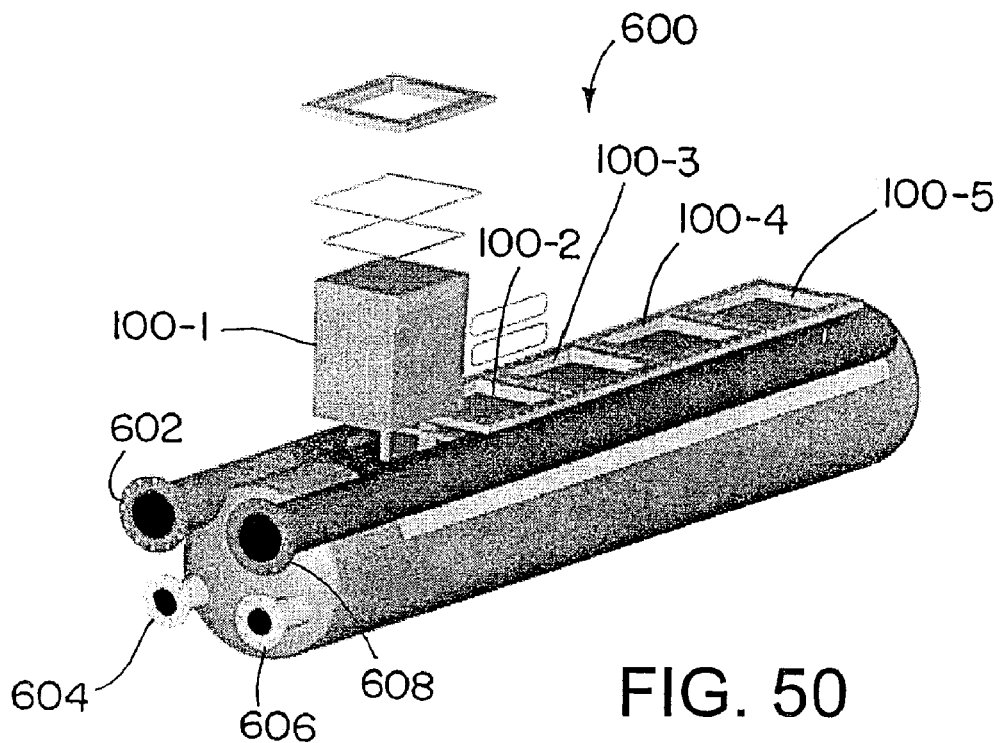
FIGS. 50 and 51 are schematic illustrations of a pressurizable vessel that may be used for housing microchannel processing units provided for in accordance with the invention.
Figure 51:
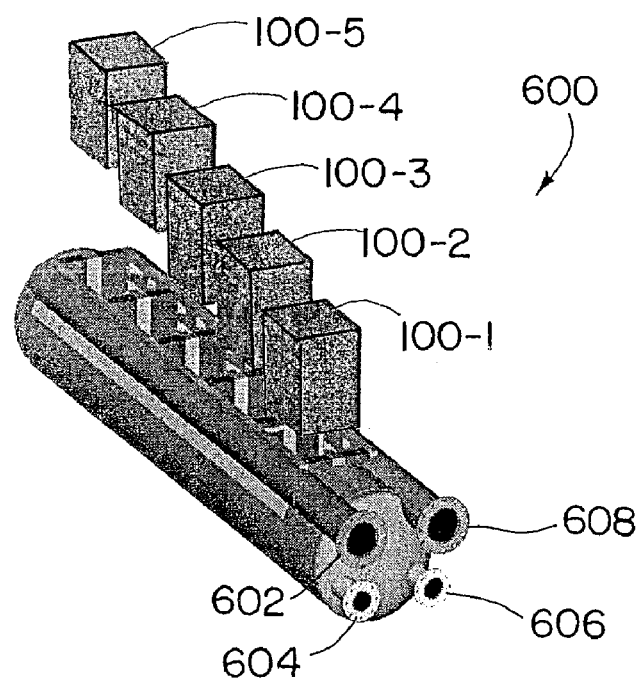

A plurality of the microchannel processing units 100 may be housed in vessel 600 which is illustrated in FIGS. 50 and 51. Referring to FIGS. 50 and 51, the vessel 600 contains five microchannel processing units 100. These are identified in FIGS. 50 and 51 as microchannel processing units 100-1, 100-2, 100-3, 100-4 and 100-5. Although five microchannel processing units 100 are disclosed in the drawings, it will be understood that the vessel 600 may contain any desired number of microchannel processing units. For example, the vessel 600 may contain from 1 to about 1000 microchannel processing units 100, and in one embodiment from about 3 to about 500 microchannel processing units 100, and in one embodiment from about 3 to about 250 microchannel processing units 100, and in one embodiment from about 3 to about 150 microchannel processing units 100, and in one embodiment from about 5 to about 50 microchannel processing units 100, and in one embodiment from about 5 to about 12 microchannel processing units 100. In one embodiment, the vessel 600 may contain from 1 to about 50 microchannel processing units 100, and in one embodiment from 1 to about 20 microchannel processing units 100. Each microchannel processing unit 100 may comprise from about 1 to about 50,000 process microchannels, and in one embodiment from about 10 to about 50,000 process microchannels, and in one embodiment from about 10 to about 30,000, and in one embodiment from about 10 to about 10,000 process microchannels. The vessel 600 may be a pressurizable vessel. The vessel 600 includes inlets 602 and 604, and outlets 606 and 608. The inlet 602 is connected to a manifold which may be provided for flowing the first fluid to the process microchannels in the microchannel processing units 100-1, 100-2, 100-3, 100-4 and 100-5. The inlet 604 is connected to a manifold which may be provided for flowing heat exchange fluid to the heat exchange channels in the microchannel processing units 100-1, 100-2, 100-3, 100-4 and 100-5. The outlet 706 is connected to a manifold which may be provided for flowing product from the microchannel processing units 100-1, 100-2, 100-3, 100-4 and 100-5 out of the vessel 600. The inlet 608 is connected to a manifold which may provide for the flow of the second fluid to staged addition channels that may be in the microchannel processing units 100-1, 100-2, 100-3, 100-4 and 100-5. The vessel 600 also includes an outlet (not shown in the drawings) providing for the flow of heat exchange fluid from the microchannel processing units 100-1, 100-2, 100-3, 100-4 and 100-5.

The vessel 600 may be constructed from any suitable material sufficient for operating under the pressures and temperatures required for operating the microchannel reactors. For example, the shell and heads of the vessels 600 may be constructed of cast steel. The flanges, couplings and pipes may be constructed of stainless steel or other suitable alloys. The vessel 600 may have any desired diameter, for example, from about 30 to about 500 cm, and in one embodiment from about 100 to about 300 cm. The axial length of the vessel 600 may be of any desired value, for example, from about 0.5 to about 50 meters, and in one embodiment from about 0.5 to about 15 meters, and in one embodiment from about 1 to about 10 meters.

As indicated above, the microchannel processing units 100 may comprise a plurality of process microchannels, heat exchange channels and optionally staged addition channels stacked one above the other or positioned side-by-side. The microchannel processing units 100 may be in the form of cubic blocks as illustrated in FIGS. 50 and 51. Each of these cubic blocks may have a length, width and height. The length may be in the range from about 10 to about 1000 cm, and in one embodiment in the range from about 50 to about 200 cm. The width may be in the range from about 10 to about 1000 cm, and in one embodiment in the range from about 50 to about 200 cm. The height may be in the range from about 10 to about 1000 cm, and in one embodiment in the range from about 50 to about 200 cm.

The inventive process may be suitable for conducting any chemical reaction wherein one or more of the reactants and/or products is an non-Newtonian fluid. These may include gas-liquid reactions, liquid-liquid reactions, gas-liquid-liquid reactions, gas-liquid-solid reactions, liquid-liquid-solid reactions, and the like. The reactions that may be conducted in accordance with the inventive process may include any fluid reaction including oxidation reactions, hydrocracking reactions, hydrogenation reactions, hydration reactions, carbonylation reactions, sulfation reactions, sulfonation reactions, oligomerization reactions, polymerization reactions, and the like.

A first reactant may comprise one or more liquids. When the first reactant comprises more than one liquid, the resulting liquid mixture may be in the form of a solution or a multiphase fluid mixture (for example, an emulsion). The first reactant may comprise solids dispersed in one or more of the fluids. The solids may comprise catalytic particulates. Alternatively the solids may not be catalytic. The solids may be added to provide a desired product texture, adsorb wanted or unwanted by-products, intensify shear with the process microchannel, etc. The solids may be of any size provided they are small enough to be in the process microchannels. For example, the solids may have a median particle diameter in the range from about 0.01 to about 200 microns, and in one embodiment from about 1 to about 40 microns.

A second reactant may comprise one or more liquids, one or more gases, or a mixture thereof. The second reactant may comprise one or more gases containing dispersed liquid droplets or one or more liquids containing dispersed gas bubbles. The second reactant, when in the form of a gas and introduced into the first reactant to form a multiphase reaction mixture, may form gas bubbles in the first reactant. The second reactant, when in the form of a liquid and introduced into the first reactant to form a multiphase reaction mixture, may form liquid droplets in the first reactant. When in liquid form, the second reactant may be immiscible with the first reactant. Alternatively, the multiphase reaction mixture may comprise a foam where a thin liquid film covers entrapped gas. The foam may comprise a continuous or discontinuous foam structure.

The purity of the reactants may not be critical, though it is desirable to avoid the presence of compounds which may poison the catalyst. The reactants may comprise impurities that are not reactive with the reactants.

The first and/or second reactants may be combined with one or more diluent materials. Examples of such diluents include nitrogen, helium, non-reactive hydrocarbon diluents, and the like. The diluent concentration of each of the reactants may range from zero to about 99% by weight, and in one embodiment from zero to about 75% by weight, and in one embodiment from zero to about 50% by weight. Diluents may be combined with one or more of the reactants when the reactant is in gaseous form and it is desired to use a liquid as the reactant. Diluents may be used to reduce the viscosity of viscous liquid reactants. An advantage of at least one embodiment of the invention is that without the use of such diluents a more efficient and compact process may be provided.

The catalyst may be an oxidation catalyst, hydrocracking catalyst, hydrogenation catalyst, hydration catalyst, carbonylation catalyst, sulfation catalyst, sulfonation catalyst, oligomerization catalyst, polymerization catalyst, or a combination of two or more thereof.

The oxidation reactions may involve the reaction, in the presence of one or more oxidation catalysts, of one or more hydrocarbon compounds that are capable of undergoing an oxidation reaction with oxygen or a source of oxygen. The hydrocarbon compounds, which may be referred to as the first reactant, may be in the form of liquids, or they may be in the form of gases dispersed in one or more liquids. The oxygen or oxygen source, which may be referred to as the second reactant, may be in the form of a gas.

The hydrocarbon compounds that may be used in the oxidation reactions include saturated aliphatic compounds (e.g., alkanes), unsaturated aliphatic compounds (e.g., alkenes, alkynes), aldehydes, alkyl substituted aromatic compounds, alkylene substituted aromatic compounds, and the like. The saturated aliphatic compounds include alkanes containing 1 to about 25 carbon atoms per molecule, and in one embodiment 1 to about 20 carbon atoms, and in one embodiment 1 to about 10 carbon atoms. These include straight chain alkanes, single and multiple branched chain alkanes, and cyclic alkanes including cyclic alkanes having one or more alkyl groups attached to the ring. These include methane, ethane, propane, isopropane, butane, isobutane, pentane, cyclopentane, hexane, heptane, octane, 2-ethylhexane, nonane, decane, dodecane, and the like. The unsaturated aliphatic compounds include alkenes or alkylenes, and alkynes. The unsaturated aliphatic compounds may contain from 2 to about 25 carbon atoms, and in one embodiment about 2 to about 20 carbon atoms, and in one embodiment about 2 to about 10 carbon atoms. These include straight chain alkenes, single and multiple branched chain alkenes, and cyclic alkenes including cyclic alkenes having one or more alkyl and/or alkene groups attached to the ring. These include ethylene; propylene; 1-butene; 2-butene; isobutylene; 1-pentene; 2-pentene; 3-methyl-1-butene; 2-methyl-2-butene; 1-hexene; 2,3-dimethyl-2-butene; 1-heptene; 1-octene; 1-nonene; 1-decene; 1-dodecene; and the like.

The unsaturated aliphatic compounds may comprise polyenes. These include dienes, trienes, and the like. These compounds may contain from 3 to about 25 carbon atoms per molecule, and in one embodiment 3 to about 20 carbon atoms, and in one embodiment about 3 to about 10 carbon atoms. Examples include 1,2-propadiene (also known as allene); 1,3-butadiene; 2-methyl-1,3-butadiene (also known as isoprene); 1,3-pentadiene; 1,4-pentadiene; 1,5-hexadiene; 2,4-hexadiene; 2,3-dimethyl-1,3-butadiene; and the like.

The aldehydes may be saturated or unsaturated. They may be aliphatic and/or aromatic. The aldehydes may contain from 2 to about 25 carbon atoms per molecule, and in one embodiment about 2 to about 20 carbon atoms, and in one embodiment about 2 to about 10 carbon atoms. Examples include formaldehyde; acetaldehyde; propionaldehyde; n-butyraldehyde; n-valeraldehyde; caproaldehyde; acrolein; tran-2-cis-6-nonadienal; n-heptylaldehyde; trans-2-hexenal; hexadeconal; benzaldehyde; phenylacetaldehyde; o-tolualdehyde; m-tolualdehyde; p-tolualdehyde; salicylaldehyde; p-hydroxybenzaldehyde; and the like.

The alkyl or alkylene substituted aromatic compounds may contain one or more alkyl or alkylene substituents. These compounds may be monocyclic (e.g., phenyl) or a polycyclic (e.g., naphthyl). These compounds include alkyl substituted aromatic compounds containing one or more alkyl groups containing 1 to about 25 carbon atoms, and in one embodiment 1 to about 20 carbon atoms, and in one embodiment 1 to about 10 carbon atoms. These also include the alkylene substituted aromatic compounds containing one or more alkylene groups containing 2 to about 25 carbon atoms, and in one embodiment 2 to about 20 carbon atoms, and in one embodiment 2 to about 10 carbon atoms. Examples include toluene, o-xylene, m-xylene, p-xylene, hemimellitene, pseudocumene, mesitylene, prehnitene, isodurene, durene, pentamethylbenzene, hexamethylbenzene, ethylbenzene, n-propylbenzene, cumene, n-butylbenzene, isobutylbenzene, sec-butylbenzene, tert-butylbenzene, p-cymene, styrene, and the like.

The oxygen or oxygen source used in the oxidation reactions may comprise molecular oxygen, air or other oxidants, such as nitrogen oxides, which can function as a source of oxygen. The oxygen source may be carbon dioxide, carbon monoxide or a peroxide (e.g., hydrogen peroxide). Gaseous mixtures containing oxygen, such as mixtures of oxygen and air, or mixtures of oxygen and an inert gas (e.g., helium, argon, etc.) or a diluent gas (e.g., carbon dioxide, water vapor, etc.) may be used. The oxygen source may comprise oxygen enriched air.

The mole ratio of the hydrocarbon reactant to oxygen may be in the range from about 0.2:1 to about 8:1, and in one embodiment about 0.5:1 to about 4:1, and in one embodiment about 1:1 to about 3:1. In one embodiment, the mole ratio may be about 2:1 or higher, and in one embodiment about 2.5:1 or higher. In one embodiment, the mole ratio may be about 1.8 or less.

The oxidation catalyst may comprise any catalyst that is useful as an oxidation catalyst. The catalyst may comprise a metal, metal oxide or mixed metal oxide of one or more of Mo, W, V, Nb, Sb, Sn, Pt, Pd, Cs, Zr, Cr, Mg, Mn, Ni, Co, Ce, or a mixture of two or more thereof. These catalysts may also comprise one or more alkali metals or alkaline earth metals or other transition metals, rare earth metals, or lanthanides. Additionally elements such as P and Bi may be present. The catalyst may be supported, and if so, useful support materials include metal oxides (e.g., alumina, titania, zirconia), silica, mesoporous materials, zeolites, refractory materials, or combinations of two or more thereof. The form which these catalysts may be in is discussed in greater detail below.

The product formed by the oxidation reaction may comprise one or more oxygenates. The term "oxygenate" is used herein to refer to a hydrocarbon compound that contains at least one oxygen. The oxygenates include alcohols, epoxides, aldehydes, ketones, carboxylic acids, carboxylic acid anhydrides, esters, and the like. The oxygenates include, with the exception of the epoxides and esters, one or more of the above-indicated oxygenates containing 1 to about 25 carbon atoms per molecule, and in one embodiment 1 to about 20 carbon atoms, and in one embodiment 1 to about 10 carbon atoms. The epoxides and esters must contain at least 2 carbon atoms, but in all other respects would include compounds within the above-indicated ranges, for example, 2 to about 25 carbon atoms, etc. The alcohols include monools and polyols. Specific examples include methanol, ethyl alcohol, propyl alcohol, butyl alcohol, isobutyl alcohol, pentyl alcohol, cyclopentyl alcohol, crotyl alcohol, hexyl alcohol, cyclohexyl alcohol, allyl alcohol, benzyl alcohol, glycerol, and the like. The epoxides include ethylene oxide, propylene oxide, butylene oxide, isobutylene oxide, cyclopentene oxide, cyclohexene oxide, styrene oxide, and the like. The aldehydes include formaldehyde; acetaldehyde; propionaldehyde; n-butyraldehyde; n-valeraldehyde; caproaldehyde; acrolein; tran-2-cis-6-nonadienal; n-heptylaldehyde; trans-2-hexenal; hexadeconal; benzaldehyde; phenylacetaldehyde; o-tolualdehyde; m-tolualdehyde; p-tolualdehyde; salicylaldehyde; p-hydroxybenzaldehyde; and the like. The ketones include acetone, methyl ethyl ketone, 2-pentanone, 3-pentanone, 2-hexanone, 3-hexanone, cyclohexanone, methyl isobutyl ketone, acetophenone, propiophenone, n-butyrophenone, benzophenone, and the like. The carboxylic acids include formic acid, acetic acid, propionic acid, butyric acid, isobutyric acid, valeric acid, caproic acid, caprylic acid, capric acid, acrylic acid, methacrylic acid, benzoic acid, toluic acid, phthalic acid, salicylic acid, and the like. The carboxylic acid anhydrides include acetic anhydride, maleic anhydride, phthalic anhydride, benzoic anhydride, and the like. The carboxylic acids and anhydrides include hydrocarbon substituted carboxylic acids and anhydrides (e.g., hydrocarbon substituted succinic acids and anhydrides) wherein the hydrocarbon substituent contains from 1 to about 500 carbon atoms, and in one embodiment about 20 to about 500 carbon atoms. The esters include methyl acetate, vinyl acetate, ethyl acetate, n-propyl acetate, n-butyl acetate, n-pentyl acetate, isopentyl acetate, benzyl acetate, phenyl acetate, and the like.

The hydrocracking reactions may involve destructive hydrogenation (also known as hydrogenolysis) of large hydrocarbon molecules wherein the large or heavy hydrocarbon molecules are broken down to smaller or lighter ones and reacted with hydrogen. The hydrocarbon reactant may be referred to as the first reactant and the hydrogen may be referred to as the second reactant. The terms "light" and "heavy" are used herein in their normal sense within the refining industry to refer respectively to relatively low and high boiling point ranges. The hydrocarbon reactant may comprise any hydrocarbon requiring hydrocracking. The hydrocarbon reactant may vary from naptha to heavy crude oil residual fractions. The hydrocarbon reactant may have a 5% by volume boiling point above about 350° F. (177° C.), and in one embodiment above about 400° F. (204° C.). In one embodiment, at least about 90% by volume of the hydrocarbon reactant may fall within the boiling point range of about 300° F. (149° C.) to about 1050° F. (566° C.), and in one embodiment between about 600° F. (316° C.) to about 1000° F. (538° C.). The hydrocarbon reactant may comprise one or more petroleum fractions such as atmospheric and vacuum gas oils (AGO and VGO).

The hydrocarbon reactant may comprise heavy hydrocarbonaceous mineral or synthetic oils or a mixture of one or more fractions thereof. The hydrocarbon reactant may comprise one or more straight run gas oils, vacuum gas oils, demetallized oils, deasphalted vacuum residues, coker distillates, cat cracker distillates, shale oils, tar sand oils, coal liquids, or a mixture of two or more thereof.

The hydrogen used in the hydrocracking reactions may be in the form of hydrogen gas or it may be in a hydrogen feed stream that further comprises water, methane, carbon dioxide, carbon monoxide and/or nitrogen. The hydrogen may be taken from a process stream of another process such as a steam reforming process (product stream with $H_2/CO$ mole ratio of about 3), a partial oxidation process (product stream with $H_2/CO$ mole ration of about 2), an autothermal reforming process (product stream with $H_2/CO$ mole ratio of about 2.5), a $CO_2$ reforming process (product stream with $H_2/CO$ mole ratio of about 1), a coal gasification process (product stream with $H_2/CO$ mole ratio of about 1), and combinations thereof. With each of these hydrogen sources, the hydrogen may be separated from the remaining ingredients using conventional techniques such as membrane separation or adsorption.

The mole ratio of hydrocarbon reactant to hydrogen in these hydrocracking reactions may be in the range from about 0.1:1 to about 10:1, and in one embodiment about 0.5:1 to about 5:1.

The hydrocracking catalyst may be any hydrocracking catalyst. These include zeolite catalysts including beta zeolite, omega zeolite, L-zeolite, ZSM-5 zeolites and Y-type zeolites. The catalyst may include a refractory inorganic oxide such as alumina, magnesia, silica, tilania, zirconia and silica-alumina. The catalyst may comprise a hydrogenation component. Examples of suitable hydrogenation components include metals of Group IVB and Group VIII of the Periodic Table and compounds of such metals. Molybdenum, tungsten, chromium, iron, cobalt, nickel, platinum, palladium, iridium, osmium, rhoduim and ruthenium may be used as the hydrogenation component. These catalysts are described in U.S. Pat. No. 6,312,586 B1, which is incorporated herein by reference.

The product made by the hydrocracking process may be a middle distillate fraction boiling in the range from about 260 to about 700° F. (127-371° C.). The term "middle distillate" is intended to include the diesel, jet fuel and kerosene boiling range fractions. The terms "kerosene" and "jet fuel" boiling range are intended to refer to a temperature range of 260-550° F. (127-288° C.) and "diesel" boiling range is intended to refer to hydrocarbon boiling points from about 260 to about 700° F. (127-371° C.). The distillate product may be a gasoline or naphtha fraction. These may be considered to be the $C_5$ to 400° F. (204° C.) endpoint fractions.

The hydrogenation reactions may involve the reaction, in the presence of one or more hydrogenation catalysts, of one or more hydrocarbon compounds that are capable of undergoing a hydrogenation reaction with hydrogen. The hydrocarbon compounds may be referred to as the first reactant. These hydrocarbon compounds may be in the form of liquids, or they may be in the form of gases dispersed in liquids. The liquid may comprise the reactant and one or more additional solvents. The solvents may be solvents for one or more reactants and/or products. The hydrogen may be referred to as the second reactant, and may be in the form of a gas. The hydrogen may be derived from any of the above mentioned sources.

The hydrocarbon compounds that may undergo a hydrogenation reaction include the unsaturated hydrocarbon compounds discussed above. The hydrocarbon compounds include unsaturated fats and oils. The fats and oils may be derived from animal or vegetable sources. The fats and oils include triglycerides, that is, esters of glycerol and fatty acids. The fatty acids may be monounsaturated or polyunsaturated. Examples of the fatty acids in the fats and oils include oleic acid, linoleic acid, linolenic acid, and the like.

The mole ratio of unsaturated hydrocarbon reactant to hydrogen in these hydrogenation reactions may be in the range from about 0.1:1 to about 10:1, and in one embodiment about 0.5:1 to about 5:1.

The hydrogenation catalyst may be hydrogenation any catalyst. These include metals of Group IVB and Group VIII of the Periodic Table and compounds of such metals. Molybdenum, tungsten, chromium, iron, cobalt, nickel, platinum, palladium, iridium, osmium, rhodium, rhenium, and ruthenium may be used. In one embodiment, the catalyst may comprise palladium coated on the walls of the process microchannel or adhered to a fixed support within the process microchannel. The form in which these catalysts may be in is discussed in greater detail below.

The product made by the hydrogenation process may be a saturated or partially saturated hydrocarbon corresponding to the unsaturated hydrocarbon compounds used as the first reactant.

The process may be used to hydrogenate vegetable oils to increase their degree of saturation to produce edible fat products such as margarines. The improved mass transfer resulting from the inventive process may also improve the selectivity of the process to reduce the amount of unwanted conversion of cis isomers of triglycerides to trans isomers. This invention may improve the formation of the trans isomer from about 30% to about 50% by weight which may be obtained using conventional technology (i.e., non-microchannel process technology) to less than about 15% by weight, and in one embodiment less than about 10% by weight, and in one embodiment less than about 8% by weight. The process may use a hydrogenation catalyst. The catalyst may be in the form of a slurry, particulate solids or a fixed bed.

In one embodiment, the hydrogenation process may involve use of a catalyst (for example a precious metal such as palladium) fixed on the interior walls of the process microchannels or on a support structure positioned within the process microchannels. This may eliminate the need for a filtration step. This may also result in safer (no catalyst contamination), higher purity products. Precious metals catalysts such as palladium may be more reactive than prior art nickel catalysts and as such may effect the hydrogenation reactions at lower temperatures than conventionally used. This combined with the improved heat transfer resulting from the inventive process may significantly reduce the formation of secondary products that typically form as a result of thermal decomposition of oils and fats. This also may improve the quality of the food product. Unlike conventional nickel catalysts, the use of a palladium catalyst at reduced hydrogenation temperatures may decrease the concentration of hazardous trans-isomers, especially using high conversions which may be achieved at relatively short contact times pursuant to the inventive process. Improved mass transfer resulting from the inventive process may also improve the selectivity of the process. Improved heat and mass transfer may improve catalyst stability and turn-over frequency. This may result in a lower catalyst requirement. This may be beneficial when using precious metals because of the low operating temperature and pressure. In one embodiment, the catalyst may comprise nano-scale size particles of a precious metal such as palladium dispersed on the walls of the process microchannels and/or surface features or on a catalytic support such as a fin assembly insert using a dispersing/binding agent such as a colloidal metal oxide, carbon black, furfural alcohol, etc. The catalyst may be made using micro-shapes coated with catalytic metals that fill the void space of the microchannels.

The hydration reactions may involve the reaction, in the presence of a hydration catalyst, of an unsaturated hydrocarbon compound with water to form an alcohol or an ether. The unsaturated hydrocarbon compound, which may be referred to as the first reactant, may be any of the unsaturated hydrocarbon compounds discussed above. The water, which may be referred to as the second reactant, may be taken from any convenient source. The water may be deionized or purified using osmosis or distillation. The mole ratio of unsaturated hydrocarbon to water may be in the range from about 0.1 to about 10, and in one embodiment about 0.5 to about 5.

The hydration catalyst may comprise a solid acid catalyst such as zeolite; an acidic ion exchange resin containing sulfonate groups or the like; an inorganic oxide such as hydrated niobium oxide, hydrated tantalum oxide, zirconium dioxide, titanium dioxide, aluminum oxide, silicon dioxide, or a mixed oxide thereof; or an ion exchange type layered compound obtained by treating a layered compound such as smectite, kaolinite or vermiculite with at least one metal oxide selected from oxides of aluminum, silicon, titanium and zirconium. The catalyst may comprise aluminosilicates such as mordenite, faujasite, clinoptilite, L type zeolite, chabazite, erionite and ferrierite, as well as zeolite products ZSM-5, ZSM-4, ZSM-8, ZSM-11, ZSM-12, ZSM-20, ZSM-40, ZSM-35 and ZSM-48. The catalyst may comprise an element-containing zeolite such as borosilicate, gallosilicate and ferroaluminosilicate. These zeolites may contain thorium, copper, silver, chromium, molybdenum, tungsten, titanium, zirconium, hafnium and like metals. A proton exchange type (H type) zeolite may be used, and a portion thereof may be exchanged with a cationic species selected from alkali elements such as Na, K and Li, alkaline earth elements such as Mg, Ca and Sr and Group VIII elements such as Fe, Co, Ni, Ru or Pd. The form in which the catalyst may be in is discussed in greater detail below.

The carbonylation reactions may involve the reaction of a saturated or unsaturated hydrocarbon with carbon monoxide in the presence of a carbonylation catalyst. The saturated or unsaturated hydrocarbon reactant, which may be referred to as the first reactant, may be any of the saturated or unsaturated hydrocarbons discussed above. The carbon monoxide, which may be referred to as the second reactant, may be taken from any source. The carbon monoxide may be taken from a process stream such as a steam reforming process (product stream with $H_2/CO$ mole ratio of about 3), a partial oxidation process (product stream with $H_2/CO$ mole ratio of about 2), an autothermal reforming process (product stream with $H_2/CO$ mole ratio of about 2.5), a $CO_2$ reforming process (product stream with $H_2/CO$ mole ratio of about 1), a coal gasification process (product stream with $H_2/CO$ mole ratio of about 1), and combinations thereof. With each of these carbon monoxide sources, the carbon monoxide may be separated from the remaining ingredients using conventional techniques such as membranes or adsorption.

The mole ratio of hydrocarbon reactant to carbon monoxide in these carbonylation reactions may be in the range from about 0.5:1 to about 20:1, and in one embodiment about 2:1 to about 10:1.

The carbonylation catalyst may be any carbonylation catalyst. These include solid acid catalysts. The catalyst may be a solid comprising interacting protic and Lewis acid sites. The catalyst may comprise a combination of a Bronsted (protonic) acid and a Lewis acid. Examples include sulfated metal oxides (e.g., sulfated zirconia), fluorocarbon sulfonates $(B(CF_2)_nBSO_3H)$ in combination with supports (e.g., metal oxides and carbon), heteropolyacids, halides of Ta, Sb, Ga and B, halogenated metal oxides, sulfated zeolites, halides of Ta, Sb, Ga and B in combination with fluorosulfonic acid resins. The metal oxides include both single component oxides and multi-component oxides, i.e., mixed metal oxides. Single component metal oxides include aluminas, silicas, zirconia, titania and mixtures thereof. The mixed metal oxides can be either physical mixtures or structurally connected. Example of mixed metal oxides include ZrCTi, WCZr, TiCCu, TiCZn, TiCSi, AlCZr, FeCZr and TiCMn oxides. Examples include sulfated zirconia, sulfated titania, sulfated tungsten oxide, $BF_3$ on fluorinated alumina, aluminum chloride on chlorinated alumina, $H_3PW_{10}O_{40}$, $Cs_{2.5}H_{0.5}PW_{12}O_{40}$, $H_4SiW_{12}O_{40}$, and the like. The form in which the catalyst may be in is discussed in greater detail below.

The sulfonation reactions may involve the substitution of —$SO_3H$ groups (from sulfuric acid) for hydrogen atoms, for example, conversion of benzene, $C_6H_6$, into benzenesulfonic acid, $C_6H_5SO_3H$. The sulfonation procedures that may be used include the reaction of aromatic hydrocarbons with sulfuric acid, sulfur trioxide, or chlorosulfuric acid; the reaction of organic halogen compounds with inorganic sulfites; and the oxidation of certain classes of organic sulfur compounds, for example, thiols or disulfides.

Concentrated sulfuric acid, fuming sulfuric acid, chlorosulfonic acid, sulfuric anhydride, adducts of dioxane with $SO_3$, adducts of amine with $SO_3$, etc. may be used as agents for sulfonating aromatic compounds by introducing a sulfonic acid group into the aromatic ring of the compound. Aromatic amine compounds may be sulfonated by preparing an acidic sulfate of amine from the aromatic amine compound and a stoichiometric amount of sulfuric acid and heated to obtain an aminesulfonic acid.

The sulfation reactions may involve methods by which esters or salts of sulfuric acid (sulfates) are formed. The esters may be prepared by treating an alcohol with sulfuric acid, sulfur trioxide, chlorosulfuric acid, or sulfamic acid. The sulfating agents may include concentrated sulfuric acid, oleum, sulfur trioxide, chlorosulfonic acid, or sulfamic acid.

The polymerization reaction may be any polymerization reaction suitable for forming any of the polymers discussed above. The catalyst used in these reactions may be any suitable polymerization catalyst for making the indicated polymer. Examples of catalysts that may be used may include Lewis acids such as $BF_3$, organolithium catalysts such as butyl lithium, Grignard reagents, Ziegler-Natta catalysts, and the like.

The catalyst for the reactions conducted in accordance with the inventive process may be a homogeneous catalyst or a heterogeneous catalyst. The homogeneous catalyst may be immobilized on a support. The catalyst may have any size and geometric configuration that fits within the process microchannels. The catalyst may be a graded catalyst.

The catalyst may be in the form of particulate solids (e.g., pellets, powder, fibers, and the like) having a median particle diameter of about 1 to about 1000 microns, and in one embodiment about 10 to about 500 microns, and in one embodiment about 25 to about 250 microns.

The catalyst may be in the form of a mesoporous material wherein the average pore size may be at or above about 1 nanometer (nm), for example, in the range from about 1 to about 100 nm, and in one embodiment from about 1 to about 20 nm.

The catalyst may be in the form of a fixed bed of particulate solids such as illustrated in FIG. 35. Referring to FIG. 35, the catalyst 350 is contained within process microchannel 352. The reactants flow through the catalyst bed as indicated by arrows 354 and 356.

The catalyst may be supported on a porous support structure such as a foam, felt, wad or a combination thereof. The term "foam" is used herein to refer to a structure with continuous walls defining pores throughout the structure. The term "felt" is used herein to refer to a structure of fibers with interstitial spaces therebetween. The term "wad" is used herein to refer to a support having a structure of tangled strands, like steel wool. The catalyst may be supported on a support having a honeycomb structure or a serpentine configuration.

The catalyst may be supported on a flow-by support structure such as a felt with an adjacent gap, a foam with an adjacent gap, a fin structure with gaps, a washcoat on any inserted substrate, or a gauze that is parallel to the flow direction with a corresponding gap for flow. An example of a flow-by structure is illustrated in FIG. 36. In FIG. 36 the catalyst 360 is contained within process microchannel 362. An open passage way 364 permits the flow of the reactants through the process microchannel 362 in contact with the catalyst 360 as indicated by arrows 366 and 368.

The catalyst may be supported on a flow-through support structure such as a foam, wad, pellet, powder, or gauze. An example of a flow-through structure is illustrated in FIG. 37. In FIG. 37, the flow-through catalyst 370 is contained within process microchannel 372 and the reactants flow through the catalyst 370 as indicated by arrows 374 and 376.

The support may be formed from a material comprising silica gel, foamed copper, sintered stainless steel fiber, steel wool, alumina, poly(methyl methacrylate), polysulfonate, poly(tetrafluoroethylene), iron, nickel sponge, nylon, polyvinylidene difluoride, polypropylene, polyethylene, polyethylene ethylketone, polyvinyl alcohol, polyvinyl acetate, polyacrylate, polymethylmethacrylate, polystyrene, polyphenylene sulfide, polysulfone, polybutylene, or a combination of two or more thereof. In one embodiment, the support structure may be made of a heat conducting material, such as a metal, to enhance the transfer of heat away from the catalyst.

The catalyst may be directly washcoated on the interior walls of the process microchannels, grown on the walls from solution, or coated in situ on a fin structure. The catalyst may be coated on structured walls such as illustrated in FIGS. 48-49. The catalyst may be coated on surface features such as those illustrated in FIGS. 46-47. The catalyst may be in the form of a single piece of porous contiguous material, or many pieces in physical contact. In one embodiment, the catalyst may comprise a contiguous material and have a contiguous porosity such that molecules can diffuse through the catalyst. In this embodiment, the fluids may flow through the catalyst rather than around it. In one embodiment, the cross-sectional area of the catalyst may occupy from about 1 to about 99%, and in one embodiment from about 10 to about 95% of the cross-sectional area of the process microchannels. The catalyst may have a surface area, as measured by BET, of greater than about 0.5 $m^2/g$, and in one embodiment greater than about 2 $m^2/g$, and in one embodiment greater than about 5 $m^2/g$, and in one embodiment greater than about 10 $m^2/g$, and in one embodiment greater than about 25 $m^2/g$, and in one embodiment greater than about 50 $m^2/g$.

The catalyst may comprise a porous support, an interfacial layer overlying the porous support, and a catalyst material dispersed or deposited on the interfacial layer. The interfacial layer may be solution deposited on the support or it may be deposited by chemical vapor deposition or physical vapor deposition. In one embodiment the catalyst comprises a porous support, optionally a buffer layer overlying the support, an interfacial layer overlying the support or the optional buffer layer, and a catalyst material dispersed or deposited on the interfacial layer. Any of the foregoing layers may be continuous or discontinuous as in the form of spots or dots, or in the form of a layer with gaps or holes.

The porous support may have a porosity of at least about 5% as measured by mercury porosimetry and an average pore size (sum of pore diameters divided by number of pores) of about 1 to about 1000 microns. The porous support may be made of any of the above indicated materials identified as being useful in making a support structure. The porous support may comprise a porous ceramic support or a metal foam. Other porous supports that may be used include carbides, nitrides, and composite materials. The porous support may have a porosity of about 30% to about 99%, and in one embodiment about 60% to about 98%. The porous support may be in the form of a foam, felt, wad, or a combination thereof. The open cells of the metal foam may range from about 20 pores per inch (ppi) to about 3000 ppi, and in one embodiment about 20 to about 1000 ppi, and in one embodiment about 40 to about 120 ppi. The term "ppi" refers to the largest number of pores per inch (in isotropic materials the direction of the measurement is irrelevant; however, in anisotropic materials, the measurement is done in the direction that maximizes pore number).

The buffer layer, when present, may have a different composition and/or density than both the porous support and the interfacial layers, and in one embodiment has a coefficient of thermal expansion that is intermediate the thermal expansion coefficients of the porous support and the interfacial layer. The buffer layer may be a metal oxide or metal carbide. The buffer layer may be comprised of $Al_2O_3$, $TiO_2$, $SiO_2$, $ZrO_2$, or combination thereof. The $Al_2O_3$ may be $\alpha$-$Al_2O_3$, $\gamma$-$Al_2O_3$ or a combination thereof. $\alpha$-$Al_2O_3$ provides the advantage of excellent resistance to oxygen diffusion. The buffer layer may be formed of two or more compositionally different sublayers. For example, when the porous support is metal, for example a stainless steel foam, a buffer layer formed of two compositionally different sub-layers may be used. The first sublayer (in contact with the porous support) may be $TiO_2$. The second sublayer may be $\alpha$-$Al_2O_3$ which is placed upon the $TiO_2$. In one embodiment, the $\alpha$-$Al_2O_3$ sublayer is a dense layer that provides protection of the underlying metal surface. A less dense, high surface area interfacial layer such as alumina may then be deposited as support for a catalytically active layer.

The porous support may have a thermal coefficient of expansion different from that of the interfacial layer. In such a case a buffer layer may be needed to transition between the two coefficients of thermal expansion. The thermal expansion coefficient of the buffer layer can be tailored by controlling its composition to obtain an expansion coefficient that is compatible with the expansion coefficients of the porous support and interfacial layers. The buffer layer should be free of openings and pin holes to provide superior protection of the underlying support. The buffer layer may be nonporous. The buffer layer may have a thickness that is less than one half of the average pore size of the porous support. The buffer layer may have a thickness of about 0.05 to about 10 μm, and in one embodiment about 0.05 to about 5 μm.

In one embodiment of the invention, adequate adhesion and chemical stability may be obtained without a buffer layer. In this embodiment the buffer layer may be omitted.

The interfacial layer may comprise nitrides, carbides, sulfides, halides, metal oxides, carbon, or a combination thereof. The interfacial layer provides high surface area and/or provides a desirable catalyst-support interaction for supported catalysts. The interfacial layer may be comprised of any material that is conventionally used as a catalyst support. The interfacial layer may be comprised of a metal oxide. Examples of metal oxides that may be used include $\gamma$-$Al_2O_3$, $SiO_2$, $ZrO_2$, $TiO_2$, tungsten oxide, magnesium oxide, vanadium oxide, chromium oxide, manganese oxide, iron oxide, nickel oxide, cobalt oxide, copper oxide, zinc oxide, molybdenum oxide, tin oxide, calcium oxide, aluminum oxide, lanthanum series oxide(s), zeolite(s) and combinations thereof. The interfacial layer may serve as a catalytically active layer without any further catalytically active material deposited thereon. Usually, however, the interfacial layer is used in combination with a catalytically active layer. The interfacial layer may also be formed of two or more compositionally different sublayers. The interfacial layer may have a thickness that is less than one half of the average pore size of the porous support. The interfacial layer thickness may range from about 0.5 to about 100 μm, and in one embodiment from about 1 to about 50 μm. The interfacial layer may be either crystalline or amorphous. The interfacial layer may have a BET surface area of at least about 1 $m^2$/g.

The catalyst may be deposited on the interfacial layer. Alternatively, the catalyst material may be simultaneously deposited with the interfacial layer. The catalyst layer may be intimately dispersed on the interfacial layer. That the catalyst layer is "dispersed on" or "deposited on" the interfacial layer includes the conventional understanding that microscopic catalyst particles are dispersed: on the support layer (i.e., interfacial layer) surface, in crevices in the support layer, and in open pores in the support layer.

The catalyst may be supported on an assembly of one or more fins positioned within the process microchannels. Examples are illustrated in FIGS. 38-40. Referring to FIG. 38, fin assembly 380 includes fins 382 which are mounted on fin support 384 which overlies base wall 386 of process microchannel 388. The fins 382 project from the fin support 384 into the interior of the process microchannel 388. The fins 382 extend to the interior surface of upper wall 390 of process microchannel 388. Fin channels 392 between the fins 392 provide passage ways for fluid to flow through the process microchannel 388 parallel to its length. Each of the fins 382 has an exterior surface on each of its sides, this exterior surface provides a support base for the catalyst. With the inventive process, the reactants flow through the fin channels 392, contact the catalyst supported on the exterior surface of the fins 382, and react to form the product. The fin assembly 380a illustrated in FIG. 39 is similar to the fin assembly 380 illustrated in FIG. 38 except that the fins 382a do not extend all the way to the interior surface of the upper wall 390 of the microchannel 388. The fin assembly 380b illustrated in FIG. 40 is similar to the fin assembly 380 illustrated in FIG. 38 except that the fins 382b in the fin assembly 380b have cross sectional shapes in the form of trapezoids. Each of the fins (382, 382a, 382b) may have a height ranging from about 0.02 mm up to the height of the process microchannel 838, and in one embodiment from about 0.02 to about 10 mm, and in one embodiment from about 0.02 to about 5 mm, and in one embodiment from about 0.02 to about 2 mm. The width of each fin (382, 382a, 382b) may range from about 0.02 to about 5 mm, and in one embodiment from about 0.02 to about 2 mm and in one embodiment about 0.02 to about 1 mm. The length of each fin (382, 382a, 382b) may be of any length up to the length of the process microchannel 838, and in one embodiment up to about 10 m, and in one embodiment about 1 cm to about 10 m, and in one embodiment about 1 cm to about 5 m, and in one embodiment about 1 cm to about 2.5 m. The gap between each of the fins (382, 382a, 382b) may be of any value and may range from about 0.02 to about 5 mm, and in one embodiment from about 0.02 to about 2 mm, and in one embodiment from about 0.02 to about 1 mm. The number of fins (382, 382a, 382b) in the process microchannel 388 may range from about 1 to about 50 fins per centimeter of width of the process microchannel 388, and in one embodiment from about 1 to about 30 fins per centimeter, and in one embodiment from about 1 to about 10 fins per centimeter, and in one embodiment from about 1 to about 5 fins per centimeter, and in one embodiment from about 1 to about 3 fins per centimeter. When viewed along its length, each fin (382, 382a, 382b) may be straight, tapered or have a serpentine configuration. The fin assembly (380, 380a, 380b) may be made of any material that provides sufficient strength, dimensional stability and heat transfer characteristics to permit operation for which the process microchannel is intended. These materials include: steel (e.g., stainless steel, carbon steel, and the like);

monel; inconel; aluminum; titanium; nickel; platinum; rhodium; copper; chromium; brass; alloys of any of the foregoing metals; polymers (e.g., thermoset resins); ceramics; glass; composites comprising one or more polymers (e.g., thermoset resins) and fiberglass; quartz; silicon; or a combination of two or more thereof. The fin assembly (380, 380a, 380b) may be made of an $Al_2O_3$ forming material such as an alloy comprising Fe, Cr, Al and Y, or a $Cr_2O_3$ forming material such as an alloy of Ni, Cr and Fe.

The catalyst may be supported by the microgrooved support strip illustrated in FIG. 41. Referring to FIG. 41, microgrooved support strip 400 comprises support strip 410 which is rectangular in shape and has a length (l), width (w) and thickness (t). The support strip 410 has a first or top surface 412, a second or bottom surface 414, a first side edge 416, a second side edge 418, a front edge 420 and a back edge 422. The support strip 410 has a center axis 424 extending along the length (l) of the support strip. A plurality of parallel microgrooves 430 are formed in the first surface 412. The microgrooves 430 may extend between the first side edge 416 of the support strip 410 and the second side edge 418, but may not project through the side edges. The microgrooved support strip 400 includes non-grooved sections 434 and 436 which provide the microgrooved support strip 400 with a front edge 420 and a back edge 422 that are closed. That is, the front edge 420 and the back edge 422 of the microgrooved support strip 400 are sufficiently blocked to prevent fluid from flowing through the front edge 420 and back edge 422. The microgrooves 430 may be oriented at an angle 425 relative to the center axis 424 that is sufficient to permit fluid to flow in the microgrooves 430 in a general direction from the front edge 420 toward the back edge 422. The front edge 420, back edge 422 and side edges 416 and 418 of the microgrooved support strip 400 are closed. These closed edges do not permit the flow of fluid through the front edge, back edge and side edges.

The microgrooves 430 illustrated in FIG. 41 have cross-sections in the form of squares. Alternatively, each of the microgrooves 430 may have a rectangular cross-section, a vee shaped cross-section, a semi-circular cross-section, a dovetail shaped cross-section, or a trapezoid shaped cross-section. Those skilled in the art will recognize that microgrooves with other cross-sectional shapes may be used. Each of the microgrooves 430 has a depth, width and length. The depth of each of the microgrooves 430 may be in the range from about 0.1 to about 1000 microns, and in one embodiment from about 1 to about 100 microns. The width, which would be the width at its widest dimension, for each of the microgrooves 430 may be in the range of about 0.1 to about 1000 microns, and in one embodiment from about 1 to about 500 microns. The length of each of the microgrooves 430 may be of any dimension which depends upon the width (w) of the support strip 410. The length of each microgroove 430 may be in the range of about 0.1 to about 100 cm, and in one embodiment from about 0.1 to about 10 cm. The spacing between the microgrooves 430 may be in the range up to about 1000 microns, and in one embodiment from about 0.1 to about 1000 microns, and in one embodiment from about 1 to about 1000 microns. Each of the microgrooves 430 may be oriented toward the back edge 422 and the first side edge 416 and forms an angle 425 with the center axis 424 that may be sufficient to permit fluid to flow in the microgrooves in a general direction toward the second side edge 418 and back edge 422. The angle 425 may be from about 0° to about 90°. The angle 425 may be in the range from about 50° to about 80°, and in one embodiment from about 60° to about 75°. The microgrooves 430 may be aligned at an angle of about 90° or at a right angle with the center axis 424, and in one embodiment extend from the first side edge 416 to the second side edge 418. The microgrooves 430 may be aligned parallel to the center axis 424, and in one embodiment extend from the front edge 420 to the back edge 422. The microgrooves 430 may be formed in the first surface 412 of the support strip 410 by any suitable technique, including photochemical machining, laser etching, water jet machining, and the like.

The support strip 410 may have a thickness (t) in the range from about 0.1 to about 5000 microns, and in one embodiment from about 1 to about 1000 microns. The support strip 410 may have any width (w) and any length (l), the width and length depending upon the dimensions of the microchannel for which the support strip 410 is to be used. The support strip 410 may have a width (w) in the range from about 0.01 to about 100 cm, and in one embodiment from about 0.1 to about 10 cm. The length (l) of the support strip 410 may be in the range of about 0.01 to about 100 cm, and in one embodiment from about 0.1 to about 10 cm. The support strip 410 as illustrated in FIG. 30 is in the form of a rectangle. However, it is to be understood that the support strip 410 may have any configuration, for example, square, circle, oval, etc., to conform to the design of the microchannel for which it is to be used.

The support strip 410 may be made of any material that provides sufficient strength, dimensional stability and heat transfer characteristics to permit the use of the microgrooved support strip 400 in a microchannel for supporting a catalyst. The support strip 410 may be made of metal, silicon carbide, graphite or a combination of two or more thereof. The metal may comprise steel, aluminum, titanium, nickel, platinum, rhodium, copper, chromium, brass, or an alloy of any of the foregoing metals. The support structure 410 may be made of stainless steel or an alloy comprising iron, chromium, aluminum and yttrium.

The microgrooved support strip 400 may be used as a flow-by support structure in a microchannel.

Figures 44, 45:
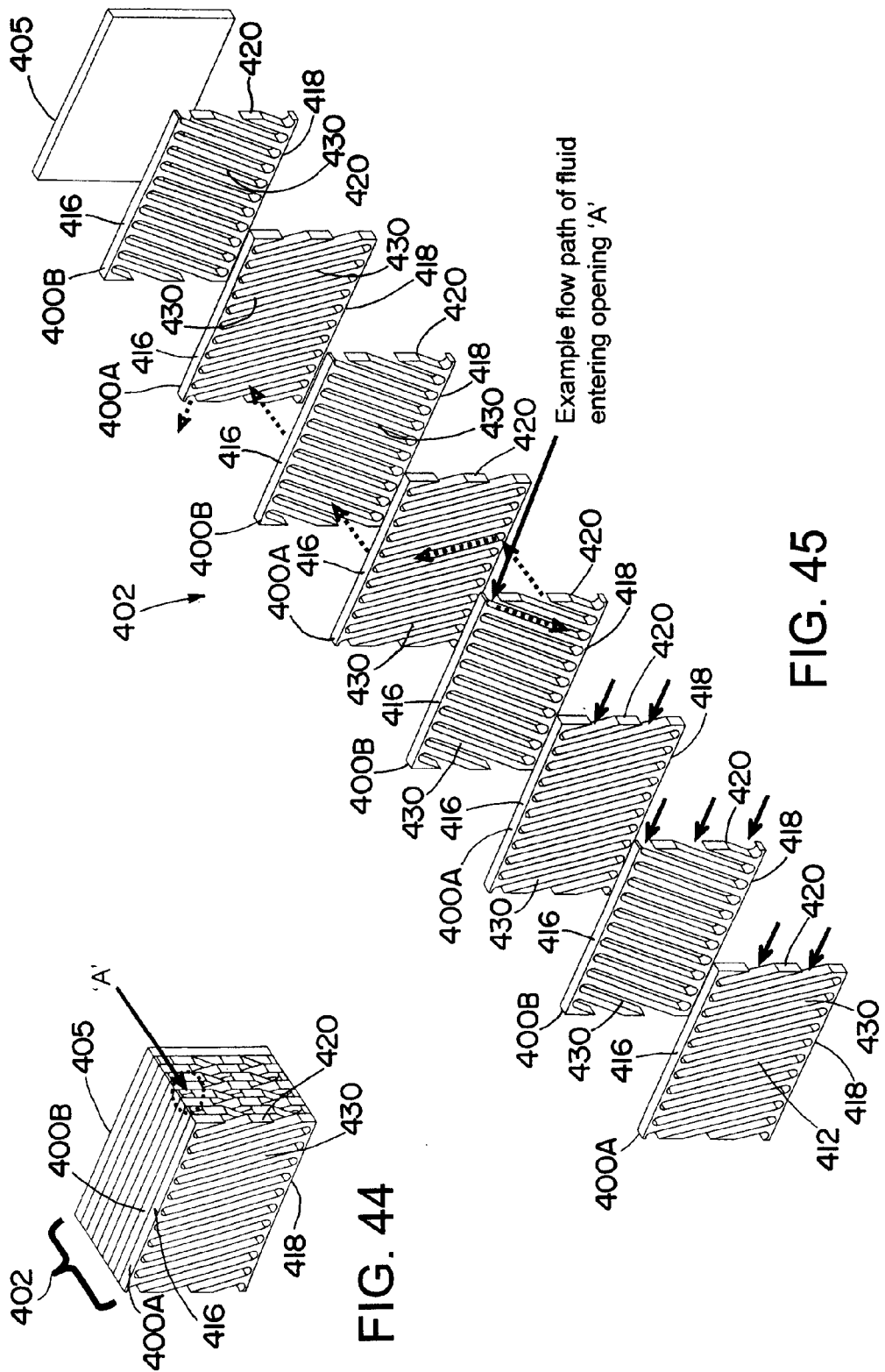
FIG. 44 is a schematic illustration showing a plurality of microgrooved support strips positioned side by side forming a composite support structure, the front and back edges of each of the microgrooved support strips being open sufficiently to permit fluid to flow through such edges. The microgrooves in each of the support strips project through the support strips sufficiently to permit fluid to flow through the support strips from one support strip to another. The composite support structure may be used in the reaction zones of the process microchannels described herein.
FIG. 45 is a schematic illustration of an exploded view of the composite support structure illustrated in FIG. 44. The support structure illustrated in FIG. 45 comprises four (4) first microgrooved support strips and four (4) second microgrooved support strips positioned side by side in alternating sequence. The microgrooves in each of the support strips project through the support strips sufficiently to permit fluid to flow through the support strips from one support strip to another. The first microgrooved support strips employ microgrooves that form angles with the center axis of the support strips that are oriented toward the front edges and first side edges of the support strips and are more than about 0° and less than 90°, for example, in the range from about 60° to about 80°. The second microgrooved support strips employ microgrooves that form angles with the center axis of the support strips that are oriented toward the front edges and first side edges of the support strips and are more than 90° and less than about 180°, for example, in the range from about 100° to about 120°.

In one embodiment, a plurality of the microgrooved support strips may be stacked one above another or positioned side by side to form a composite support structure which may be used to support a catalyst for use in the inventive process. The composite support structure, in one embodiment, is illustrated in FIGS. 44 and 45. The support strips 400A and 400B illustrated in FIGS. 44 and 45 have open front 420 and back edges 422, closed side edges 416 and 418, and microgrooves 430 that penetrate all the way through the support strip 410 from the top surface 412 to the bottom surface 414. The open front edges 420, back edges 422 and microgrooves 430 permit fluid to flow through the microgrooved support strips from one support strip to another support strip within the composite support structure as the fluid flows through the composite support structure. The number of microgrooved support strips employed in such a composite support structure may be of any number, for example up to about 50, and in one embodiment up to about 30, and in one embodiment up to about 15, and in one embodiment up to about 10. The composite support structure also includes end plates to prevent fluid from flowing out of the sides of the composite construction.

The composite support structure 402 illustrated in FIGS. 44 and 45 comprises eight (8) microgrooved support strips, four each of microgrooved support strips 400A and 400B positioned side by side in alternating sequence and two end plates 405 (only one end plate is shown in FIGS. 44 and 45). The microgrooved support strips 400A and 400B each comprise support strip 410 which is rectangular in shape and has a length, width and thickness. The support strip 410 has a center axis extending along the length of the support strip. A plurality of parallel microgrooves 430 are formed in the support strip 410 and project through the support strip from the top surface 412 to the bottom surface 414. The open front 420 and back edges 422 and the open microgrooves 430 permit fluid to flow from one microgrooved support strip to another within the composite support structure 402. A first group of parallel microgrooves extends from the first side edge 416 of the support strip 410 to the second side edge 418. A second group of the microgrooves 430 extends from the front edge 420 to the second side edge 418. A third group of the microgrooves 430 extends from the first side edge 416 of the support strip 410 to the back edge 422. The microgrooves 430 extend to the side edges 416 and 418 but do not project through these side edges. The end plates 405 prevent fluid from flowing out of the sides of the composite support structure 402. The second end plate 405 that is not shown in the drawings would be positioned adjacent to the first microgrooved support strip 400A on the left side in FIGS. 44 and 45. The microgrooves 430 in the support strips 400A may be oriented at an angle relative to the center axis of the support strip and the side edge 416 that is from about 90° to about 180°, and in one embodiment in the range from about 100° to about 150°. The microgrooves 430 in the support strip 400B may be oriented at an angle relative to the center axis of the support strip and the side edge 116 that is from about 0° to about 90°, and in one embodiment in the range from about 50° to about 80°. Fluid may flow through the composite structure 402 by entering the front edge 420 of the support strips 400A and 400B, flowing in and through the microgrooves 430 and transferring from the microgrooves 430 in one support strip (400A or 400B) to the microgrooves 430 in another support strip (400A or 400B) until the fluid reaches the back edge 422 of the support strips and then flows out of composite support structure 402. FIG. 45 shows an example of a flow path through the composite support structure 402 for a fluid entering opening 'A' of the composite support structure illustrated in FIG. 44. The flow of fluid through the composite support structure 402 may be described as permeating, diffusing and advecting from one layer to another until the fluid passes from the front end of the composite support structure to the back end.

The catalyst may be deposited on the microgrooved support strips (400, 400A, 400B) using conventional techniques. These may include washcoating the catalyst on the microgrooved support strips, growing the catalyst on the microgrooved support strips, or depositing the catalyst on the microgrooved support strips using vapor deposition. The vapor deposition may be chemical vapor deposition or physical vapor deposition. The catalyst may be deposited by slurry-coating, sol-coating or solution-coating. In one embodiment, the catalyst may be in the form of microsized particulates deposited in and adhered to the microgrooves 430 of the support strip or composite support structure. The catalyst loading may be in the range from about 0.1 to about 100 milligrams (mg) per square centimeter of microgrooved support strip, and in one embodiment in the range from about 1 to about 10 mg of catalyst per square centimeter of microgrooved support strip. The microsized particulates may have average particle sizes in the range from about 0.01 to about 100 microns, and in one embodiment in the range from about 0.1 to about 50 microns, and in one embodiment in the range from about 0.1 to about 10 microns, and in one embodiment from about 0.1 to about 7 microns, and in one embodiment from about 0.1 to about 5 microns, and in one embodiment from about 0.1 to about 3 microns, and in one embodiment from about 0.1 to about 2 microns, and in one embodiment from about 0.1 to about 1 micron, and in one embodiment from about 0.1 to about 0.5 micron.

An advantage of the microgrooved support strips and composite structures relates to the fact that microsized particles of catalyst may be positioned in and anchored to the microgrooves thus reducing the tendency of the particulates being swept away by the flow of process fluids through the microchannels.

Figure 42:
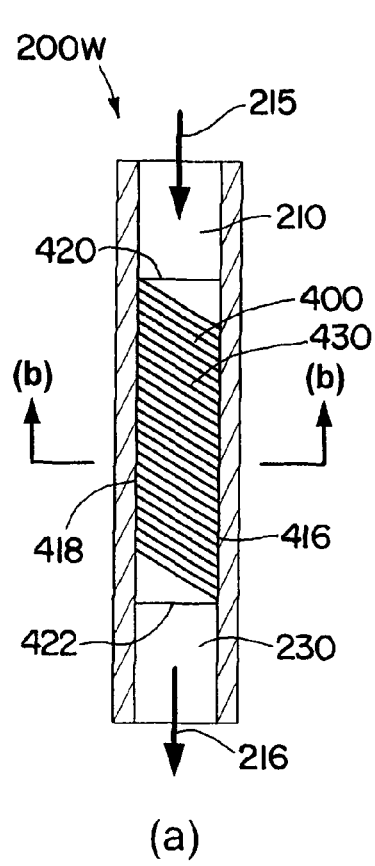
FIG. 42(a) is a schematic illustration of a process microchannel that may be used in the microchannel processing unit illustrated in FIG. 3. The process microchannel contains a microgrooved support strip as illustrated in FIG. 41, the microgrooved support strip being adapted for supporting a catalyst.
FIG. 42(b) is a cross-sectional view of the process microchannel illustrated in FIG. 42(a) taken along line (b)-(b) in FIG. 42(a).
Figure 42:
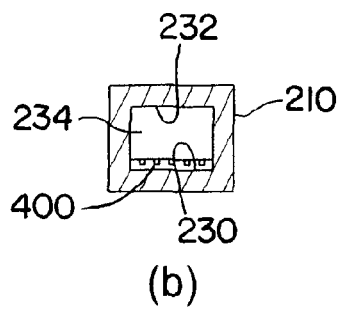
Figure 43:
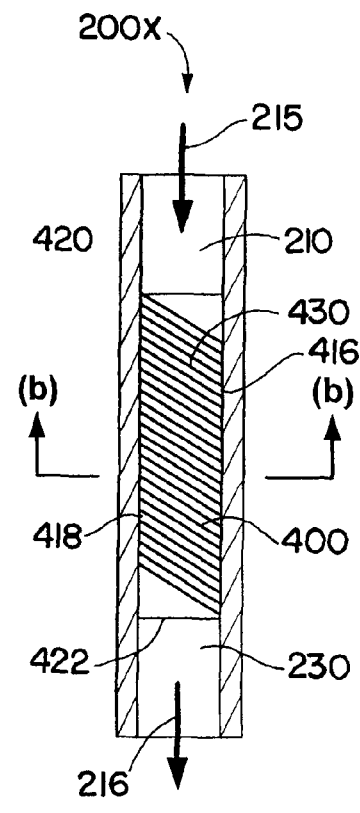
FIG. 43 is a schematic illustration of a process microchannel that may be used in the microchannel processing unit illustrated in FIG. 3. The process microchannel is similar to the process microchannel illustrated in FIG. 42(a) with the exception that the process microchannel illustrated in FIG. 43(a) contains opposite interior walls and a catalyst supporting microgrooved support strip positioned on each of the opposite interior walls.
Figure 43:
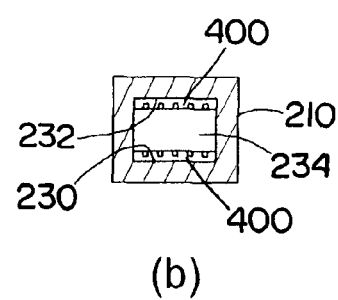

Repeating units 200W and 200X for use in microchannel processing unit core 102 employing microgrooved support strip 400 for supporting a catalyst are illustrated in FIGS. 42 and 43. The number of these repeating units that may be used in the microchannel processing unit core 102 may be any number, for example, one, two, three, four, five, six, eight, ten, hundreds, thousands, etc. Referring to FIG. 42, repeating unit 200W includes process microchannel 210 with microgrooved support strip 400 mounted on interior wall 230 of the process microchannel 210. Bulk flow region 234 is the space within the process microchannel 210 above the microgrooved support strip 400. Process fluid flows through the process microchannel 210 as indicated by arrows 215 and 216. In flowing through the process microchannel 210, the process fluid flows through the bulk flow region 234 in contact with the catalyst supporting microgrooved support strip 400. The catalyst may be in the form of microsized particulates positioned in the microgrooves 430. The microgrooved support strip 400 is a flow-by support strip. However, some of the process fluid may flow in the microgrooves 430 in contact with the catalyst. The flow of the process fluid through the microgrooves 430 may be in the general direction from the side edge 418 toward the side edge 416 and the back edge 422. Heat exchange channels (not shown in the drawing) may be provided for heating and/or cooling the process microchannel 210.

The repeating unit 200X illustrated in FIG. 43 is similar to the repeating unit 200W illustrated in FIG. 42 with the exception that the process microchannel 210 illustrated in FIG. 43 contains opposite interior walls 230 and 232 and a catalyst supporting microgrooved support strip 400 mounted on each of the opposite interior walls.

An advantage of the inventive process, at least in one embodiment, is that the gap distances between the process microchannels, staged addition channels, and heat exchange channels may be the same whether the process is intended for laboratory or pilot plant scale or for full production scale. As a result, the particle size distribution of the second fluid in the multiphase fluid mixtures produced by the microchannel processing units used with the inventive process may be substantially the same whether the microchannel processing unit is built on a laboratory or pilot plant scale or as a full scale plant unit.

Shear force or stress on a liquid control element (in discretized form) in the direction of velocity u may be calculated by the formula $F_x = mu \cdot du/dy$, where mu is viscosity, and du/dy is the velocity gradient for the liquid flow normal to the apertured section. However, as in a location of fluid (represented by a control element) the velocity generally has three components, and shear force also has three components. For a channel flow near and at the surface, a one dimensional assumption can be made and $F_x$ can approximate the net shear stress at an element surface of the liquid. The use of computational fluid dynamics, including commercial software packages such as Fluent or FEMLAB, may be used to solve the required transport equations such that the surface shear force may be calculated. The surface shear force or stress may be calculated along the channel length, parallel to the direction of flow. Shear force or stress may also be calculated between parallel channels, where flow distribution effects are included to determine the mass flux into each parallel channel as a function of the detailed channel and manifold geometry. Additional calculation methods can be found, for example, in "Fundamentals of Fluid Mechanics," 3$^{rd}$ Ed., B. R. Munson, D. F. Young and T. H. Okiishi, John Wiley & Son, Inc., Weinheim, 1998.

In one embodiment, the shear force deviation factor (SFDF) for a process employing a single process microchannel may be within about 50% of the SFDF for a scaled-up process involving multiple process microchannels. SFDF may be calculated using the formula $$SFDF=(F_{max}-F_{min})/(2F_{mean})$$

wherein: $F_{max}$ is the maximum shear stress force in a process microchannel for a specific liquid; $F_{min}$ is the minimum shear stress force in the process microchannel for the liquid; and $F_{mean}$ is the arithmetic average shear force for the fluid at the surface of the apertured section (250, 250A) within the process microchannel 210. Within a single process microchannel, operated in accordance with the inventive process, the SFDF may be less than about 2, and in one embodiment less than about 1, and in one embodiment less than about 0.5, and in one embodiment less than about 0.2.

In one embodiment, the inventive process may provide for a relatively uniform shear stress force while employing multiple process microchannels. To measure the shear force uniformity among multiple process microchannels, the average shear force is calculated for each channel and compared. $F_{max}$ is the largest value of the average channel shear force, and $F_{min}$ is the smallest value of the average shear force. $F_{mean}$ is the mean of the average shear forces of all the channels. SFDF may be calculated from these values. Among multiple process microchannels, at least with one embodiment of the inventive process, the SFDF may be less than about 2, and in one embodiment less than about 1, and in one embodiment less than about 0.5, and in one embodiment less than about 0.2.

The deviation in the shear force within a process microchannel may also be defined as:

$$SFDF' = \frac{F_{max} - F_{min}}{F_{max}}$$

wherein $F_{max}$, $F_{min}$ are as defined above. In one embodiment, the SFDF' may be less than about 0.9, and in one embodiment less than about 0.5, and in one embodiment less than about 0.1.

For a multiple process channel, the deviation in shear force may be defined as:

$$SFDF'' = \frac{F'_{max} - F'_{min}}{F'_{max}}$$

wherein $F'_{max}$ is defined as the maximum shear force at a given axial location for multiple process microchannels, and $F'_{min}$ is defined as the minimum shear force at the same axial location for the multiple process microchannels. In one embodiment, the SFDF'' may be less than about 0.9, and in one embodiment less than about 0.5, and in one embodiment less than about 0.1.

In a scale up device, for certain applications, it may be required that the mass of the process fluid be distributed uniformly among the microchannels. Such an application may be when the process fluid is required to be heated or cooled down with adjacent heat exchange channels. The uniform mass flow distribution may be obtained by changing the cross-sectional area from one parallel microchannel to another microchannel. The uniformity of mass flow distribution may be defined by Quality Index Factor (Q-factor) as indicated below. A Q-factor of 0% means absolute uniform distribution.

$$Q = \frac{\dot{m}_{max} - \dot{m}_{min}}{\dot{m}_{max}} \times 100$$

A change in the cross-sectional area may result in a difference in shear stress on the wall.

In one embodiment, the Q-factor for the process microchannels may be less than about 50%, and in one embodiment less than about 20%, and in one embodiment less than about 5%, and in one embodiment less than about 1%.

In one embodiment, the Q-factor for the process microchannel may be less than about 50% and the SFDF'' may be less than about 0.8. In one embodiment, the Q-factor may be less than about 5%, and the SFDF'' less than about 0.5. In one embodiment, the Q-factor may be less than about 1%, and the SFDF'' may be less than about 0.1.

A heat source and/or heat sink may be used for cooling, heating or both cooling and heating. The heat source and/or heat sink may comprise one or more heat exchange channels. The heat source may comprise one or more non-fluid heating elements such as one or more electric heating elements or resistance heaters. The heat sink may comprise one or more non-fluid cooling elements. These may be adjacent to the process microchannels and/or staged addition channels. In one embodiment, the heat source and/or heat sink may not be in contact with or adjacent to the process microchannel and/or staged addition channels, but rather can be remote from either or both the process microchannel and/or staged addition channels, but sufficiently close to the process microchannel and/or staged addition channels to transfer heat between the heat source and/or heat sink and the process microchannels and/or staged addition channels. The non-fluid heating and/or non-fluid cooling elements may be used to form one or more walls of the process microchannels (210) and/or staged addition channels (240, 240A). The non-fluid heating and/or cooling elements may be built into one or more walls of the process microchannels and/or staged addition channels. The non-fluid heating and/or cooling elements may be thin sheets, rods, wires, discs or structures of other shapes embedded in the walls of the process microchannels and/or staged addition channels. The non-fluid heating and/or cooling elements may be in the form of foil or wire adhered to the process microchannel walls and/or staged addition channel walls. Heating and/or cooling may be effected using Peltier-type thermoelectric cooling and/or heating elements. Multiple heating and/or cooling zones may be employed along the length of the process microchannels and/or staged addition channels. Similarly, heat transfer fluids at different temperatures in one or more heat exchange channels may be employed along the length of the process microchannels and/or staged addition channels. The heat source and/or heat sink may be used to provide precise temperature control within the process microchannels and/or staged addition channels.

The heat exchange fluid may be any fluid. These include air, steam, liquid water, gaseous nitrogen, liquid nitrogen, other gases including inert gases, carbon monoxide, carbon dioxide, oils such as mineral oil, gaseous hydrocarbons, liquid hydrocarbons, and heat exchange fluids such as Dowtherm A and Therminol which are available from Dow-Union Carbide.

The heat exchange fluid may comprise the first fluid, second fluid and/or product. This can provide process pre-heat and/or an increase in overall thermal efficiency of the process.

In one embodiment, the heat exchange channels comprise process channels wherein an endothermic or exothermic process is conducted. These heat exchange process channels may be microchannels. Examples of endothermic processes that may be conducted in the heat exchange channels include steam reforming and dehydrogenation reactions. Examples of exothermic processes that may be conducted in the heat exchange channels include water-gas shift reactions, methanol synthesis reactions and ammonia synthesis reactions.

In one embodiment, the heat exchange fluid undergoes a phase change in the heat exchange channels. This phase change provides additional heat addition to or removal from the process microchannels and/or second reactant stream channels beyond that provided by convective heating or cooling. An example of such a phase change would be an oil or water that undergoes boiling. In one embodiment, the vapor mass fraction quantity of the boiling of the phase change fluid may be up to about 100%, and in one embodiment up to about 75%, and in one embodiment up to about 50%.

The heat flux for heat exchange in the microchannel processing unit may be in the range from about 0.01 to about 500 watts per square centimeter of surface area of the heat transfer walls in the microchannel processing unit ($W/cm^2$), and in one embodiment from about 0.1 to about 250 $W/cm^2$, and in one embodiment from about 0.1 to about 100 $W/cm^2$, and in one embodiment from about 1 to about 100 $W/cm^2$, and in one embodiment from about 1 to about 50 $W/cm^2$, and in one embodiment from about 1 to about 25 $W/cm^2$, and in one embodiment from about 1 to about 10 $W/cm^2$.

In one embodiment, the temperature of the fluid streams entering the microchannel processing unit 100 may be within about 200° C., and in one embodiment within about 100° C., and in one embodiment within about 50° C., and in one embodiment within about 20° C., of the temperature of the product exiting the microchannel processing unit 100.

The use of controlled heat exchange between heat exchange channels in close proximity or adjacent to the process microchannels and/or staged addition channels may allow for uniform temperature profiles for the process microchannels and/or staged addition channels. This provides for the possibility of a more uniform heat exchange at more rapid rates than can be obtained with conventional processing equipment such as mixing tanks. For a microchannel processing unit employing multiple process microchannels and optionally multiple staged addition second channels, the temperature difference between the process microchannels and/or staged addition channels at least one common position along the lengths of the process microchannels may be less than about 5° C., and in one embodiment less than about 2° C., and in one embodiment less than about 1° C.

The heat exchange zones 270 adjacent to either the process microchannels and/or staged addition channels may employ separate temperature zones along the length of such channels. For example, in one embodiment, the temperature in a first zone near the entrance to the process microchannel may be maintained at a temperature above or below a second temperature in a second zone near the end of the process microchannel. A cool down or quench zone may be incorporated into the process microchannels to cool the product. Numerous combinations of thermal profiles are possible, allowing for a tailored thermal profile along the length of the process microchannels and/or staged addition channels, including the possibility of heating or cooling zones before and/or after the reaction zone in the process microchannels to heat or cool the reactants and/or product.

The heat exchange fluid entering the heat exchange channels may be at a temperature in the range from about −40° C. to about 400° C., and in one embodiment about 0° C. to about 400° C., and in one embodiment from about 20° C. to about 300° C., and in one embodiment from about 20° C. to about 250° C., and in one embodiment from about 20° C. to about 200° C. The heat exchange fluid exiting the heat exchange channels may be at a temperature in the range from about −40° C. to about 400° C., and in one embodiment about 0° C. to about 400° C., and in one embodiment from about 20° C. to about 300° C., and in one embodiment from about 20° C. to about 250° C., and in one embodiment from about 20° C. to about 200° C. The residence time of the heat exchange fluid in the heat exchange channels may be in the range from about 5 ms to about 1 minute, and in one embodiment from about 20 ms to about 1 minute, and in one embodiment from about 50 ms to about 1 minute, and in one embodiment about 100 ms to about 1 minute. The pressure drop for the heat exchange fluid as it flows through the heat exchange channels may be in the range up to about 1 atm/m, and in one embodiment up to about 0.5 atm/m, and in one embodiment up to about 0.1 atm/m, and in one embodiment from about 0.01 to about 1 atm/m. The heat exchange fluid may be in the form of a vapor, a liquid, or a mixture of vapor and liquid. The Reynolds Number for the flow of vapor through the heat exchange channels may be in the range from about 10 to about 5000, and in one embodiment about 100 to about 3000. The Reynolds Number for the flow of liquid through heat exchange channels may be in the range from about 10 to about 10000, and in one embodiment about 100 to about 5000.

The design of the process microchannels may vary along their axial length to accommodate the changing hydrodynamics within the process microchannels. For example, if one of the reactants is in excess, then the fluidic properties of a reaction mixture may change over the course of the reaction as typified by an extent of reaction less than about 10% to an extent of reaction greater than about 50%. For an oxidation reaction where oxygen is fed near the stoichiometric feed rate, at the entrance to the process microchannel the ratio of liquid to gas may be modest, but at the end of the process microchannel the ratio of liquid to gas may be high and approach infinity for reactions that are desired to go to extinction of the gas reactant. Reduction of mass transfer requires good phase mixing. Good phase mixing may require a different design as the gas or alternatively the liquid are reacted to near completion, for example, greater than about 60% conversion, and in one embodiment greater than about 90% conversion. There may be at least one second reaction zone in the process microchannel in which the microchannel cross section is reduced or increased from that in the corresponding first reaction zone to create a different mixing pattern. Surface features, if used, may have a different geometry, pattern, angle, depth, or ratio of size relative to the microchannel gap as the reaction proceeds toward extinction.

In one embodiment of the invention relatively short contact times, high selectivity to the desired product and relatively low rates of deactivation of the catalyst may be achieved by limiting the diffusion path required for the catalyst. For example, this may be achieved when the catalyst is in the form of a thin layer on an engineered support such as a metallic foam or on the wall of the process microchannel. This allows for increased space velocities. In one embodiment, the thin layer of catalyst can be produced using chemical vapor deposition. This thin layer may have a thickness in the range up to about 1 micron, and in one embodiment from about 0.1 to about 1 micron, and in one embodiment about 0.25 micron. These thin layers may reduce the time the reactants are within the active catalyst structure by reducing the diffusional path. This decreases the time the reactants spend in the active portion of the catalyst. The result may be increased selectivity to the product and reduced unwanted by-products. An advantage of this mode of catalyst deployment is that, unlike conventional catalysts in which the active portion of the catalyst may be bound up in an inert low thermal conductivity binder, the active catalyst film is in intimate contact with either the engineered structure or the wall of the process microchannel. This may leverage high heat transfer rates attainable in the microchannel reactor and allows for close control of temperature. The result is the ability to operate at increased temperature (faster kinetics) without promoting the formation of undesired by-products, thus producing higher productivity and yield and prolonging catalyst life.

In one embodiment, the catalyst may be regenerated. This may be done by flowing a regenerating fluid through the process microchannels 210 in contact with the catalyst. The regenerating fluid may comprise hydrogen or a diluted hydrogen stream. The diluent may comprise nitrogen, argon, steam, methane, carbon dioxide, or a mixture of two or more thereof. The concentration of $H_2$ in the regenerating fluid may range up to about 100% by volume, and in one embodiment from about 1 to about 100% by volume, and in one embodiment about 1 to about 50% volume. The regenerating fluid may flow from the header 104 through the process microchannels to the footer 106, or in the opposite direction from the footer 106 through the process microchannels to the header 104. The temperature of the regenerating fluid may be from about 20 to about 600° C., and in one embodiment about 20 to about 400° C., and in one embodiment about 80 to about 200° C. The pressure within the process microchannels 210 during this regeneration step may range from about 1 to about 100 atmospheres absolute pressure, and in one embodiment about 1 to about 10 atmospheres. The residence time for the regenerating fluid in the process microchannels may range from about 0.001 to about 10 seconds, and in one embodiment about 0.01 second to about 1 second.

The contact time of the reactants and product with the catalyst within the process microchannels 210 may be in the range up to about 100 seconds, and in one embodiment in the range from about 1 millisecond (ms) to about 100 seconds, and in one embodiment in the range from about 1 ms to about 50 seconds, and in one embodiment in the range from about 1 ms to about 25 seconds, and in one embodiment in the range from about 1 ms to about 10 seconds, and in one embodiment from about 1 ms to about 1 second, and in one embodiment from about 1 ms to about 500 ms, and in one embodiment about 1 ms to about 200 ms, and in one embodiment about 1 ms to about 100 ms, and in one embodiment about 1 ms to about 50 ms, and in one embodiment about 1 ms to about 20 ms, and in one embodiment about 1 ms to about 10 ms.

The flow rate of fluid flowing in the process microchannels 210 may be in the range from about 0.001 to about 500 lpm, and in one embodiment about 0.001 to about 250 lpm, and in one embodiment about 0.001 to about 100 lpm, and in one embodiment about 0.001 to about 50 lpm, and in one embodiment about 0.001 to about 25 lpm, and in one embodiment about 0.01 to about 10 lpm. The velocity of fluid flowing in the process microchannels may be in the range from about 0.01 to about 200 m/s, and in one embodiment about 0.01 to about 75 m/s, and in one embodiment about 0.01 to about 50 m/s, and in one embodiment about 0.01 to about 30 m/s, and in one embodiment about 0.02 to about 20 m/s. The Reynolds Number for the fluid flowing in the process microchannels may be in the range from about 0.0001 to about 100000, and in one embodiment about 0.001 to about 10000.

The weight hourly space velocity (WHSV) for the flow of the reactants and product in the process microchannels may be at least about 0.1 (ml feed)/(g catalyst)(hr). The WHSV may range from about 0.1 to about 5000, and in one embodiment, the WHSV may range from about 1 to about 500 (ml feed)/(g catalyst)(hr), and in one embodiment the WHSV may be in the range from about 10 to about 500 (ml feed)/(g catalyst)(hr).

The residence time for the flow of fluids in the process microchannels may be in the range from about 0.005 to about 100 seconds, and in one embodiment from about 0.03 to about 10 seconds.

While not wishing to be bound by theory, it is believed that a high superficial velocity in the process microchannels 210 may be advantageous for reactions wherein both gas and liquid phases are present during the reaction. This is because the shear stress force of the fluid may act to thin liquid layers that typically form on the surface of the catalyst. Thinner liquid film layers may reduce the mass transfer resistance of the reactants to the catalyst surface and improve conversion at relatively short contact times for the reactants, for example, contact times less than about 500 milliseconds. In one embodiment, the superficial velocity for the fluids flowing through the process microchannels may be at least about 0.01 meters per second (m/s), and in one embodiment in the range from about 0.01 to about 50 m/s, and in one embodiment in the range from about 0.01 to about 10 m/s, and in one embodiment in the range from about 0.01 to about 1 m/s, and in one embodiment in the range from about 0.05 to about 0.5 m/s.

The temperature of the fluids entering the microchannel processing unit 100 or processing unit core 102 may be in the range from about −40° C. to about 400° C., and in one embodiment about 0° C. to about 400° C., and in one embodiment from about 20° C. to about 300° C., and in one embodiment from about 20° C. to about 250° C., and in one embodiment from about 20° C. to about 200° C.

The temperature within the process microchannels 210 may be in the range from about −40° C. to about 400° C., and in one embodiment from about 0° C. to about 400° C., and in one embodiment from about 20° C. to about 300° C., and in one embodiment from about 20° C. to about 250° C., and in one embodiment from about 20° C. to about 200° C.

The temperature of the product exiting the microchannel processing unit 100 or processing unit 102 may be in the range from about −40° C. to about 400° C., and in one embodiment about 0° C. to about 400° C., and in one embodiment from about 20° C. to about 300° C., and in one embodiment from about 20° C. to about 250° C., and in one embodiment from about 20° C. to about 200° C.

The pressure within the process microchannels 210 may be in the range up to about 50 atmospheres absolute pressure, and in one embodiment up to about 40 atmospheres, and in one embodiment up to about 30 atmospheres. In one embodiment the pressure may be in the range from about 1 to about 50 atmospheres absolute pressure, and in one embodiment from about 10 to about 40 atmospheres, and in one embodiment from about 20 to about 30 atmospheres.

The pressure drop of the reactants and/or products as they flow in the process microchannels 210 may be in the range up to about 1 atmosphere per meter of length of the process microchannel (atm/m), and in one embodiment up to about 0.5 atm/m, and in one embodiment up to about 0.1 atm/m.

The pressure drop for the second fluid flowing through the apertured sections (250, 250A) may be in the range up to about 0.1 atm, and in one embodiment from about 0.001 to about 0.1 atm, and in one embodiment from about 0.001 to about 0.05 atm, and in one embodiment about 0.001 to about 0.005 atm. Reactants or products flowing in the process microchannels 210 may be in the form of a vapor, a liquid, or a mixture of vapor and liquid. The Reynolds Number for the flow of vapor in the process microchannels may be in the range from about 10 to about 10000, and in one embodiment about 100 to about 3000. The Reynolds Number for the flow of liquid in the process microchannels may be about 10 to about 10000, and in one embodiment about 100 to about 3000.

The conversion of the first reactant may be in the range from about 5% or higher per cycle, and in one embodiment from about 15 to about 100%.

The conversion of the second reactant may be in the range from about 25% or higher per cycle, and in one embodiment from about 25 to about 100% per cycle.

The yield of product may be in the range from about 20% or higher per cycle, and in one embodiment from about 20 to about 50% per cycle.

Emulsion formation within microchannels enables smaller mean droplet sizes for new commercial applications such as personal care, medical, and food products among others. When operated at a high flow rate per channel, the resulting emulsion mixture creates a high wall shear stress along the walls of the narrow microchannel. This high fluid-wall shear stress of continuous phase material past a dispersed phase, introduced through a permeable wall, enables the formation of small emulsion droplets—one drop at a time. These emulsions may be referred to as non-Newtonian fluids. A problem with the scale-up of this technology has been to understand the behavior of non-Newtonian fluids under high wall shear stress. A further complication has been the change in fluid properties with composition along the length of the microchannel as the emulsion is formed.

Many of the predictive models for non-Newtonian emulsion fluids are derived at low shear rates and have shown excellent agreement between predictions and experiments. The power law relationship for non-Newtonian emulsions obtained at low shear rates breaks down under the high shear environment created by high throughputs in small microchannels. The small dimensions create higher velocity gradients at the wall, resulting in larger apparent viscosity. Extrapolation of the power law obtained in low shear environments may not accurately predict pressure drops that may occur in microchannels at high flow rates.

The results for a shear-thinning fluid that generates larger pressure drops in a high-wall shear stress microchannel environment predicted from traditional correlations are described below. The following nomenclature is used:

f=fanning friction factor
D=hydraulic diameter of channel, m
k=power law constant
L=length of channel, m
n=power law coefficient
R=radius of the channel, m
Re=Reynolds number
V=average velocity of fluid in channel, m/s
$x^+$=dimensionless developing length
ΔP=pressure drop, Pa
ρ=density of fluid in channel, kg/m³
μ=viscosity, kg/m-s
τ=shear stress, N/m²
γ=shear rate, sec⁻¹

Emulsions may be referred to as dispersions containing a component that influences fluid-fluid interface stabilization. In many cases, the components of these emulsions as well as the emulsions do not follow the Newtonian relationship between shear stress and shear rate. The relationship between shear stress and shear rate plays an important role in predicting flow dynamics of non-Newtonian fluids as well as design parameters (e.g., pressure drop) for microchannel processing units.

When predicting pressure drop for a non-Newtonian fluid in a macro-scale pipe, rheological parameters such as the power law constants are used in conjunction with established theoretical or empirical correlations for velocity profile. Rheological parameters for velocity profile are often obtained from a benchtop rheometer or laboratory viscometer. However, because there are no well established correlations for velocity profile for a non-Newtonian fluid in a microchannel, translation of rheological parameters from a rheogram to a high shear environment and ultimately pressure drop can be inaccurate for small dimension systems.

Instead of using a rheogram as the basis for design calculations, it may be experimentally more convenient and accurate to use a pipeline viscometer (a form of a capillary viscometer) to measure rheological parameters for the high shear environment created in microchannels. The applicability of shear stress and shear rate relationship for shear thinning non-Newtonian fluid in microchannel environment is described below.

Most of the applications in the industry are limited by allowable pressure drop. The purpose of flow modeling is to understand and obtain the pressure drop in the system and parameters affecting it. This section describes equations that may be used for pressure drop estimation in straight conduits.

Newtonian Fluid

For Newtonian fluids, the shear stress changes proportional to shear rate. The constant of proportionality is called dynamic viscosity and is constant for a given fluid at constant temperature and pressure.

$$\tau = \mu \gamma \qquad (1)$$

Based on the above stress and strain relationship, the general form of pressure drop equation in a straight conduit with Newtonian fluid is given by:

$$\Delta P = 4f \frac{L}{D} \frac{\rho V^2}{2} \qquad (2)$$

Where the fanning friction factor (f) is a dimensionless number and represents the shear stress on the channel wall. The value of the friction factor depends on the flow regime (or Reynolds number), conduit geometry and wall surface roughness. The fanning friction factor for a circular channel geometry is dependent on the Reynolds number and is listed below.

Laminar Regime (Re<2200): The friction factor in laminar regime is dependent on dimensionless developing length and may be estimated by:

$$f = \frac{\left(\frac{3.44}{[x^+]^{0.5}}\right) + \frac{\left(\frac{1.25}{4[x^+]^{0.5}}\right) + 16 - \left(\frac{3.44}{[x^+]^{-0.5}}\right)}{1 + 0.00021(x^+)^{-2}}}{Re} ; \text{For } x^+ \leq 0.1 \qquad (3)$$

$$f = \frac{16}{Re}; \text{For } x^+ > 0.1 \quad (4)$$

Transition Regime (2200≦Re<4000): The friction factor in a circular channel for the transition regime may be given by:

$$f = 0.00128 + \frac{0.1143}{Re^{\frac{1}{3.2154}}} \quad (5)$$

Turbulent Regime (Re≧4000): The friction factor in circular channel for transition regime may be given by:

$$f = 0.0054 + \frac{2.3 \times 10^{-8}}{Re^{-1.5}} \quad (6)$$

The Reynolds number and dimensionless length may be given by $$Re = \frac{\rho V D}{\mu} \quad (7)$$

$$x^+ = \frac{L}{DRe} \quad (8)$$

Non-Newtonian Fluid

Figure 52:
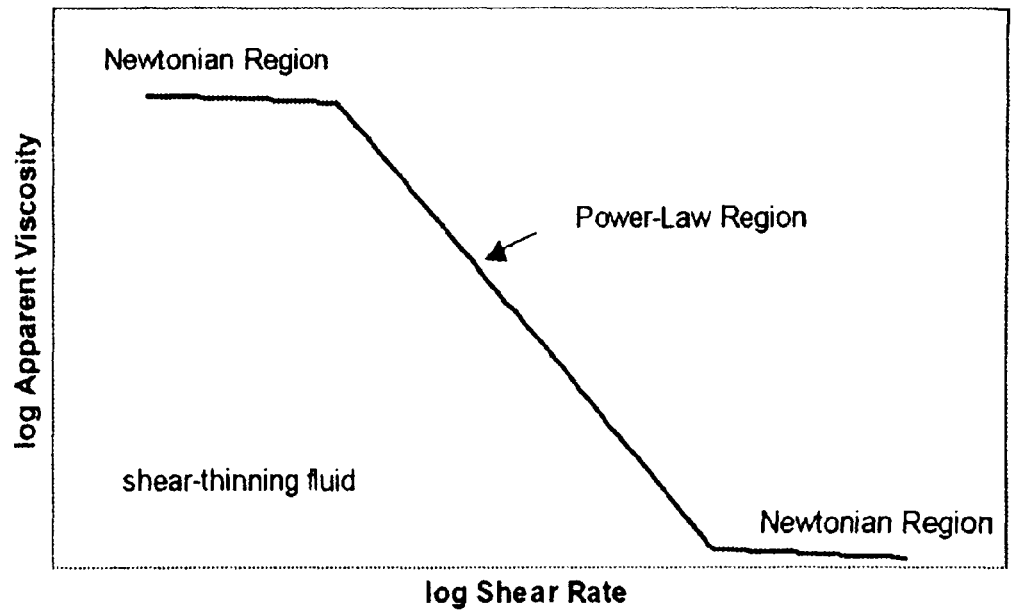
FIG. 52 is a plot of viscosity as a function of shear rate for a shear-thinning fluid.

For a shear-thinning non-Newtonian fluid the traditional relationship between shear stress and shear rate is shown in FIG. 52. The regions where the shear stress (or viscosity) does not change with shear rate may be referred to as Newtonian regions. The behavior between these regions may be a straight line on a log-log scale, and may be known as a power-law region.

The behavior of fluid in the power law region may be approximated by:

$$\mu = k\gamma^{n-1} \quad (9)$$

The fully developed velocity profile and shear rate for shear-thinning fluid obeying power law in laminar flow regime in a circular conduit may be given by:

$$\frac{V}{\bar{V}} = \frac{3n+1}{n+1}\left(1 - \left(\frac{r}{R}\right)^{\frac{n+1}{n}}\right) \quad (10)$$

$$\gamma = \bar{V}\left(\frac{3n+1}{n}\right)\frac{r^n}{R^{\frac{n+1}{n}}} \quad (11)$$

Generally, a mathematical problem involving a non-Newtonian fluid involves solving the Navier-Strokes equation. However, if the values of k and n can be determined by a viscometer, a simple method to estimate pressure drop with a non-Newtonian fluid can be developed by using power law relationships as described in equations (9), (10), (11) in conjunction with (2) to (4). This method of pressure drop estimation may be referred to as the 1-D method.

Figure 53:
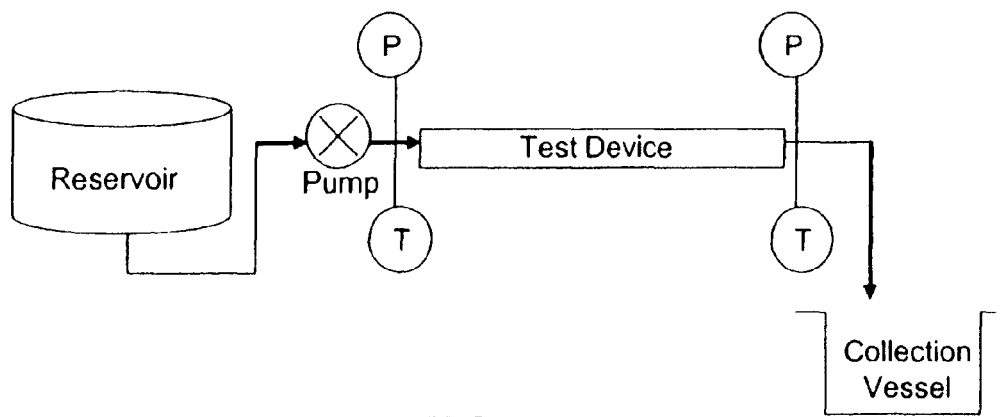
FIG. 53 is a schematic illustration of the experimental set-up used in the test discussed below for predicting pressure drop.

A test device for experimentally measuring the viscosity in a high shear rate environment is illustrated in FIG. 53. A stainless steel tube with a circular cross-section is used. The nominal tube diameter is 1.59 mm. The nominal thickness of the tube wall is 0.43 mm. The length of the tube is 610 mm. The test apparatus is prepared by cutting the required length of tubing from the coil stock and removing the burrs at both ends of the tube using a de-burrer.

Fluid is fed by a syringe pump, Isco model 260D. The pump is accurate to 0.001 ml/min. The maximum delivery pressure for the pump is 20,800 kPa (205.3 atmospheres). The pressure of the liquid, at the inlet and the outlet of the test apparatus, is measured using pressure transducers-NOSHOK Series 100. A single pressure transducer is used at the outlet of the test apparatus with range from 0 to 136 kPa (5 psig, 1.34 atmospheres). At the inlet of the test device, two pressure transducers are used. One transducer has range from 0 to 791 kPa (100 psig, 7.81 atmospheres), while the other pressure transducer has range from 0 to 7000 kPa (1000 psig, 69.1 atmospheres). When the inlet pressure is less than 710 kPa (7.01 atmospheres), the pressure transducer with range from 0 to 791 kPa (7.81 atmospheres) is used otherwise the pressure transducer with range 0 to 7000 kPa (69.1 atmospheres) is used. The accuracy of the pressure transducers is ±0.5% of the pressure range. The outlet of the test device is kept at ambient pressure conditions. The inlet and the outlet temperature of the fluid to the test apparatus is measured using Omega Type K thermocouples with accuracy of ±2° C. The entire test device is kept at ambient temperature conditions. Any viscous heat generation is dissipated to the ambient.

The connections to the test device are made using graphite ferrules and swagelok fittings to prevent compression of the tube at the ends.

The temperature and pressure data are electronically recorded using National Instruments Labview 7.1. The interval of data recording is 1 second.

Figure 54:
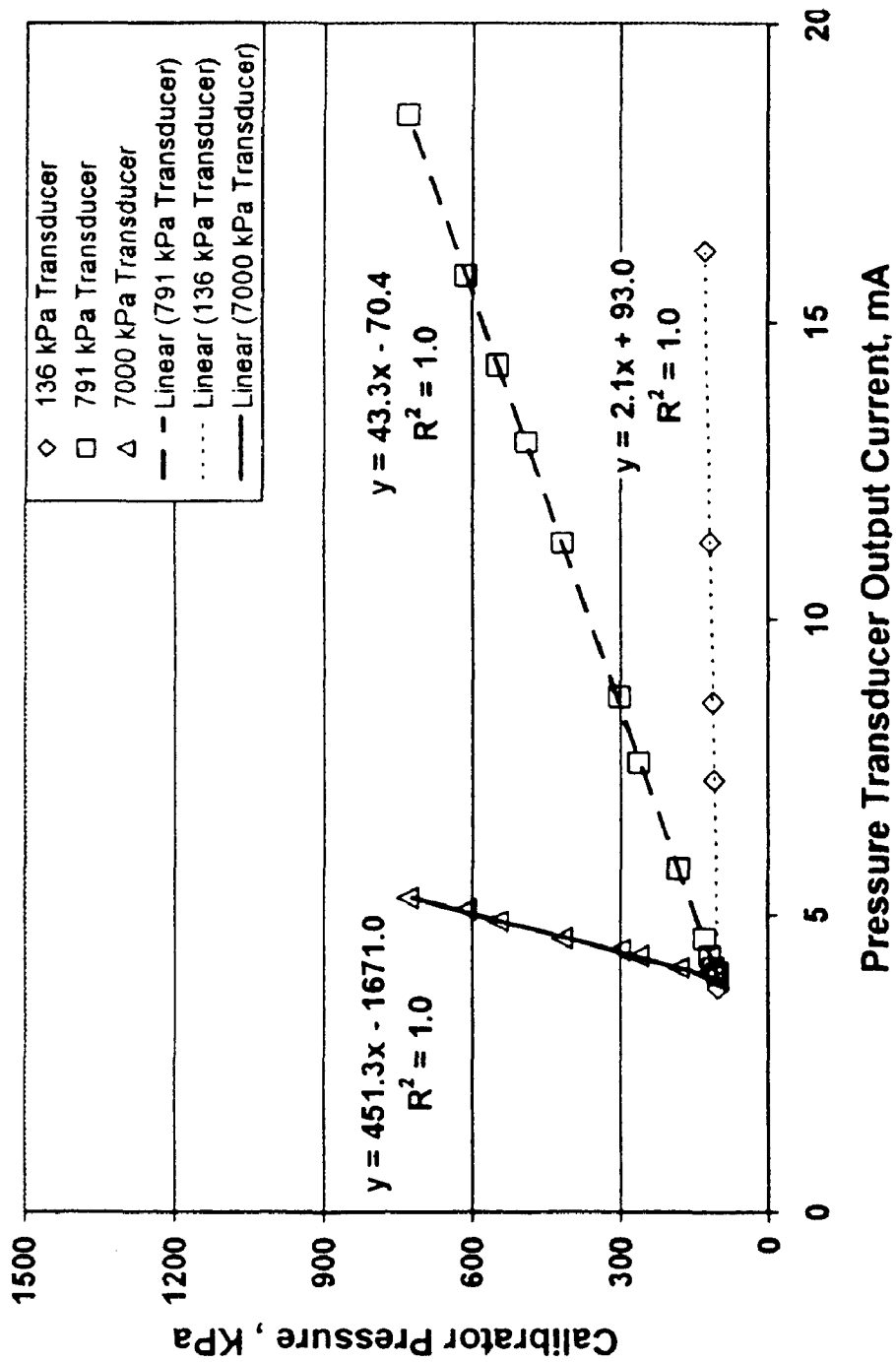
FIG. 54 is a plot showing calibration curves for pressure transducers used in the test discussed below for predicting pressure drop.

Prior to performing any experiments, the pressure transducers are calibrated for accurate pressure measurement. The standard used for calibration is Fluke 725 w/700PO7 pressure module. The calibration curve is built by comparing raw pressure transducer output current (in mA) read by the data logging Labview software against the pressure measured by Fluke725 equipped with a pressure module (in kPa). The pressure is introduced using Altech 368-600 high pressure hand pump. Minimum six points are used to generate the calibration curves. The relations between the applied pressure and pressure transducer signal are found to be linear for all three pressure transducers. The calibration curves are then used for pressure measurements during the experiments. FIG. 54 shows the calibration curve for 136 kPa (1.34 atmospheres), 791 kPa (7.81 atmospheres) and 7000 kPa (69.1 atmospheres) range pressure transducers.

The accuracy of the pump is measured to be within ±0.5%.

An experimental test plan is developed to estimate pressure drop for both a Newtonian and a non-Newtonian fluid. The Newtonian fluid that is used is de-ionized water. The non-Newtonian fluid is prepared using rheology modifier dissolved in de-ionized water. The rheology modifier used is Carbopol SF-1 from Noveon. The experimental test plan is shown in Table 1.

TABLE 1

Experimental test plan for Newtonian and non-Newtonian fluids

| Run number | Flow rate (ml/min) | Outlet pressure (kPa) | Test Temperature (° C.) |
|---|---|---|---|
| 1 | 10.0 | Ambient | Ambient |
| 2 | 21.3 | Ambient | Ambient |
| 3 | 32.5 | Ambient | Ambient |
| 4 | 43.8 | Ambient | Ambient |

TABLE 1-continued

Experimental test plan for Newtonian and non-Newtonian fluids

| Run number | Flow rate (ml/min) | Outlet pressure (kPa) | Test Temperature (° C.) |
|---|---|---|---|
| 5 | 55.0 | Ambient | Ambient |
| 6 | 77.5 | Ambient | Ambient |
| 7 | 88.8 | Ambient | Ambient |
| 8 | 100.0 | Ambient | Ambient |

Deionized water is used as the Newtonian fluid. The deionized water is prepared by using a deionizer manufactured by Elga, model Medica 17R. The setting is at 18MΩ.

Three non-Newtonian solutions are prepared using the Noveon Carbopol polymer. Carbopol polymers are high molecular weight homo- and copolymers of acrylic acid crosslinked with a polyalkenyl polyether. When used at concentrations lower than 1%, these polymers offer a wide range of rheological properties. The first solution is prepared by mixing 4.2 g of Carbopol polymer in 500 g of de-ionized water. The second solution is made by mixing 5.6 g of Carbopol polymer in 500 g of de-ionized water. The third solution is made by mixing 8.4 g of Carbopol polymer in 500 g of de-ionized water. All the solutions are brought to pH 6.8-7.2 by dropwise addition of 0.1N NaOH, stirring while the pH is monitored. The first solution is referred as low viscosity, the second solution is referred as medium viscosity while the third solution is referred as high viscosity. Each of these are non-Newtonian fluids.

The viscosity of non-Newtonian fluids is measured using Brookfield RVDV-E viscometer equipped with a UL adapter. The spindle used for viscosity measurement is ULA-000.

Figure 55:
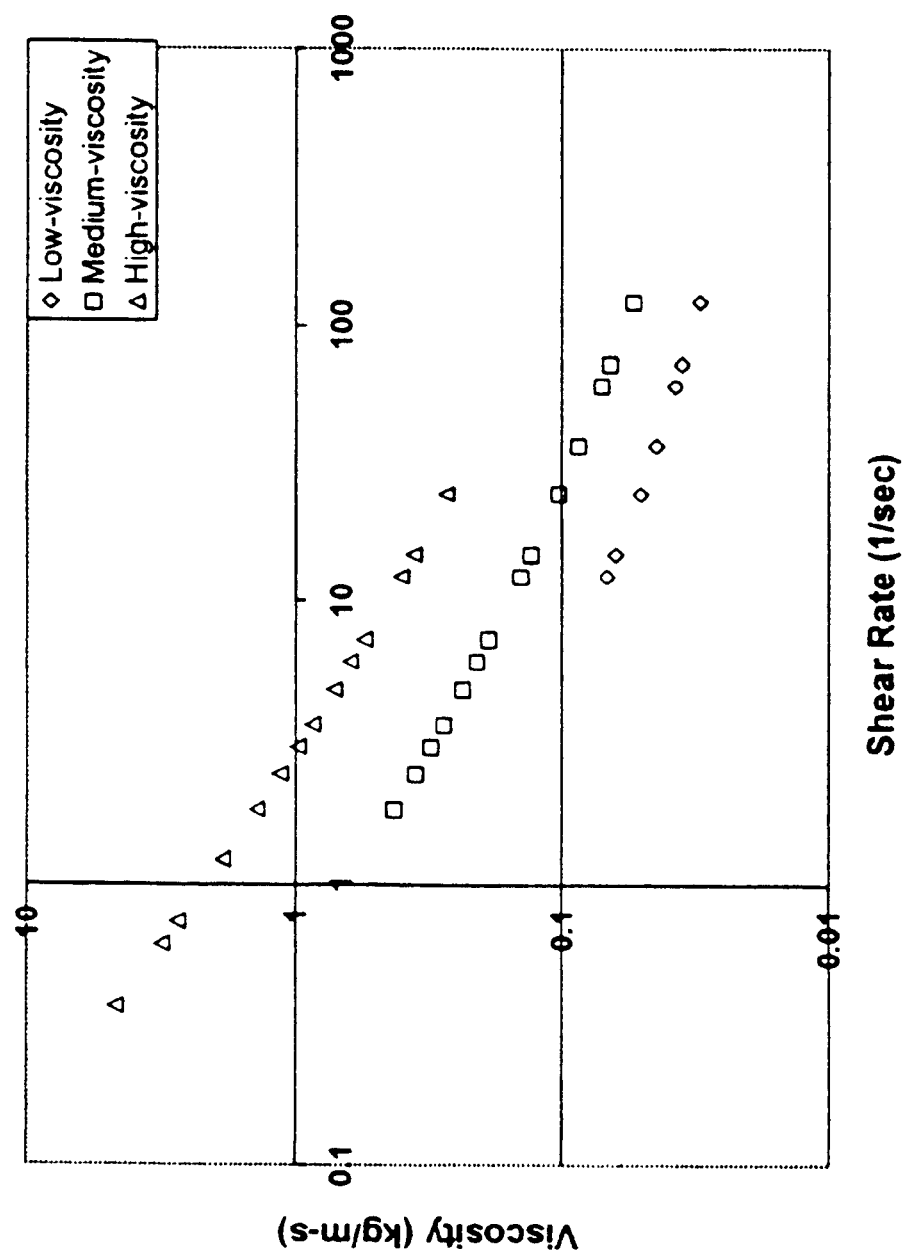
FIG. 55 is a plot showing viscosity as a function of shear rate for non-Newtonian fluids measured using a Brookfield viscometer.

FIG. 55 shows the measured viscosity of the Carbopol solution as a function of shear rate for low, medium and high viscosity non-Newtonian fluids as tested by a Brookfield viscometer.

The linear relationship between viscosity and shear rate on a log-log scale indicates that the fluid is a shear-thinning non-Newtonian fluid following a traditional power law relationship.

The reservoir of the pump is filled with the testing fluid. The data recording is started to electronically record the pressures and temperatures. The required flow rate to the test device is set in the syringe pump and the syringe pump is started. The flow is considered steady-state when the fluctuation in the inlet pressure transducer is less than 3.5 kPa (0.035 atmosphere). The steady state is maintained for 30 to 60 seconds to collect inlet and outlet pressure and temperature information. After all the test runs for a fluid are completed, the system is purged by pumping 50 ml of air, flushed with 20 ml of the next fluid before beginning the tests. Several run points are repeated to validate the reproducibility. The pressure drop across the test device is calculated by difference of inlet and outlet measured pressures.

Figure 56:
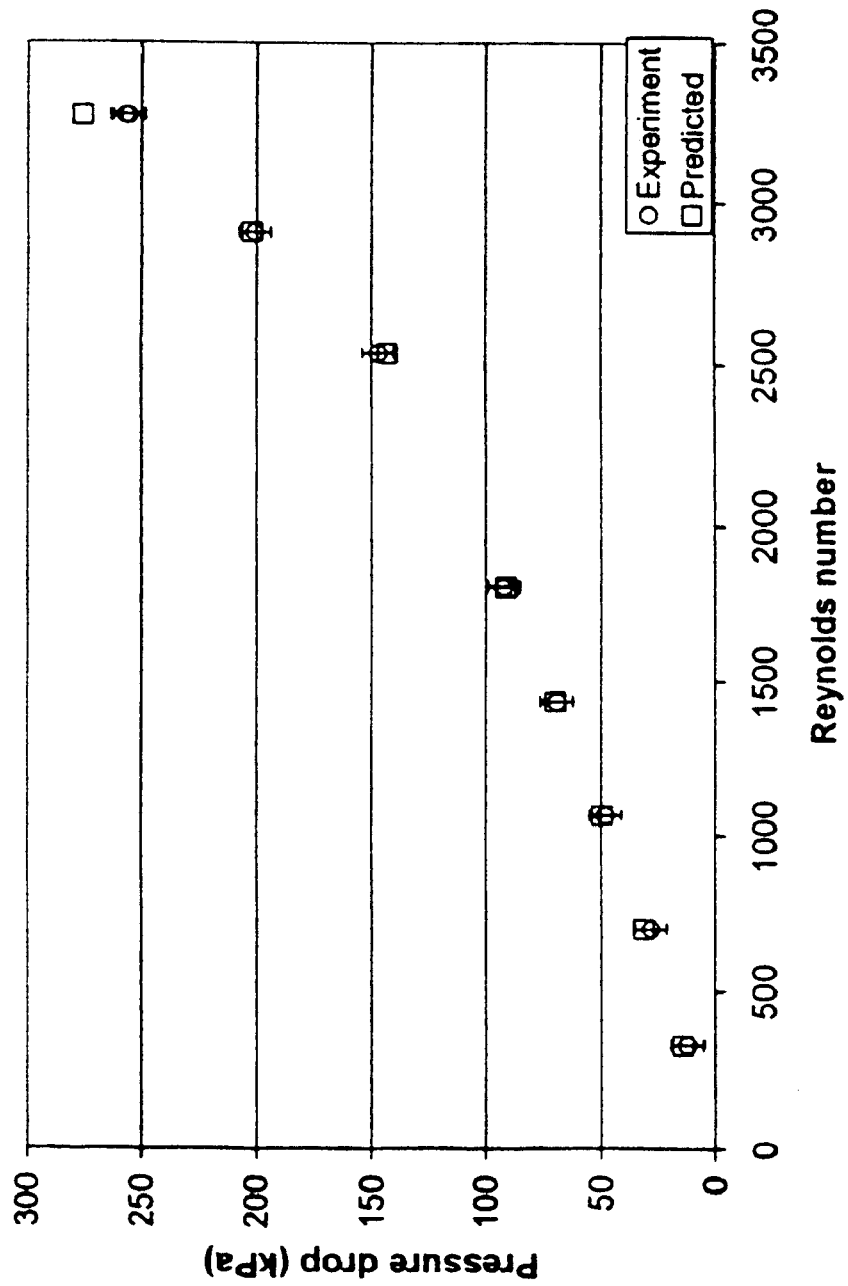
FIG. 56 is a plot showing a comparison of experimental and predicted pressure drops for de-ionized water, the de-ionized water being a Newtonian fluid.

FIG. 56 shows the comparison of experimental pressure drop with predictions for water. Equations (2) through (8) are used for the predictions of pressure drop. As shown in FIG. 56, there is an excellent agreement between measured pressure drop and predicted pressure drop for water as a Newtonian fluid. The comparison validates the selected friction factor correlations.

The viscosity measurements made by a Brookfield viscometer, as shown in FIG. 55, are used to calculate constants k and n in the power law relationship between viscosity and shear rate. The values of k and n for low, medium and high viscosity non-Newtonian fluid are summarized in Table 2.

TABLE 2

Summary of k and n values for non-Newtonian fluid from Brookfield viscometer

|  | k | N |
|---|---|---|
| Low Viscosity | 0.16 | 0.65 |
| Medium Viscosity | 0.55 | 0.49 |
| High Viscosity | 2.13 | 0.33 |

Figure 57:
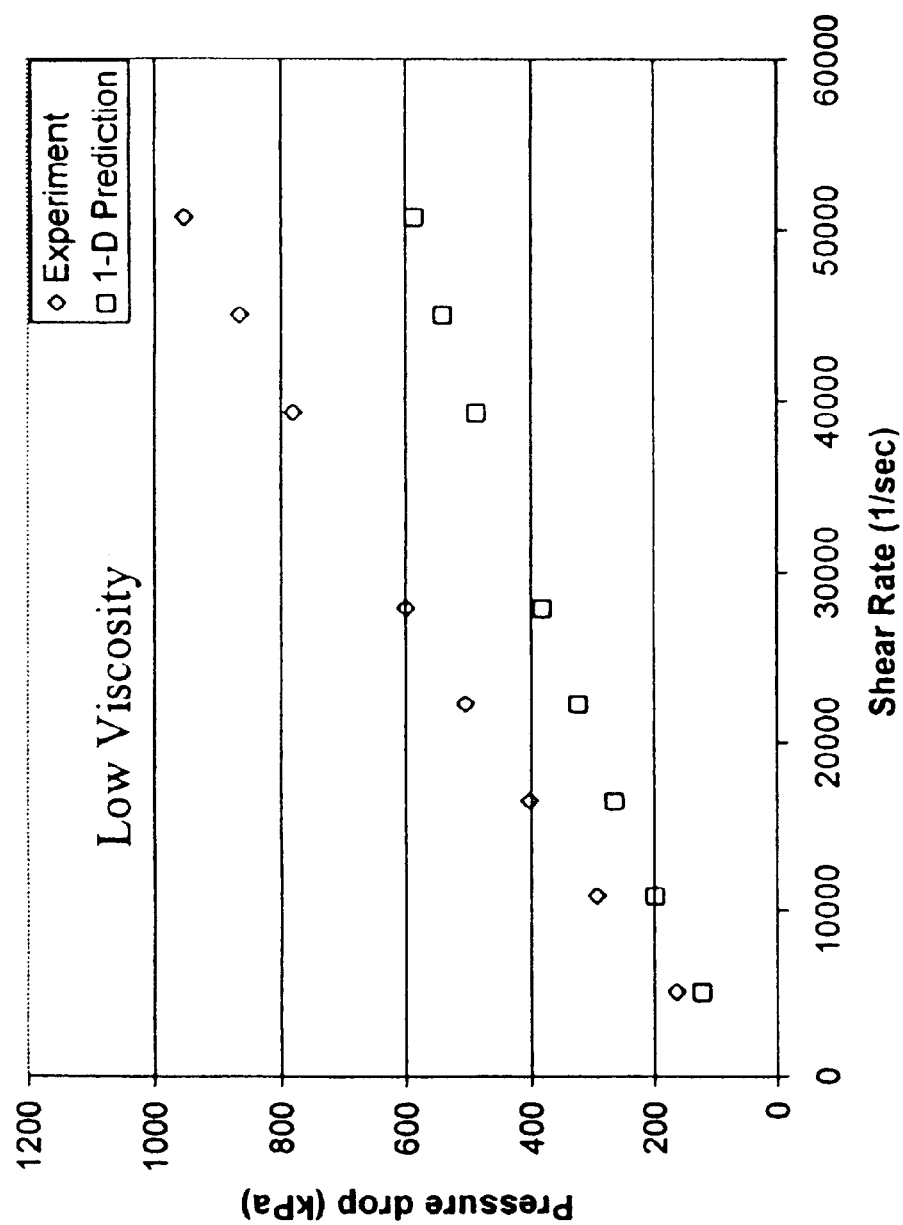
FIG. 57 is a plot showing a comparison of experimental pressure drop with pressure drop predicted using Brookfield viscometer information for a low viscosity non-Newtonian fluid.
Figure 58:
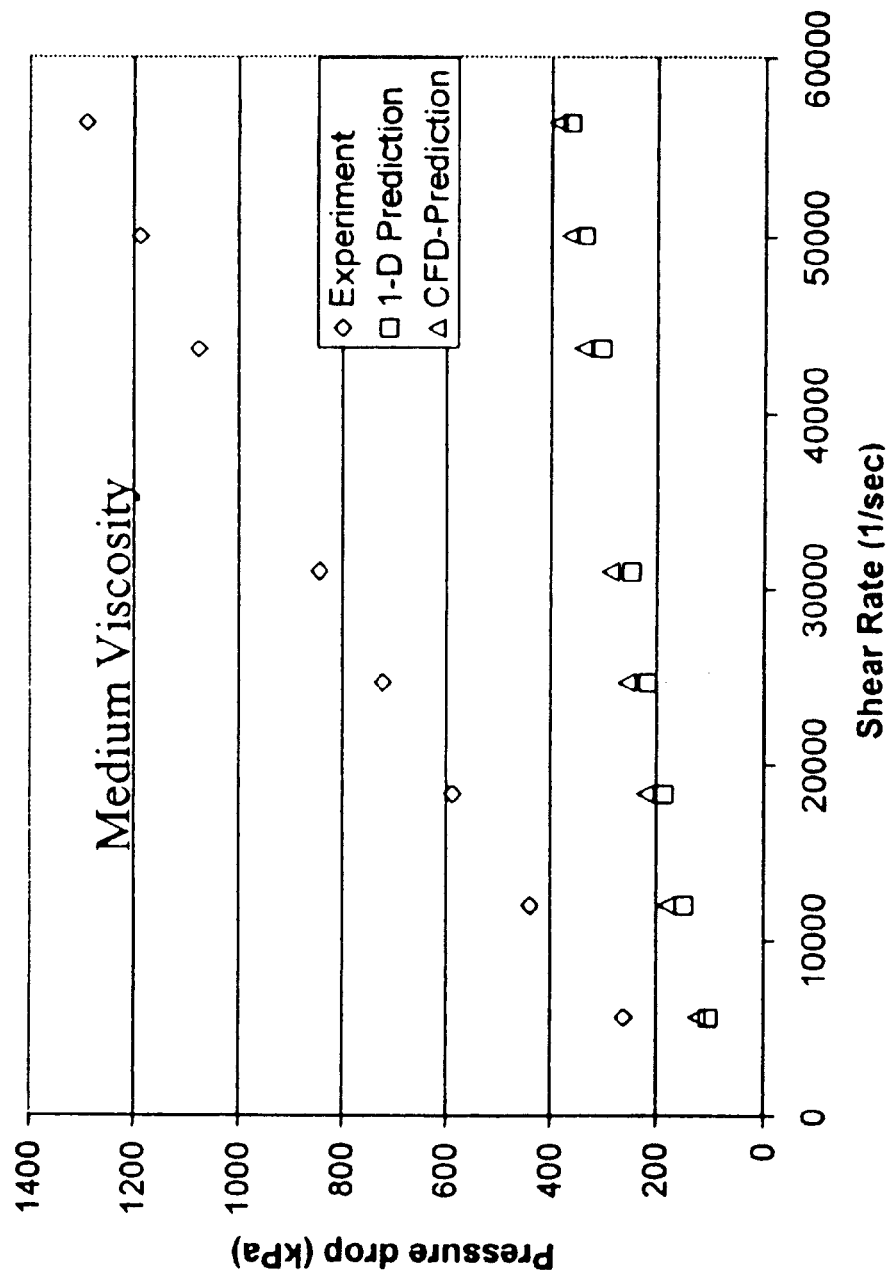
FIG. 58 is a plot showing a comparison of experimental pressure drop with pressure drop predicted using Brookfield viscometer information for a medium viscosity non-Newtonian fluid.

Using the equations (2), (9-11) and values of k and n in Table 2, pressure drop is predicted for low, medium and high viscosity non-Newtonian fluid in the test device. FIGS. 57-59 compare the experimental pressure drop and the predicted pressure drop for low, medium and high viscosity non-Newtonian fluids. In all the cases, the experimental pressure drop is larger than the pressure drop predicted by the 1-D method that is based on the fit of the power law coefficients obtained in the low shear Brookfield viscometer.

Computation fluid dynamics method is also used to validate the 1-D method. A simple mesh of the test device is developed in Gambit. The software used for computation fluid dynamics is Fluent V6.2.16. The power law coefficients obtained from Brookfield Viscometer, as listed in Table 2, are used in the analysis. A good agreement is observed between the predictions from the computation fluid dynamics method and the 1-D method as shown in FIG. 58.

The pressure drop predictions for non-Newtonian fluids made by both the 1-D method and the computational fluid dynamics method, using k and n values obtained from low shear Brookfield viscometer testing, are significantly lower than the measured experimental pressure drop (as shown in FIGS. 57-59). Also the discrepancy between the predictions and measurements increases as the viscosity of the non-Newtonian fluid increases.

The Brookfield viscometer estimates the viscosity of the non-Newtonian fluid between 0.1 and 100 $\sec^{-1}$ shear rate. This range of shear rates is used to estimate the power law relationship between the viscosity and shear rate. However, as shown in FIGS. 57-59, the shear rates in the test device are in the range from 5000 to 50,000 $\sec^{-1}$. These higher shear rates are typical for operation in a microchannel emulsification device. The discrepancy between the predicted and the measured pressure drop indicates that the power law relationship estimated by viscometer may not be adequate for accurate prediction of the pressure drop in a microchannel.

Figure 60:
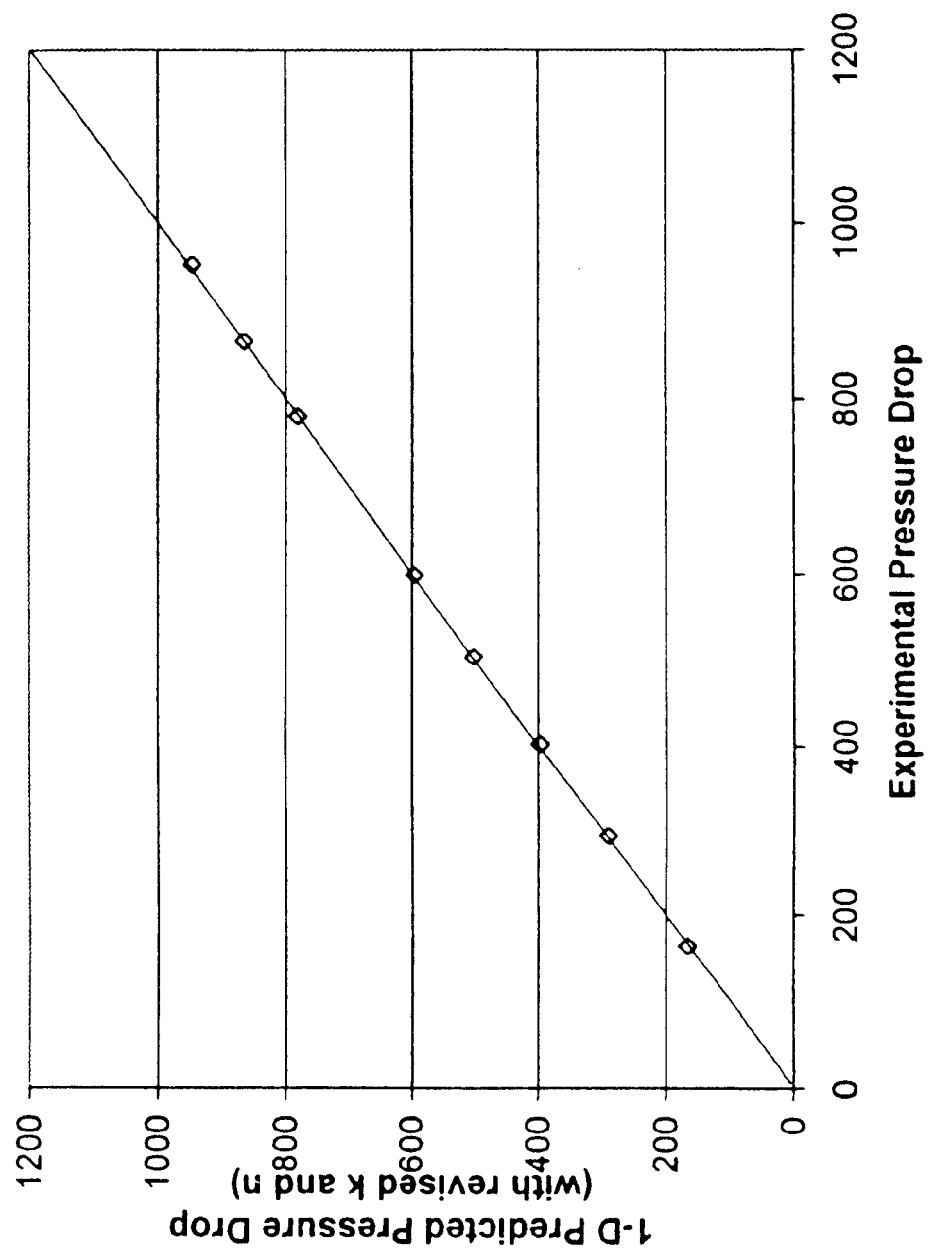
FIG. 60 is a plot showing a comparison of experimental pressure drop and prediction with new k and n values for a low viscosity fluid.

Using the experimental pressure drop data, k and n values are recalculated to match predictions with experimental pressure drop. The new values of k and n are significantly different from values estimated by viscometer indicating a different viscosity-shear rate relationship at high shear rates. Table 3 summarizes the comparison. FIG. 60 shows a comparison of experimental pressure drop and predictions using the new k and n values for the low viscosity fluid. The results for the medium and high viscosity fluid are similar and the error in predictions is less than 1%.

This apparent discrepancy is attributed to a change in the power law relationship of the non-Newtonian fluid between a low to high shear rate environment at microchannel dimensions. While not wishing to be bound by theory, it is believed that the small channel dimensions and high throughput in the microchannels may cause changes to the laminar fluid profile. The increased value of n suggests that the velocity profile is further flattened. The effect of the flattened fluid profile may increase the apparent viscosity at the wall and results in higher pressure drop in the microchannel.

Figure 61:
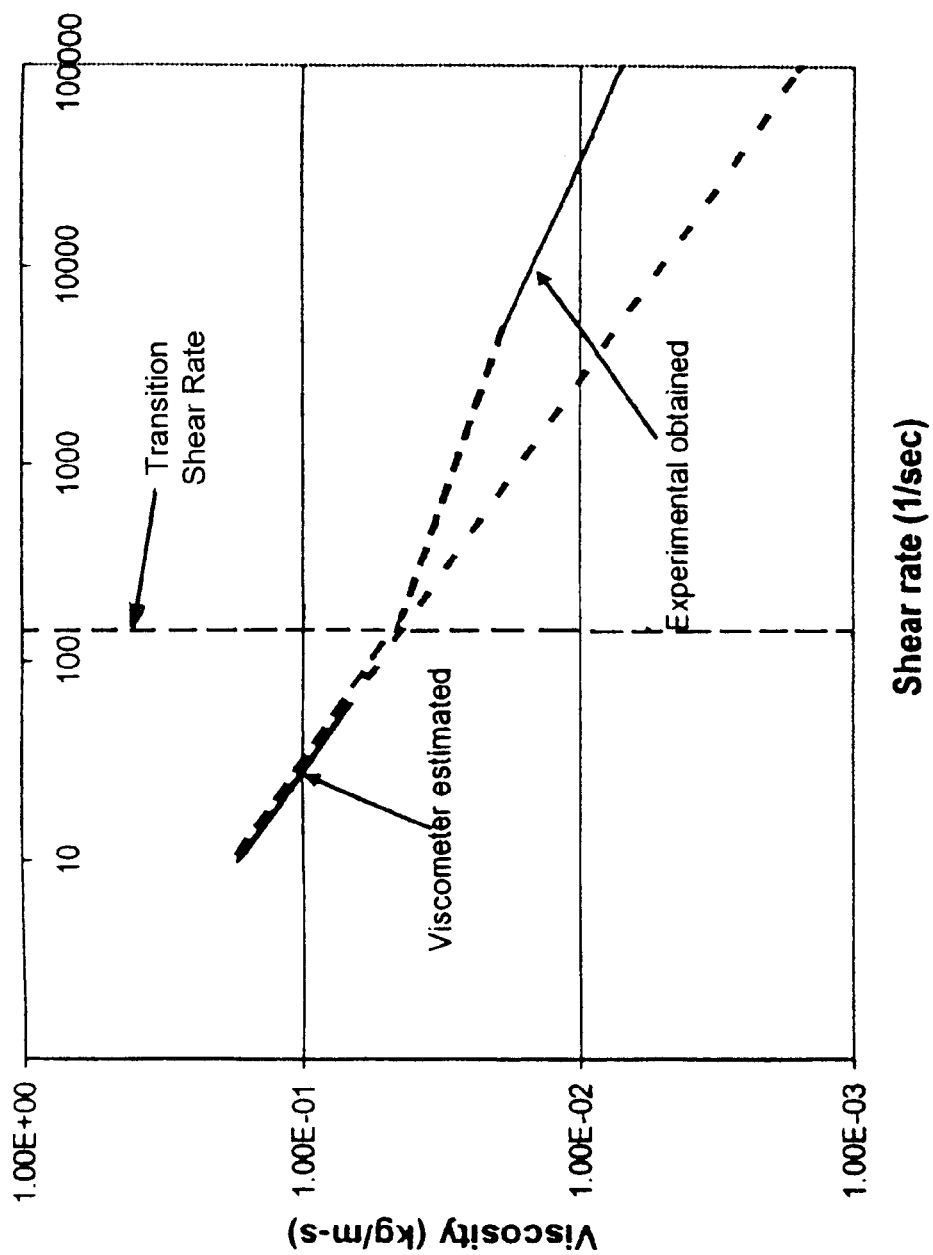
FIG. 61 is a plot showing theorized behavior of viscosity-shear rate relationship of a power law fluid in a microchannel.

Further, additional experiments are performed in the tube viscometer under low shear, and the resulting values of k and n match that predicted by the Brookfield viscometer in this low shear rate regime as shown in Table 4. The theorized relationship between viscosity and shear rate for power-law non-Newtonian fluid in a microchannel is shown in FIG. 61. At the transition shear rate, there is a change in the viscosity-shear rate relationship.

TABLE 3

Comparison of k and n values estimated by Brookfield viscometer and calculated from high shear experimental data

| | Brookfield Viscometer | | Estimation from experimental data | |
|---|---|---|---|---|
| | K | n | k | n |
| Low Viscosity | 0.16 | 0.65 | 0.10 | 0.74 |
| Medium Viscosity | 0.55 | 0.49 | 0.28 | 0.68 |
| High Viscosity | 2.13 | 0.33 | 0.66 | 0.62 |

TABLE 4

Comparison of k and n values estimated by Brookfield viscometer and calculated from low shear experimental tube data

| | Brookfield Viscometer | | Estimation from experimental data | |
|---|---|---|---|---|
| | k | n | k | N |
| Medium Viscosity | 0.55 | 0.49 | 0.53 | 0.55 |

The power law relationship between viscosity and shear rate for a shear thinning non-Newtonian fluid estimated by a laboratory viscometer is generally in the low shear rate range. The high velocity shear-thinning non-Newtonian flow through microchannels with small characteristics dimensions results in high shear rates. At these high shear rates, the power law estimated by the low shear laboratory viscometer may not be accurate for pressure drop predictions. Good predictive pressure drop models for micro-channel dimensions may be obtained for non-Newtonian fluids by the foregoing pressure drop test with fluid and flow rates in the region of interest. The models developed by this method may be used for accurate predictions and system design. Further, the results suggest that the fluid profile within the narrow channel changes in a high shear environment, such that the apparent viscosity increases.

Though the difference between the viscosity-shear rate relationship extrapolated from a viscometer measurements and the actual viscosity-shear rate relationship for high shear rate flow in microchannels is observed for shear-thinning fluid. It is possible that for other types of non-Newtonian fluids such as shear-thickening, time-dependent fluid (thixotropic, rheopectic), viscometer measurements at low shear rates may not be applicable for high shear rate flow in microchannels.

Utilization of the accurate pressure drop models discussed here may be used to design processes and apparatuses using a plurality of microchannels in a microchannel processing unit or a module for a microchannel processing unit. The fluid introduced into one microchannel processing unit may flow through a manifold section and then into a plurality of microchannels. Channel dimensions and flow restrictions may be selected using the models to obtain sufficient flow distribution among to channels to obtain the desired result of unit operations being performed in the device. Unit operations may include reactions, separations, heating, cooling, vaporization, condensation, mixing, and the like. One measure of flow distribution is the Quality Index Factor. The Quality Index Factor "$Q_1$" may be a measure of how effective a manifold is in distributing flow. It is the ratio of the difference between the maximum and minimum rate of connecting channel flow divided by the maximum rate. For systems of connecting channels with constant channel dimensions it may be desired to achieve equal mass flow rate per channel. The equation for this case may be as follows:

$$Q_1 = \frac{m_{max} - m_{min}}{m_{max}} \times 100\%$$

where
$m_{max}$ [kg/sec]=maximum connecting channel mass flow rate
$m_{min}$ [kg/sec]=minimum connecting channel mass flow rate
For cases where there are varying connecting channel dimensions it may be desired that the residence time, contact time, velocity or mass flux rate have minimal variation from channel to channel such that the required duty of the unit operation may be attained. For those cases the Quality Index Factor may be defined as:

$$Q_2 = \frac{G_{max} - G_{min}}{G_{max}} \times 100\%,$$

where G is the mass flux rate. For cases when all the connecting channels have the same cross sectional area, the equation for $Q_2$ simplifies to $Q_1$. The Quality Index Factor gives the range of connecting channel flow rates, with 0% being perfect distribution, 100% showing stagnation (no flow) in at least one channel, and values of over 100% indicating backflow (flow in reverse of the desired flow direction) in at least one channel. $Q_1$ and $Q_2$ may be defined based on the channels that comprise about 95% of the net flow through the connecting channels wherein the lowest flow channels are not counted if the flow through those channels is not needed to account for about 95% of the net flow through the connecting channels. The Quality Index Factor may be about 20% or less, and in one embodiment about 5% or less, and in one embodiment about 1% or less. In one embodiment, the Quality Index Factor may be in the range from about 0.5% to about 5%.

While the invention has been explained in relation to specific embodiments, it is to be understood that various modifications thereof will become apparent to those skilled in the art upon reading the specification. Therefore, it is to be understood that the invention covered herein is intended to include such modifications as may fall within the scope of the appended claims.

The invention claimed is:
1. A process, comprising:
conducting unit operations in at least two process zones in a process microchannel to treat and/or form a non-Newtonian fluid, a different unit operation being conducted in each process zone; and
applying an effective amount of shear stress to the non-Newtonian fluid to reduce the viscosity of the non-Newtonian fluid in each process zone, the average shear rate in one process zone differing from the average shear rate in another process zone by a factor of at least about 1.2;

wherein the unit operations are selected from conducting a chemical reaction using two or more fluids to form a non-Newtonian fluid, conducting a chemical reaction using one or more non-Newtonian fluids as a reactant or a combination of two or more thereof.

2. The process of claim 1 wherein the average shear rate in at least one process zone is in excess of about 100 sec$^{-1}$.

3. The process of claim 1 wherein the process microchannel has a converging cross-sectional area in at least one process zone, the shear stress being applied to the non-Newtonian fluid by flowing the non-Newtonian fluid through the converging cross-sectional area.

4. The process of claim 1 wherein the process microchannel comprises surface features on and/or in one or more interior surfaces in at least one process zone, the shear stress being applied to the non-Newtonian fluid by flowing the non-Newtonian fluid in contact with the surface features.

5. The process of claim 1 wherein the process microchannel comprises one or more interior structured walls in at least one process zone, the shear stress being applied to the non-Newtonian fluid by flowing the non-Newtonian fluid in contact with one or more structured walls.

6. The process of claim 1 wherein the process microchannel comprises one or more internal obstructions in at least one process zone, the shear stress being applied to the non-Newtonian fluid by flowing the non-Newtonian fluid in contact with one or more internal obstructions.

7. The process of claim 1 wherein the viscosity of the non-Newtonian fluid in at least one process zone is reduced to a viscosity of up to about $10^5$ centipoise.

8. The process of claim 1 wherein the non-Newtonian fluid comprises at least one polymer, polymer composition, multiphase fluid mixture or emulsion.

9. The process of claim 1 wherein the non-Newtonian fluid comprises at least one polymer, the polymer comprising repeating units derived from one or more polymerizable olefins, cyclic olefins, dienes, ethers, esters, amides, carbonates, acetates, acrylics, alkylacrylics, acrylates, alkylacrylates, vinyl acetate, styrene, vinyls, vinylidenes, acrylonitrite, cyanoacrylates, tetrafluoroethylene, and combinations of two or more thereof.

10. The process of claim 1 wherein the non-Newtonian fluid comprises at least one polymer, the polymer comprising polyethylene, polypropylene, polystyrene, rubber modified polystyrene, styrene-butadiene copolymer, vinyl polymer, vinyl copolymer, acrylonitrile-butadiene-styrene copolymer, polymethylmethacrylate, polycarbonate, or a mixture of two or more thereof.

11. The process of claim 1 wherein the non-Newtonian fluid comprises at least one polymer, the polymer being derived from ethylene and/or propylene, and one or more monomers comprising acrylate, alkylacrylate, acrylic acid, alkylacrylic acid and/or vinyl acetate.

12. The process of claim 1 wherein the non-Newtonian fluid comprises at least one polymer, the polymer comprising natural rubber, reclaimed rubber, synthetic rubber, or a mixture of two or more thereof.

13. The process of claim 1 wherein the non-Newtonian fluid comprises at least one polymer, the polymer comprising one or more polymers of acrylic acid crosslinked with one or more polyakenyl polyethers.

14. The process of claim 1 wherein the non-Newtonian fluid comprises a multiphase mixture, the multiphase mixture comprising water and/or at least one organic liquid.

15. The process of claim 1 wherein non-Newtonian fluid comprises a multiphase mixture, the multiphase mixture comprising at least one liquid hydrocarbon.

16. The process of claim 1 wherein the non-Newtonian fluid comprises a multiphase mixture, the multiphase mixture comprising at least one natural oil, synthetic oil, or mixture thereof.

17. The process of claim 1 wherein the non-Newtonian fluid comprises a multiphase mixture, the multiphase mixture comprising one or more: emulsifiers; surfactants; UV protection factors; waxes; consistency factors; thickeners; superfatting agents; stabilizers; cationic, anionic, zwitterionic, amphoteric or nonionic polymers; silicone compounds; fats; waxes; lecithins; phospholipids; biogenic agents; antioxidants; deodorants; antiperspirants; antidandruff agents; swelling agents; insect repellents; self-tanning agents; tyrosine inhibitors; solubilizers; preservatives; perfume oils; or dyes; or a mixture of two or more thereof.

18. The process of claim 1 wherein the non-Newtonian fluid comprises a multiphase mixture, solids being dispersed in the multiphase mixture.

19. The process of claim 1 wherein a first fluid and a second fluid are in the process microchannel; the first fluid, second fluid, mixture of the first fluid and second fluid, and/or product made by reacting the first fluid with the second fluid being a non-Newtonian fluid.

20. The process of claim 1 wherein the non-Newtonian fluid comprises a mixture of at least one first fluid and at least one second fluid or a product made by reacting at least one first fluid with at least one second fluid, at least one staged addition channel being adjacent to the process microchannel and at least one apertured section being positioned between the at least one staged addition channel and the process microchannel, the first fluid flowing in the process microchannel, the second fluid flowing from the at least one staged addition channel through the at least one apertured section into at least one process zone in the process microchannel in contact with the first fluid.

21. The process of claim 1 wherein the process microchannel is formed from parallel spaced sheets and/or plates.

22. The process of claim 20 wherein the process microchannel and the staged addition channel are formed from parallel spaced sheets and/or plates, the process microchannels and staged addition channels being positioned side-by-side or stacked one above another.

23. The process of claim 1 wherein the process microchannel exchanges heat with at least one heat exchange channel, the process microchannel and heat exchange channel being formed from parallel spaced sheets and/or plates, the heat exchange channel being adjacent to and/or in thermal contact with the process microchannel.

24. The process of claim 20 wherein the apertured section comprises at least one sheet and/or plate with a plurality of apertures in the sheet and/or plate.

25. The process of claim 20 wherein the apertured section is made from a porous material.

26. The process of claim 1 wherein heat is exchanged between the process microchannel and a heat source and/or heat sink.

27. The process of claim 26 wherein the heat source and/or heat sink comprises at least one heat exchange channel.

28. The process of claim 27 wherein a heat exchange fluid is in the heat exchange channel.

29. The process of claim 26 wherein the heat source and/or heat sink comprises an electric heating element, a resistance heater and/or a non-fluid cooling element.

30. The process of claim 4 wherein the surface features are in the form of depressions in and/or projections from one or more of the microchannel interior walls that are oriented at oblique angles relative to the direction of flow of fluid through the microchannel.

31. The process of claim 4 wherein the surface features are in the form of at least two surface feature regions wherein mixing of the first fluid and second fluid is conducted in a first surface feature region followed by flow in a second surface feature region wherein the flow pattern in the second surface feature region is different than the flow pattern in the first surface feature region.

32. The process of claim 1 wherein the non-Newtonian fluid is a reactant and/or a product in a chemical reaction, the reaction being a gas-liquid reaction, liquid-liquid reaction, gas-liquid-liquid reaction, gas-liquid-solid reaction, or a liquid-liquid-solid reaction.

33. The process of claim 1 wherein the non-Newtonian fluid is a reactant and/or a product in a chemical reaction, the reaction being an oxidation reaction, hydrocracking reaction, hydrogenation reaction, hydration reaction, carbonylation reaction, sulfation reaction, sulfonation reaction, oligomerization reaction or polymerization reaction.

34. The process of claim 1 wherein at least one unit operation comprises a chemical reaction wherein the non-Newtonian fluid is a reactant and/or a product, the chemical reaction being conducted in the presence of a catalyst.

35. The process of claim 34 wherein the catalyst comprises a homogeneous catalyst, or is in the form of particulate solids, is washcoated on one or more interior surfaces of the process microchannel, or is grown on one or more interior surfaces of the process microchannel.

36. The process of claim 34 wherein the catalyst is supported by a support, the support being made of a material comprising one or more of silica gel, foamed copper, sintered stainless steel fiber, steel wool, alumina, poly(methyl methacrylate), polysulfonate, poly(tetrafluoroethylene), iron, nickel sponge, nylon, polyvinyl idene difluoride, polypropylene, polyethylene, polyethylene ethylketone, polyvinyl alcohol, polyvinyl acetate, polyacrylate, polymethylmethacrylate, polystyrene, polyphenylene sulfide, polysulfone, polybutylene, or a combination of two or more thereof.

37. The process of claim 34 wherein the catalyst comprises a heat conductive material.

38. The process of claim 34 wherein the catalyst is supported on a support having a flow-by configuration, a flow-through configuration, a honeycomb structure or a serpentine configuration.

39. The process of claim 34 wherein the catalyst is supported on a support, the support being in the form of a foam, felt, wad, fin, or a combination of two or more thereof.

40. The process of claim 34 wherein the catalyst is supported on a support, the support comprising a fin assembly comprising at least one fin.

41. The process of claim 34 wherein the catalyst is supported on a support, the support comprising a microgrooved support strip.

42. The process of claim 1 wherein the process is conducted in a microchannel processing unit comprising one or more inlet manifolds and a plurality of the process microchannels, the process comprising flowing a Newtonian and/or non-Newtonian fluid through the one or more inlet manifolds and distributing the Newtonian and/or non-Newtonian fluid to the plurality of process microchannels, the Quality Index Factor being less than about 20%.

43. The process of claim 1 wherein the process is conducted in a microchannel processing unit comprising a plurality of the process microchannels, the process comprising flowing the non-Newtonian fluid in the plurality of process microchannels, the shear rate of the non-Newtonian fluid in the process microchannels being in excess of about $100\,\text{sec}^{-1}$, the shear force deviation factor being less than about 2.

44. The process of claim 1 wherein the process is conducted in a microchannel processing unit comprising an inlet manifold and a plurality of the process microchannels, the process comprising flowing a non-Newtonian fluid through the manifold and distributing the non-Newtonian fluid to the plurality of process microchannels, the non-Newtonian fluid flowing straight through the inlet manifold without making any turns in the manifold.

45. The process of claim 1 wherein the process is conducted in a microchannel processing unit comprising an inlet manifold and a plurality of the process microchannels, the process comprising flowing a Newtonian fluid through the manifold and distributing the Newtonian fluid to the plurality of process microchannels, the Newtonian fluid flowing into the inlet manifold and making at least one turn in the inlet manifold prior to entering the process microchannels.

46. The process of claim 1 wherein the process is conducted in a microchannel processing unit comprising an inlet manifold and a plurality of the process microchannels, the process comprising flowing a feed stream through the inlet manifold and distributing the feed stream to the plurality of process microchannels, the feed stream contacting flow resistors in the inlet manifold.

47. The process of claim 1 wherein the process is conducted in a microchannel processing unit comprising an inlet manifold and a plurality of the process microchannels, the process comprising flowing a feed stream through the inlet manifold and distributing the feed stream to the plurality of process microchannels, the feed stream flowing through flow distribution features.

48. The process of claim 1 wherein the average shear rate in one process zone differs from the average shear rate in another process zone by a factor of at least about 1.5.

49. The process of claim 1 wherein the average shear rate in one process zone differs from the average shear rate in another process zone by a factor of at least about 2.

* * * * *